(12) United States Patent
Feldman

(10) Patent No.: US 7,288,273 B1
(45) Date of Patent: Oct. 30, 2007

(54) GALLOTANNINS AND ELLAGITANNINS AS REGULATORS OF CYTOKINE RELEASE

(75) Inventor: Kenneth S. Feldman, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 745 days.

(21) Appl. No.: 10/130,632

(22) PCT Filed: Nov. 17, 2000

(86) PCT No.: PCT/US00/31648

§ 371 (c)(1),
(2), (4) Date: Oct. 15, 2002

(87) PCT Pub. No.: WO01/36436

PCT Pub. Date: May 25, 2001

(51) Int. Cl.
*A61K 36/00* (2006.01)
*A61K 9/00* (2006.01)

(52) U.S. Cl. .................. 424/776; 424/725; 424/400

(58) Field of Classification Search ................ 424/776
See application file for complete search history.

(56) References Cited

U.S. PATENT DOCUMENTS 5,387,609 A * 2/1995 Morita et al. ............... 514/548
5,773,419 A * 6/1998 Falcon ......................... 514/25
6,063,770 A * 5/2000 Falcon ......................... 514/25

FOREIGN PATENT DOCUMENTS

| CA | 2001898 | 4/1990 |
|----|---------|--------|
| EP | 0 297 547 | 1/1989 |
| EP | 0 374 888 A | 6/1990 |
| EP | 0 727 218 A2 | 8/1996 |
| FR | 2 695 390 A | 3/1994 |
| JP | 09 059151 A | 3/1997 |
| WO | WO 90/04968 | 5/1990 |

OTHER PUBLICATIONS

Feldman et al. "Immunostimulation by plant polyphenols: a relationship between tumor necrosis-factor-.alpha. production and tannin structure" Bioorg.med.chem.lett (1999), 9(7), p. 985-990.*
Patent Abstracts of Japan, filed Jul. 31, 1997, KAO Corporation, vol. 1997, No. 07 & Abstract.
Feldman, et al.; "Immunostimulation by Plant Polyphenols: A Relationship Between Tumor Necrosis Facotr-α Production and Tannin Structure"; Bioorganic & Medicinal Chemistry Letters 9(7) (1999) pp. 985-990 1999, XP004162570.
Feldman, Ken et al.; "Ellagitannin Chemistry, Syntheses of Tellimagrandin II and a Dehydrodigalloyl Ether-Containing Dimeric Gallotannin Analogue of Coriariin A"; J. Org. Chem. 1999, 64(1), 209-216, 1999, XP002162591.
Miyamoto, Ken-Ichi et al.; "Antitumor Activity and Interleukin-1 Induction by Tannins"; AntiCancer Research (1993), 13(1), 37-42, 1993, XP000984884.

* cited by examiner

*Primary Examiner*—Christopher R Tate
*Assistant Examiner*—Randall Winston
(74) *Attorney, Agent, or Firm*—McKee, Voorhees & Sease, P.L.C.

(57) ABSTRACT

A means and method for increasing or inhibiting the secretion of cytokines using gallotannins and ellagitannins is described. The preferred cytokine release inhibiting compounds are dimeric gallotannins having a linker molecule that misaligns the carbohydrate cores of the compounds. The preferred cytokine release promoting gallotannins and ellagitannins include a diaryl ether linker unit. In comparison to the more structurally complex ellagitannins, the compounds of this invention are structurally simpler, easier to synthesize, and more potent.

3 Claims, 17 Drawing Sheets

GALLOTANNINS AND ELLAGITANNINS AS REGULATORS OF CYTOKINE RELEASE

GRANT REFERENCE CLAUSE

This invention was funded in part by a grant from the National Institutes of Health (NIH), grant number GM 35727. The government may have certain rights in this invention.

FIELD OF THE INVENTION

This invention relates to gallotannins and elligitannins as regulators of the production and secretion of cytokines, including tumor necrosis factor-α (TNF-α) and interleukin-β (IL-1β), their synthesis, and methods of their use in diseases and conditions affected by increased or decreased release of cytokines.

BACKGROUND OF THE INVENTION

Gallotannins and ellagitannins are members of the hydrolyzable tannin class of plant polyphenols. Tannins are secondary metabolites found throughout the plant kingdom that were first isolated and characterized in the 1950's. To date, over 500 ellagitannins and 200 gallotannins have been identified.

Gallotannins are the simplest hydrolyzable tannins. Compounds of this species consist of a carbohydrate core, usually glucose, which has been acylated with gallic acid. Variations among the gallotannins arise from differences in the stereochemistry at the anomeric carbon and the extent of galloylation about the carbohydrate core.

The more complex ellagitannins are comprised of the same building blocks as gallotannins. The defining characteristic of an ellagitannin is the presence of at least one hexahydrodiphenoyl moiety (HHDP), presumably formed by intramolecular oxidative C—C coupling between two galloyl groups. The HHDP units have been identified as bridging the 1,6-, 1,3-, 3,6- and 2,4-positions of the carbohydrate core, but are most often found between positions 2 and 3 or 4 and 6.

Ellagitannins can be either monomeric or oligomeric. Variations among simple ellagitannins include differences in the stereochemistry at the anomeric carbon and the number, positioning and stereochemistry of the HHDP units. Higher order tannins can be dimeric, trimeric, or tetrameric. The carbohydrate cores of oligomeric ellagitannins are joined by either a dehydrodigalloyl functionality most likely formed by intermolecular C—O oxidative coupling between two anomeric galloyl units, or by similar bonding between a galloyl group and an HHDP unit.

Lipopolysaccharide (LPS), or bacterial endotoxin, is a component of the cell wall in all gram-negative bacteria. The structure of LPS consists of four sections that are covalently linked: an O-specific chain which is comprised of oligosaccharides, an outer core and an inner core, made up of octulosonic acids and heptopyranoses, and a lipid membrane anchor, termed lipid A. Host immune cell response to LPS involves secretion of the cytokines interleukin-1β (IL-1β) and TNF-α. Overproduction of these cytokines, in particular TNF-α, can result in sepsis and septic shock.

Sepsis is caused by production of low levels (<1 ng/mL) of TNF-α as a result of exposure to LPS from a gram-negative bacterial infection. Characteristic symptoms of sepsis are hypothermia, fever and an increase in white blood cell count. Production of higher levels of TNF-α (>100 ng/mL) can result in the potentially lethal condition septic shock. Septic shock causes more than 20,000 deaths per year in the United States alone, and is the leading cause of death in intensive care units. This condition causes circulatory collapse, resulting in multiple organ failure and cardiovascular prolapse.

The lipid A portion of LPS mediates the endotoxic activity of the molecule. The process is initiated by bacterial lysis, resulting in liberation of LPS from the bacterial cell wall and exposure of lipid A. At low concentrations in the serum, LPS is bound by an LPS binding protein (LBP). This dimeric complex ligates to a membrane bound receptor on peripheral blood mononuclear cells' (PBMC's) CD14. CD14 must associate with (or otherwise activate) a second receptor identified as Tlr4 to initiate the signal transduction that results in cytokine release. At high concentrations of LPS, direct binding to a second membrane-bound receptor, L-selectin, is possible, which also results in cytokine release.

It is unknown how LPS interacts with LBP, or how the LPS/LBP complex ligates to CD14. It is know that synthetic and natural $E.\ coli$ lipid A exhibit the highest endotoxicity compared to all other synthetic and natural lipid A samples. Attempts to identify the structural features of $E.\ coli$ lipid A which impart the endotoxic activity have yielded negative results. Any variations in the structure of $E.\ coli$ lipid A causes a decrease or lack of endotoxicity.

Currently, there are no widely effective treatments for septic shock. Current approaches to inhibiting LPS-induced bacterial sepsis include use of 1) LPS antagonists which presumably block the lipid A/receptor interactions; or 2) monoclonal antibodies which are designed to sequester various components of the septic shock response (LPS, TNF-α, TNF-α receptors, LPS receptors, etc.). The former strategy has generally relied on either lipid A analogs/derivatives which are quite potent, but so structurally complex as to render scale-up production problematic, or on small molecule agents which are more accessible but much less potent. The latter approach is hampered by cost concerns, and ultimately has been disappointing in in vivo efficacy trials.

Overproduction of TNF-α and other cytokines is also believed to underlie several debilitating diseases, such as leprosy, rheumatoid arthritis, and cachexia, the latter achieving notoriety in the context of late-stage AIDS. Consequently, inhibition of cytokine secretion has become the goal of numerous therapies.

Increasing TNF-α levels has been a focal point of numerous therapeutic regimes targeted at tumor remission. In the most favorable cases, administering relatively high concentrations of TNF-α directly to tumor sites has produced striking responses in patients with melanoma and sarcoma. Barbara et al. 1996. However, systemic application of TNF-α is an ineffective therapy as a consequence of its severe inflammatory effects (similar to IL-1β) and rapid clearance from serum ($t_{1/2} \approx 6.5$-10.5 min). Sanches-Cantu et al. 1991.

The ellagitannin subfamily of the hydrolyzable tannins spans over 500 structurally characterized members. An increasing interest in the role played by these secondary plant metabolites in polyphenol-rich folk medicines from China and Japan has led to the identification of several ellagitannins which hold promise as potent antiviral and anticancer therapeutic agents. See e.g. Berlinck et al. (1995).

A number of oligomeric ellagitannins, including coriariin A and the structurally related species agrimoniin and gemin A have been found to induce tumor regression in mice infected with sarcoma-180 tumors through the increase of production of IL-1β. Miyamoto et al., *Chem. Pharm. Bull.* 1987 and *Anticancer Res.* 1993. The monomeric ellagitannins tellimagrandin I, tellimagrandin II, β-D-PGG and pedunculagin have been found to be much less effective antitumor agents.

The present inventors have now surprisingly discovered that certain gallotannins and ellagitannins play a role in either up-regulating and down-regulating the production of TNF-α and other cytokines. Some of these compounds have been found to be useful in decreasing secretion of TNF-α, thereby making them suitable in the development of treatments for diseases associated with overproduction of TNF-α, such as septic shock, leprosy, and cachexia. Other gallotannins have been found to be effective in increasing TNF-α levels for use in tumor remission.

Accordingly, it is a primary objective of the present invention to provide compositions and methods for regulating the production of cytokines, such as TNF-α and IL-1β using gallotannins and ellagitannins.

It is a further objective of the present invention to provide a composition and method for increasing levels of TNF-α and other cytokines to induce tumor remission using gallotannins and ellagitannins.

It is a further objective of the present invention to provide a composition and method for treating diseases associated with acute overproduction of cytokines, including IL-1β and TNF-α, such as in sepsis and septic shock, using gallotannins.

It is still a further objective of the present invention to provide a composition and method for treating diseases associated with chronic overproduction of lower levels of cytokines, including IL-1β and TNF-α, such as leprosy, rheumatoid arthritis, and cachexia, using gallotannins.

It is a further objective of the present invention to provide compositions and methods for regulating the production of TNF-α using gallotannins and ellagitannins that have low toxicity.

It is a further objective of the present invention to provide compositions and methods for regulating the production of TNF-α using gallotannins and ellagitannins that are effective in vivo.

It is yet a further objective of the present invention to provide compositions and methods for regulating the production of TNF-α and other cytokines using gallotannins and ellagitannins that are simple to synthesize and economical to manufacture.

It is yet a further objective of the present invention to provide compositions and methods for regulating the production of TNF-α and other cytokines using gallotannins which are LPS antagonists.

It is a further objective of the present invention to provide compositions and methods for regulating the production of TNF-α and other cytokines using gallotannins and ellagitannins which are LPS agonists.

It is still a further objective of the present invention to provide compositions and methods for regulating the production of TNF-α and other cytokines using gallotannins that induce little or no secretion of the cytokine IL-1β.

The method and means of accomplishing each of the above objectives as well as others will become apparent from the detailed description of the invention which follows hereafter.

SUMMARY OF THE INVENTION

The invention describes a method and composition for regulating the production of cytokines using gallotannins and ellagitannins, their prodrugs and analogues. Specifically, the compounds of this invention have low toxicity and, depending on their structure, have been found to be effective in functioning as either cytokine antagonists or agonists.

Cytokine antagonists of this invention consist of the monomeric gallotannin β-pentagalloylglucose, and the preferred dimeric gallotannins whereby the linker molecule joining the two carbohydrate cores of the compounds causes a misalignment of the cores. In this respect, the linker molecule should not be a diaryl ether since this linker molecule aligns the carboydrate cores and enables the compounds to function as cytokine agonists. These antagonists are effective in the treatment of sepsis/septic shock and other chronic and acute conditions associated with an overproduction of cytokines, such as leprosy, rheumatoid arthritis, and cachexia.

The agonists of this invention are dimeric gallotannins and ellagitannins having an ether linkage joining the carbohydrate cores of the compounds. These compounds promote the release of TNF-α, which in turn induces the production of IL-1β and other cytokines, making them effective in numerous anticancer strategies. The invention further includes a novel scheme for the synthesis of coriariin A, as well as the biomimetic synthesis of the monomeric precursor to coriariin A, tellimagrandin II.

DETAILED DESCRIPTION OF THE PREFERRED EMBODIMENT

Figure 1:
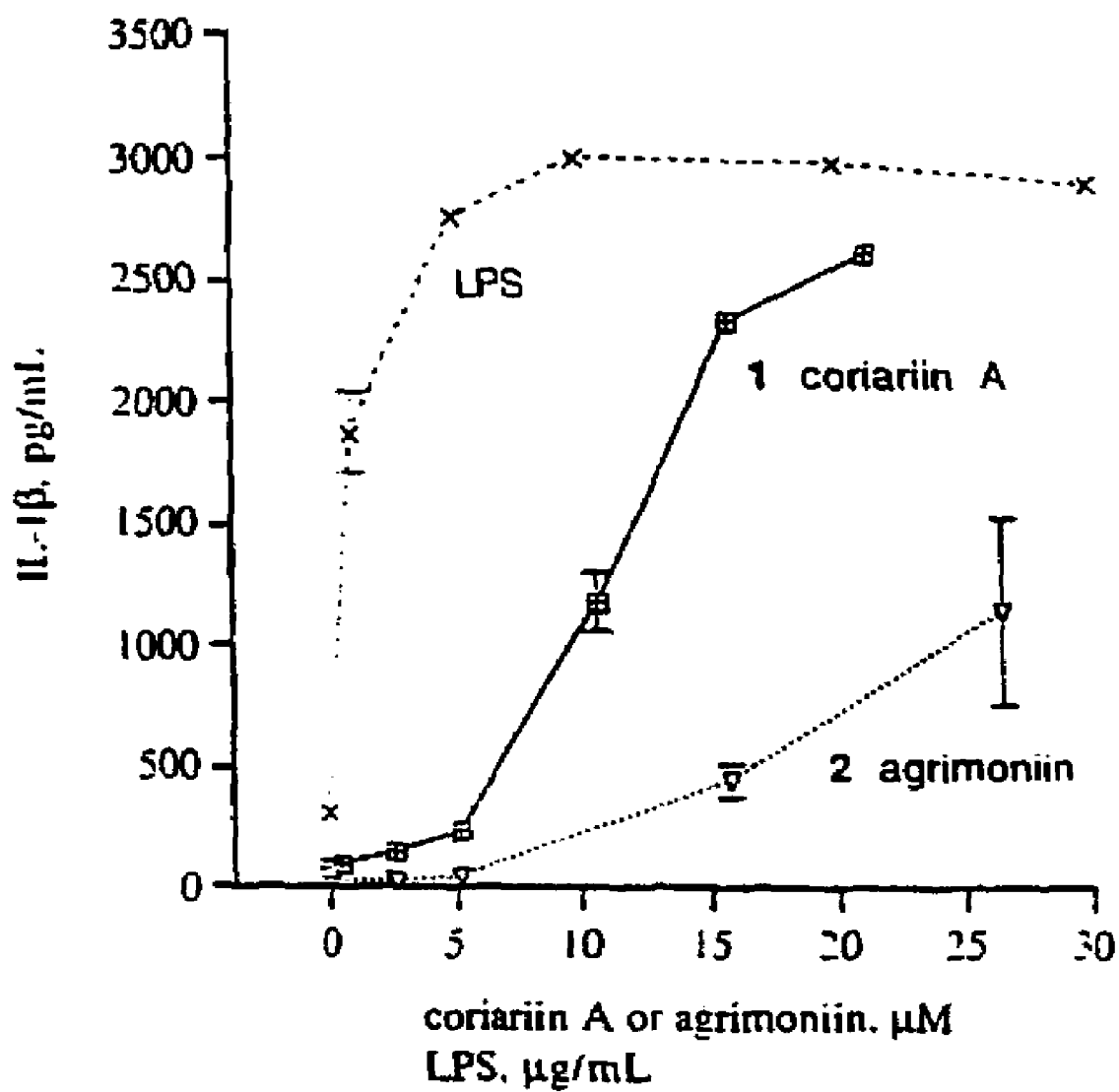
FIG. 1 shows IL-1β release from human peripheral blood mononuclear cells (h-PBMC's) upon 4 h exposure to varying concentrations of coriariin A, agrimoniin, and LPS.

The present invention relates to the development of gallotannins and ellagitannins for regulating the secretion of TNF-α and other cytokines. The present invention is predicated upon the discovery that tannins appear to operate through the same biological pathway as LPS, at least to the extent of utilizing the Tlr4 receptor. Depending on their structure, the monomeric and dimeric gallotannins of this invention are effective in either increasing or inhibiting the production and release of TNF-α and other cytokines. TNF-α-antagonists of this invention are effective in treating septic shock and other diseases and conditions associated with overproduction of TNF-α and other cytokines by reducing the secretion of cytokines and, with respect to the preferred compounds, causing little or no secretion of IL-1β. TNF-α-agonists are effective in increasing secretion of TNF-α and other cytokines, and therefore possess activity against tumors.

For the past several years, members of the ellagitannin subfamily of hydrolyzable tannins have offered many contemporary challenges in organic synthesis, as well as many exciting opportunities in both anti-cancer and anti-septic shock chemotherapies. The hydrolyzable tannins comprise both the conformationally flexible, weakly-protein-binding gallotannins (Kd≈mM) as well as the ellagitannins. Prior to this invention, it was believed that only members of the latter class were capable of providing the requisite degree of receptor association necessary for selective biological activity ($IC_{50}$'s≈μM to nM).

The present inventors have now surprisingly discovered that simple monomeric and dimeric gallotannins and ellagitannins are capable of providing the requisite degree of association with the LPS receptor to provide selective release or inhibition of the release of TNF-α and other cytokines. In comparison to ellagitannins, the gallotannin compounds are relatively easier to synthesize and, like the ellagitannins, exhibit a low degree of cytotoxicity. Further, the gallotannins and ellagitannins of this invention have proven to be even more specific for the TNF-α receptor than previously known tannin compounds, and have shown effectiveness in anticancer and antiseptic shock strategies.

As noted above, the ellagitannin family of plant polyphenols spans a class of over 500 structurally diverse members. An increasing interest in the role played by these secondary plant metabolites in tannin-rich folk medicines from China and Japan has led to the identification of several ellagitannins which display high levels of activity in anticancer and antiviral assays. These ellagitannins typically exhibit inherently low cytotoxicity and, thus, have been explored in the development of novel therapeutics.

An examination of the in vivo antitumor potency of several ellagitannins has shown that the dimeric ellagitannins are more potent tumoricidal agents compared to the monomeric (gallo)ellagitannins. Miyamoto, *Chem. Pharm. Bull.* 1987. The intraperitoneal administration of tannins to mice before or after sarcoma-180 tumor inoculation elicits the same extent of tumor regression. Miyamoto, *Jpn. J. Pharmacol.* 1987. These observations suggested that endogenously inducible factors may play a role in the antitumor activity of the ellagitannins.

Miyamoto's in vitro studies on the molecular basis for the antitumor activity of a range of tannins revealed their ability to stimulate the secretion of interleukin-1β (IL-1β) from both mouse peritoneal exudate cells and human peripheral blood mononuclear cells (h-PBMC's). Miyamoto, *Chem. Phar. Bull.* peripheral blood mononuclear cells (h-PBMC's). Miyamoto, *Chem. Phar. Bull.* 1987. IL-1β is capable of upregulating the activity of tumoricidal natural killer cells, prompting the Hokuriku group's suggestion that this cytokine mediates the it vivo antitumor activity of the ellagitannins. Miyamoto, *Anticancer Res.* 1993.

The present inventors have unexpectedly found that TNF-α appears to be the cytokine responsible for immuno-mediated tumor remission. Thus, since it has now been shown that tannins stimulate TNF-α secretion, Miyamoto's measurement of IL-1β levels actually may have reflected at least some secondary production attributable to nascent TNF-α.

The TNF-α agonists of this invention are dimeric gallotannins and ellagitannins having a diaryl ether linking unit. Preferred compounds of this invention are the naturally occurring dimeric ellagitannins coriariin A and agrimoniin, and gallotannin analogs of coriariin A. The structures of coriariin A and agrimoniin are set forth below:

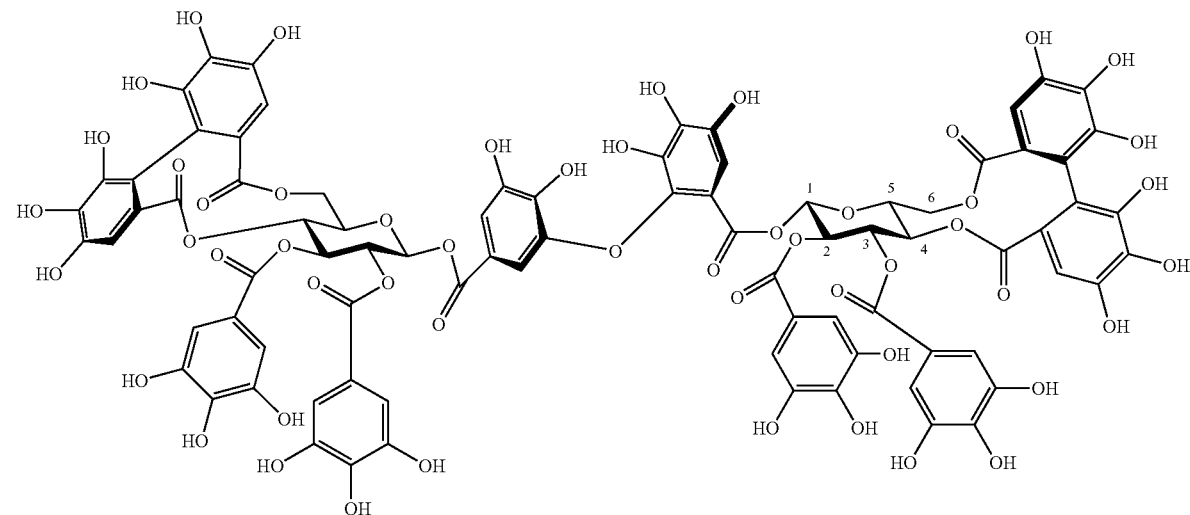

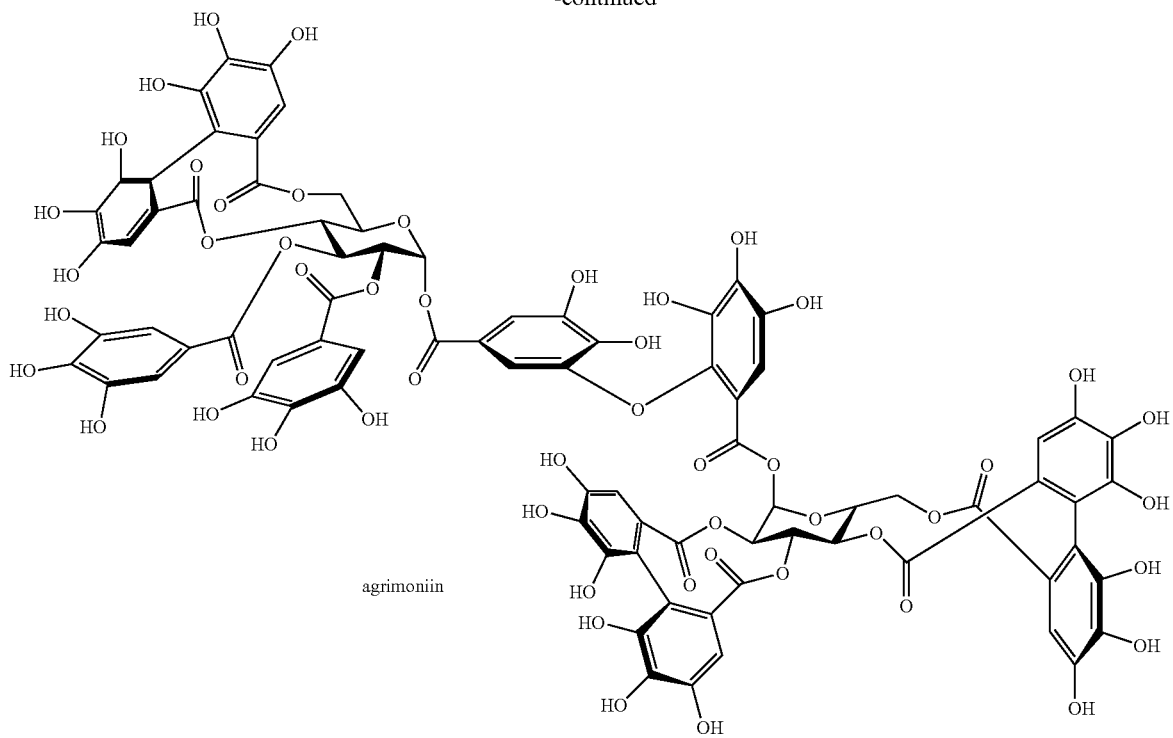

agrimoniin

The most preferred compound of this invention has the following structure:

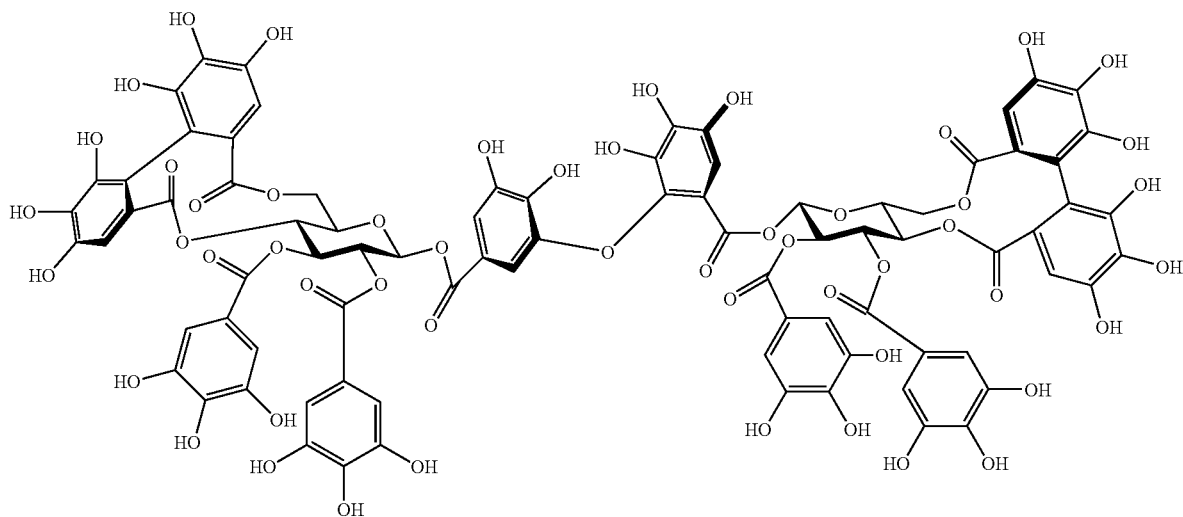

As can be appreciated, this analog of the naturally occurring dimeric ellagitannin coriariin A is identical to the parent compound except that it lacks the O(4)/O(6) coupled HHDP units of coriariin A.

The synthesis of the agonists of this invention also serves as a model for a novel synthesis plan for coriariin A. In addition, the biomimetic synthesis of the monomeric precursor to coriariin A, tellimagrandin II is described herein.

Any strategy directed towards the synthesis of the TNF-α agonists of this invention must address two key issues: 1) formation of the dehydrodigalloyl ether linking unit, and; 2) establishment of the β-anomeric galloyl linkage with stereochemical control. In addition to anomeric ester stereochemistry, the telligrandin II synthesis requires 1) stereoselective formation of the (S)-atropisomer of the HHDP moiety, and 2) selective manipulation of the anomeric center in a manner which is compatible with other functional groups present in the molecule. Pb(OAc)$_4$-mediated oxidative galloyl coupling has proved to be a robust strategy for the preparation of stereochemically secure (S)-HHDP units. The β-anomeric galloyl linkages in both the TNF-α agonists and tellimagrandin II may be secured by coupling of the anomeric hydroxy group of an appropriately protected intermediate with a galloyl chloride in the presence of a suitable base.

The inventors pursued a biomimetic approach via dimerization of two activated β-D-PGG units. This route is shown below:

Scheme 3

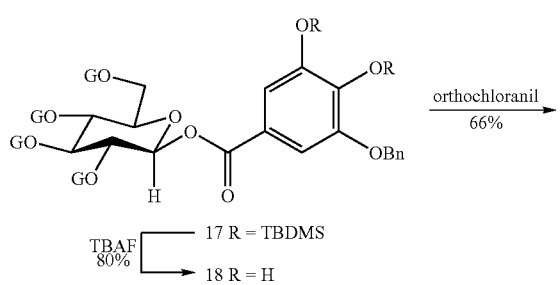

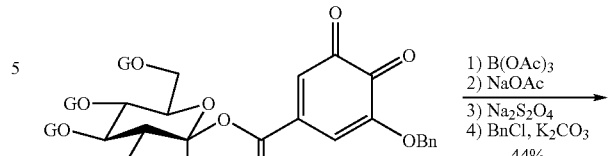

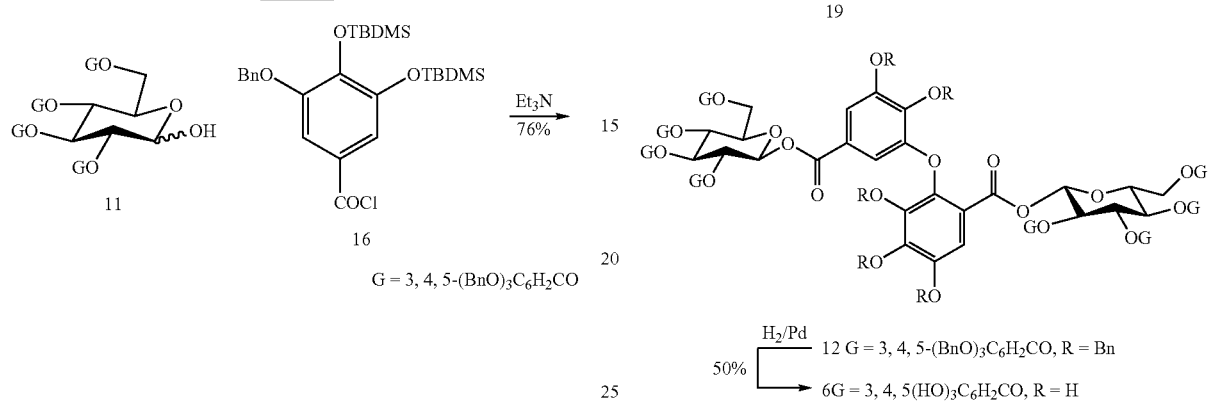

Here, acylation of the alcohol 11 was achieved with the galloyl chloride 16 in the presence of triethylamine which provided the pentaester 17 featuring strictly β-stereochemistry at the anomeric position. Desilyation of compound 17 furnished the catechol 18 which was oxidized to the orthoquinone 19 with orthochloranil. The orthoquinone 19 precipitates cleanly from the reaction mixture, obviating the need for further purification of this sensitive compound. The B(OAc)₃-mediated Diels-Alder dimerization of the orthoquinone 19 followed by a three step reduction/rearrangement sequence furnished the perbenzylated gallotannin dimer 12 in 44% yield starting from the orthoquinone 19. In the final step, hydrogenolysis of the benzyl esters in 12 furnished the dimeric gallotannin in 50% yield.

The synthesis of tellimagrandin II 2 begins with the known acetal 20. See the synthesis scheme below:

Scheme 4

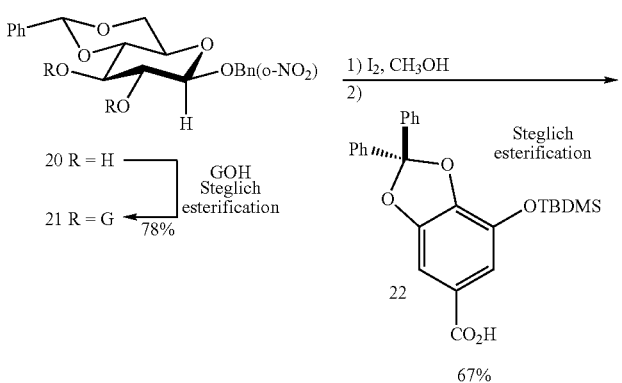

-continued
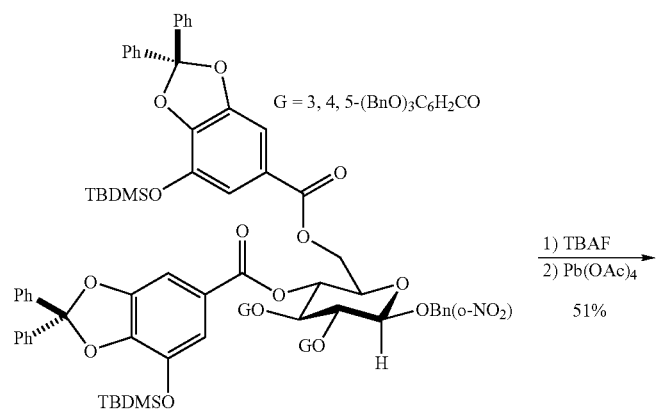
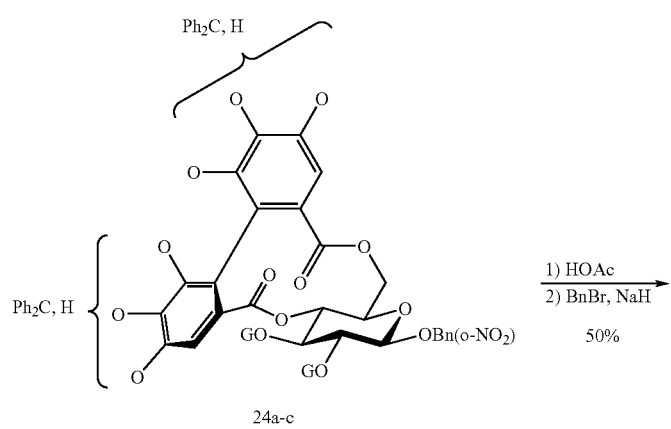
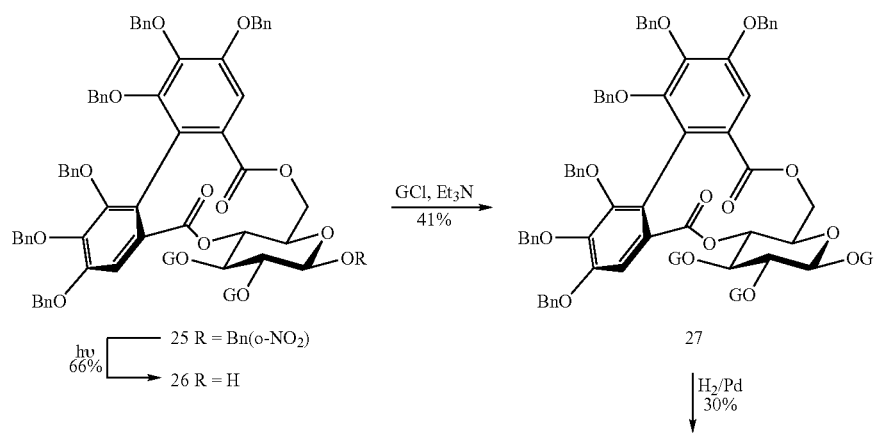

-continued

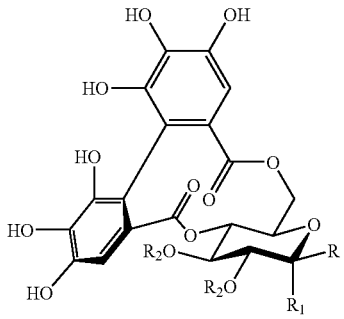

2 R = OG, R₁ = H, R₂ = G

Galloylation at the 2 and 3 positions of the carbohydrate core furnishes the diester 21 in 78% yield. Deprotection of the O(4), O(6) benzylidene acetal in 21 provided an 84% yield of an intermediate diol which was immediately esterified at both the O(4) and O(6) positions with excess 22 to provide the tetragalloyl compound 23. Desilylation of bis silyl ether 23 provides the oxidative cyclization precursor. Intramolecular PB(OAc)₄-mediated oxidative coupling of the galloyl groups at the O(4) and O(6) positions in this bis phenol furnishes the 4,6-(S)—HHDP bearing compounds 24a-c in 67% yield as a mixture of three regioisomers. Hydrogenolysis of the diphenylmethylene ketals in 24a-c is a capricious reaction, and hence a two-step deprotection/protection strategy was adopted. The diphenylmethylene ketals of 24a-c are cleaved with 80% HOAc, and the resulting hexaphenolic compound is directly benzylated to provide, now as a single isomer, in 50% yield over two steps.

The presence of benzyl esters at all of the phenolic positions proves advantageous in the final stages of the tellimagrandin II synthesis because they impart favorable chromatographic and spectroscopic properties to late intermediates while preserving the means to deliver pure polyphenolic product in the final step. Selective photochemical cleavage of the O(1)-nitrobenzyl ether of 25 furnishes a 66% yield of the perbenzylated tellimagrandin I derivative 26 featuring a free anomeric hydroxyl group. Esterification of 3,4,5-tribenzylbenzoyl chloride with this alcohol in the presence triethylamine provides 27 as the exclusively β-esterified product in 41% yield. In the final step, hydrogenolysis of the benzyl ethers in 27 furnishes crude tellimagrandin II which is purified by repeated filtration and trituration with hexanes and diethyl ether to yield 2 in 30% yield as a gray solid. All spectral data for the chemically synthesized tellimagrandin II 2 correlates with the published data for the naturally occurring compound. The presence of the (S)—HHDP atropisomer is confirmed by CD measurement.

In summary, the first total synthesis of a dehydrodigalloyl ether-containing dimeric gallotannins from a gallotannin orthoquinone intermediate has been achieved. This synthesis demonstrates the value of the B(OAc)₃-mediated Diels-Alder dimerization of orthoquinones in accessing this class of compounds. Additionally, the synthesis of tellimagrandin II, a biosynthetic precursor to coriariin A has been demonstrated.

The cytokine antagonists of this invention include the monomeric gallotannin β-PGG and the preferred dimeric gallotannins that have a non-diaryl linker unit joining the two carbohydrate cores of the compounds.

The present inventors discovered that the monomeric gallotannin β-PGG is effective in inhibiting LPS induced secretion of TNF-α from h-PBMC's. The structure of β-PGG is set forth below:

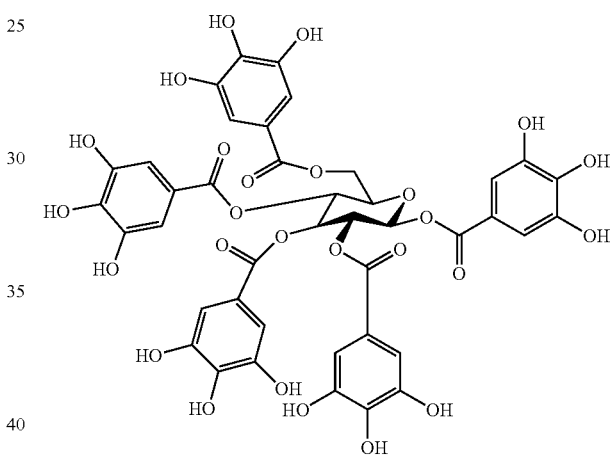

Preliminary in vivo results have shown β-PGG to be effective in inhibiting the release of TNF-α and other cytokines. The inventors have found that a large amount of β-PGG is required in order to elicit inhibition since β-PGG is a small monomeric gallotannin that is able to interact with other blood proteins, such as rat serum albumin. In addition, even though rats treated with β-PGG showed lower levels of TNF-α secretion, a septic shock response in the form of low blood pressure was still observed. This physiological effect is believed to be due to secretion of the cytokine IL-1β which also has been shown to mediate septic shock. β-PGG causes secretion of high levels of IL-1β from h-PBMC's. The inventors therefore tested other dimeric gallotannins in order to find an inhibitor of TNF-α that is more selective in its biological interactions, and which results in the release of little or no IL-1β.

The preferred cytokine antagonists of this invention are dimeric gallotannins having a linker unit joining the two carbohydrate cores. Unlike the diaryl ether linkage of the agonists of the invention, the linker unit of the cytokine antagonists causes the carbohydrate cores to misalign, giving the compounds their antagonistic activity. Thus, the linker unit of the antagonists of this invention cannot be a diaryl ether.

Preferred antagonists have the following general structure:

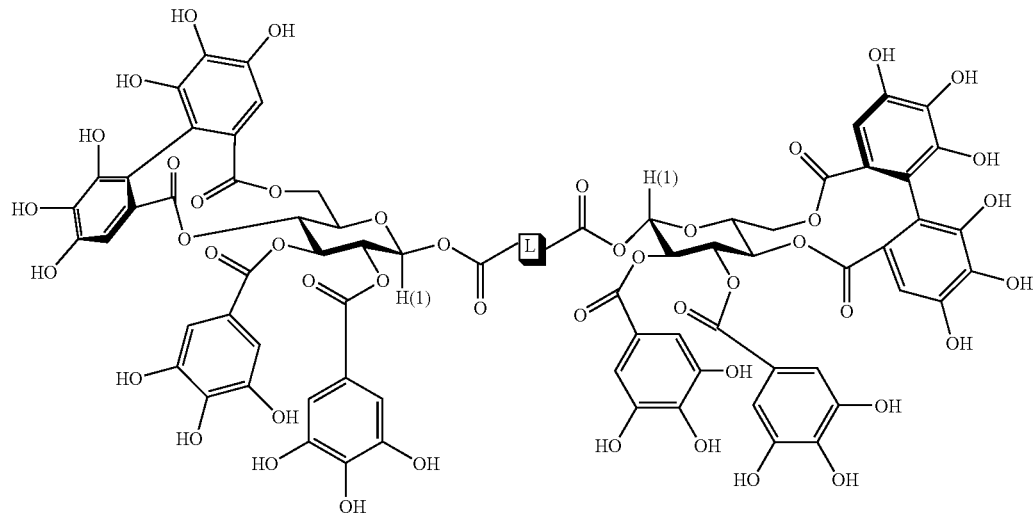

Wherein L is selected from the group consisting of:

17

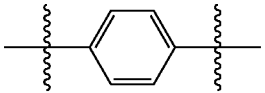

18

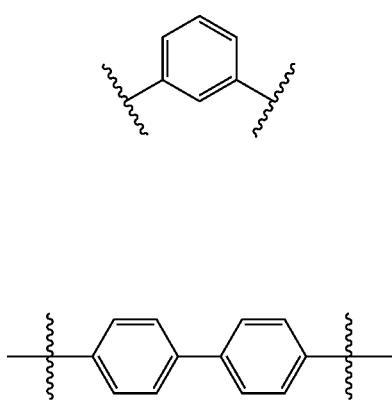

-continued

21

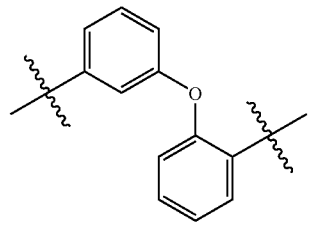

These preferred compounds cause less secretion of cytokines than does β-PGG, and are able to inhibit LPS induced levels of TNF-α in PBMC's.

The most preferred antagonists of this invention have linker molecules selected from the group consisting of:

19

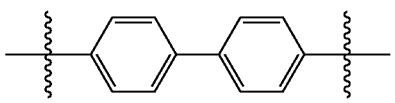

20

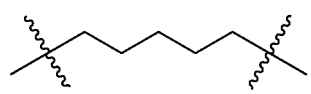

19

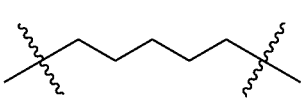

20

These antagonists are most preferred since they cause very little or no secretion of IL-1β. As noted above, the cytokine IL-1β is also released in an LPS-stimulated septic shock response. The compounds that cause very little secretion of IL-1β or none at all will be the optimal compounds for potential septic shock therapeutics because they are less likely themselves to induce a septic shock response.

The synthesis of the dimeric gallotannin cytokine antagonists involves the straightforward coupling of the appropriate bisacid chloride with the alcohol 22, as shown in the following reaction scheme:

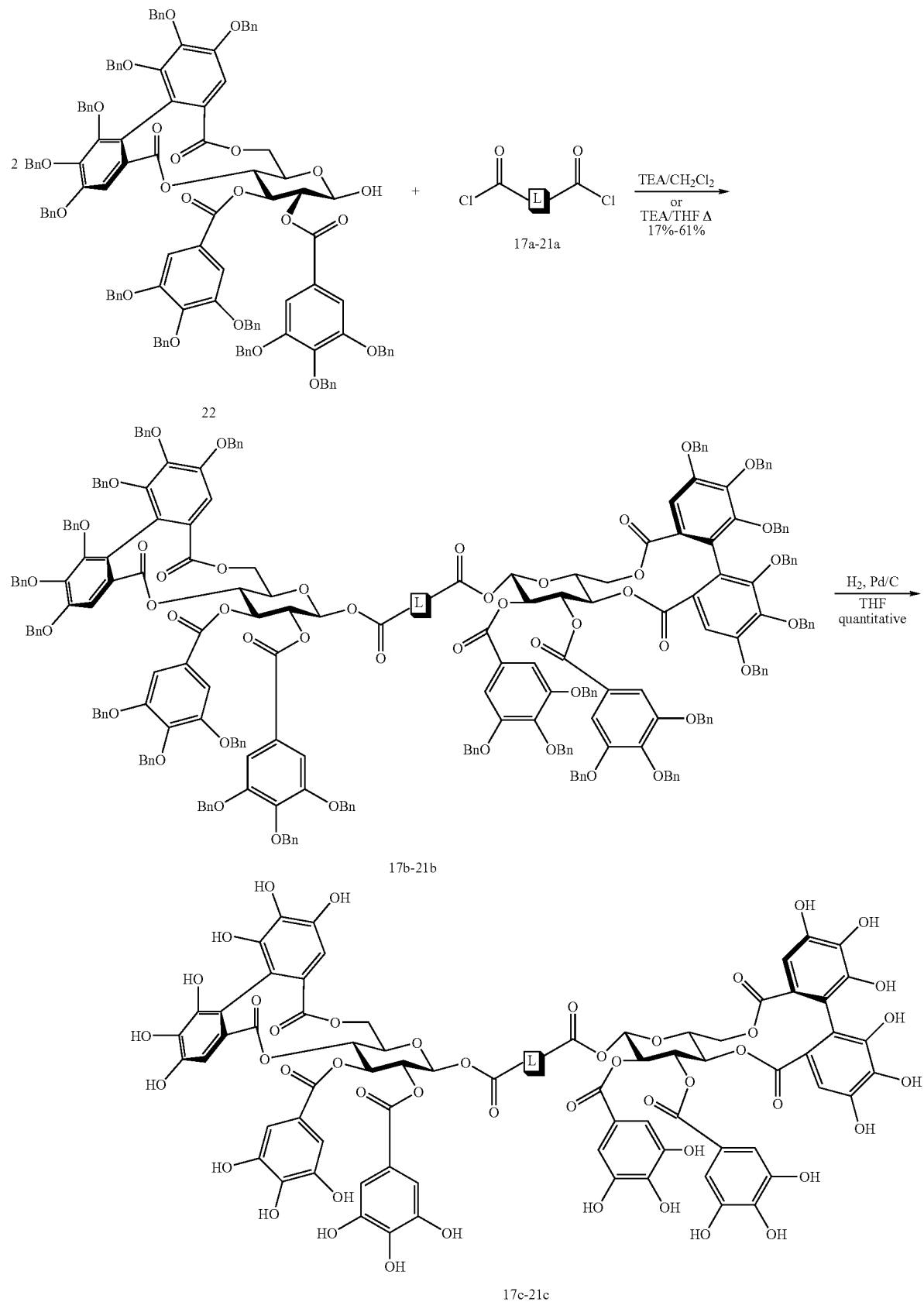

This coupling is followed by benzyl ether hydrogenation to afford the final products 17c-21c. The couplings that furnish 17b, 18b, and 21b proceed with high diastereoselectivity for the β,β' anomer. The synthesis of 19b requires higher temperatures than the other analogs. This analog is obtained in a 4:1 ratio of β,β' to α,α' anomeric stereochemistry as determined by $^1$H NMR. The H(1) proton for the α,α' anomer appears farther downfield (6.88 ppm) and has a smaller coupling constant (J=3.2 Hz) than the H(1) proton for the β,β' anomer (6.02 ppm, J=9.8 Hz). The synthesis of 20b results in a mixture of β,β', α,α', and α,β' anomers. However, slow addition of 20a to the alcohol 22 gives predominantly the β,β' isomer. The H(1) proton for the α anomers appears at 6.69 ppm with a coupling constant of 4.15 Hz.

Acid chlorides 19a and 20a are not commercially available, but are readily prepared. For example, 19a may be prepared by conversion of the bisacid 23 to the acid chloride using oxalyl chloride and catalytic DMF, as shown below:

Scheme 8

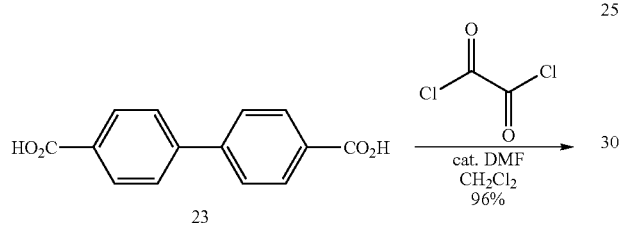

Compound 21a was prepared in three steps. The diaryl ether ester 24 was prepared by Ullmann coupling. Hydrolysis of 24 resulted in the bisacid 25 which was converted to the acid chloride 21a by oxalyl chloride and catalytic DMF, as shown below:

Scheme 9

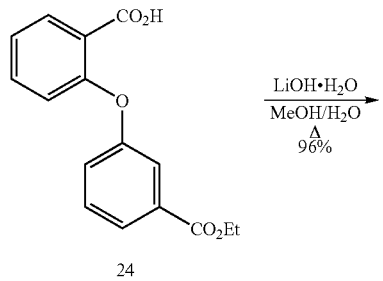

-continued

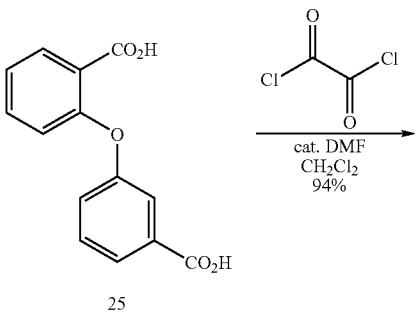

The cytokine agonists and antagonists of the present invention may be generally used in the treatment of cancer, septic shock, and other diseases and conditions wherein it is desired to increase or inhibit the secretion of cytokines. The gallotannins and ellagitannins of the present invention are administered along with a pharmaceutically acceptable carrier. Any pharmaceutically acceptable carrier may be generally used for this purpose, provided that the carrier does not significantly interfere with the stability or bioavailability of the gallotannins and ellagitannins.

The gallotannins and ellagitannins of this invention can be administered in any effectively pharmaceutically acceptable form to warm blooded animals, including human and other animal subjects, e.g. in topical, lavage, oral, suppository, parenteral, or infusible dosage forms, as a topical, buccal, sublingual, or nasal spray or in any other manner effective to deliver the agents. The route of administration will preferably be designed to optimize delivery and/or localization of the agents to cytokine receptors.

In addition to the active compounds i.e. the gallotannins, the pharmaceutical compositions of this invention may contain suitable excipients and auxiliaries which facilitate processing of the active compounds into preparations which can be used pharmaceutically. Oral dosage forms encompass tablets, capsules, granules, and dragees. Preparations which can be administered rectally include suppositories. Other dosage forms include suitable solutions for administration parenterally or orally, and compositions which can be administered buccally or sublingually.

The pharmaceutical preparations of the present invention are manufactured in a manner which is itself well known in the art. For example the pharmaceutical preparations may be made by means of conventional mixing, granulating, dragee-making, dissolving, lyophilizing processes. The processes to be used will depend ultimately on the physical properties of the active ingredient used.

Suitable excipients are, in particular, fillers such as sugars for example, lactose or sucrose mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Dragee cores may be provided with suitable coatings which, if desired, may be resistant to gastric juices.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet of dragee coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition stabilizers may be added. Possible pharmaceutical preparations which can be used rectally include, for example, suppositories, which consist of a combination of the active compounds with the suppository base. Suitable suppository bases are, for example, natural or synthetic triglycerides, paraffinhydrocarbons, polyethylene glycols, or higher alkanols. In addition, it is also possible to use gelatin rectal capsules which consist of a combination of the active compounds with a base. Possible base material include for example liquid triglycerides, polyethylene glycols, or paraffin hydrocarbons.

Suitable formulations for parenteral administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension, including for example, sodium carboxymethyl cellulose, sorbitol and/or dextran. Such compositions may also comprise adjuvants such as preserving, wetting, emulsifying, and dispensing agents. They may also be sterilized, for example, by filtration through a bacteria-retaining filter, or by incorporating sterilizing agents into the compositions. They can also be manufactured in the form of sterile solid compositions which can be dissolved or suspended in sterile water, saline, or other injectable medium prior to administration.

In addition to administration with conventional carriers, active ingredients may be administered by a variety of specialized delivery drug techniques which are known to those of skill in the art, such as portable infusion pumps.

Additional formulations for administration may be made in accordance with methods and amounts known in the art as set forth in *Remington's Pharmaceutical Sciences,* 18th Ed., Wiley Publishing (1990), the disclosure of which is herein incorporated by references in its entirety.

The compositions of the present invention are administered along with a pharmaceutically acceptable carrier in an amount sufficient to prevent malarial infection and/or treat an active infection. The gallotannins of this invention have extremely low toxicity and a low degree of side effects even at high doses. The dosing range of the gallotannins will vary depending on a number of factors, such as whether it is used for prophylaxis or treatment of an active infection or malignancy, route of administration, desired dosing schedule, etc. The gallotannin compounds are preferably placed in a pharmaceutical carrier whereby the final concentration of the compound in the pharmaceutical composition is about 1-10% by weight. In general, dosage ranges of this type of pharmaceutical composition well range from about 10 to about 1000 ml per day. Otherwise, the dose of gallotannin will generally range from about 0.1-1000 mg/kg/day, with about 0.1-100 mg/kg/day being preferred. The foregoing doses may be administered as a single dose or may be divided into multiple doses for administration. The gallotannins may be administered once to several times daily.

Other drugs besides gallotannins and ellagitannins which are compatible with the carrier ingredients may also be incorporated into the pharmaceutical formulations. Such drugs may be readily ascertained by those of ordinary skill in the art and may include, for instance, antibiotics, other antivirals, antiinflammatory agents, etc.

It is understood that the present invention contemplates the use of not only the above-stated gallotannin and ellagitannins compounds themselves, but their prodrugs which metabolize to the compound and the analogues and biologically active salt forms thereof, as well as optical isomers which provide the same pharmaceutical results.

The following examples are offered to illustrate but not limit the invention. Thus, they are presented with the understanding that various formulation modifications as well as method of delivery modifications may be made and still be within the spirit of the invention.

EXAMPLE 1

Synthesis of Dimeric Gallotannin and Ellagitannins

Nuclear magnetic resonance spectra ($^1$H NMR, $^{13}$C NMR) were recorded on either 200, 300 or 360 MHz ($^1$H) spectrometers. Low resolution fast atom bombardment mass spectra (FABMS) were obtained in a 2-nitrophenyl octyl ether (NPOE) matrix or in a nitrobenzyl alcohol (NBA) matrix. High resolution fast atom bombardment mass spectra were run at the University of Texas at Austin. Circular dichroism (CD) measurements used the wavelength range 200 nm to 350 nm. Scanning at 0.5 nm intervals with an averaging time of 10.0 s at 25° C. in a 1 mm cell. The concentration of the solution(s) used was 1 mg/mL. Liquid (flash) column chromatography was carried out using 32-63 μm silica gel and the indicated solvent. Combustion analyses were performed by Midwest Microlab, Indianapolis, Ind. or Galbraith Laboratories, Knoxville, Tenn. Ether ($Et_2O$) and tetrahydrofuran (THF) were purified by distillation from sodium/benzophenone under nitrogen. Benzene, methylene chloride ($CH_2Cl_2$), methanol and toluene were distilled from $CaH_2$ under nitrogen. Moisture sensitive reactions were carried out in pre-dried glassware under an inert atmosphere of Ar. Copies of $^1H$ and $^{13}C$ NMR spectra are provided in the Supporting Information to establish purity for those compounds that were not subject to combustion analyses.

Modified Steglich Esterification Reaction: General Procedure A. A solution of the appropriate polyol (1.0 equiv), acid (1 equiv per hydroxyl), 4-(dimethylamino)pyridine DMAP) (0.5 equiv), DMAP.HCl (0.5 equiv) and 1,3-dicyclohexylcarbodiimide (DCC) (1.25 equiv per hydroxyl) in dry $CH_2Cl_2$ (0.1 M in acid) was purged with Ar and heated under Ar at reflux for 15-20 h. The solution was cooled to room temperature (rt), diluted with an equal volume of $Et_2O$, filtered through Celite and the filtrate was poured into ice-cold 1 M $H_3PO_4$. The organic layer was separated, washed with brine, dried over anhydrous $Na_2SO_4$, filtered and concentrated in vacuo. The crude product was purified by flash column chromatography using the solvents indicated.

Modified Steglich Esterification Reaction: General Procedure B. A solution of the appropriate polyol (1.0 equiv), acid (1 equiv per hydroxyl), 4-(dimethylamino)pyridine (DMAP) (0.5 equiv), DMAP.HCl (0.5 equiv) and 1,3-dicyclohexylcarbodiimide (DCC) (1.5 equiv per hydroxyl) in dry $CH_2Cl_2$ (0.1 M in acid) was purged with Ar and heated under Ar at reflux for 15-20 h. The solution was cooled to rt and filtered through Celite. The filtrate was diluted with an equal volume of EtOAc and poured into ice-cold 1 M $H_3PO_4$. The organic layer was separated, washed with brine, dried over anhydrous $Na_2SO_4$, filtered and concentrated in vacuo. The crude product was purified by flash column chromatography with the indicated eluent to furnish the desired esters.

Silyl Ether Deprotection Reaction: General Procedure C. To a solution of the appropriate t-butyldimethylsilyl (TBDMS)-protected glucose derivative (1.0 equiv) in dry THF (0.01M-0.05 M in TBDMS-protected glucose derivative) was added a solution of tetra n-butylammonium fluoride (TBAF) in THF (1.0 M solution in THF) (1.5 equiv per TBDMS group). The reaction was stirred at rt and followed by TLC (10-45 min). At the end of the indicated time period the reaction solution was carefully treated with ice-cold 1 M $H_3PO_4$, and the product extracted with $Et_2O$. The $Et_2O$ layer was separated, washed with water and then brine, dried over anhydrous $Na_2SO_4$, filtered and concentrated in vacuo. Flash column chromatography of the crude residue using the indicated solvents provided the pure product.

2,3,4,6-Tetrakis(3,4,5-tris(benzyloxy)benzoyl)-α-D-glucopyranose. 1,2,3,4,6-Pentakis(3,4,5-tris(benzyloxy)benzoyl)-β-D-glucopyranoside (7.0 g, 3.1 mmol) was dissolved in a mixture of 200 mL of dry THF and 100 mL of dry MeOH and cooled to 0° C. Ammonia gas was bubbled through the solution for 10 min. The reaction was stirred at 0° C. for 30 min and then allowed to warm to rt and stirred for a further period of 2.5 h. Removal of the solvents followed by flash column chromatography eluting with 10%, 25% and then 50%, EtOAc in hexanes furnished 4.16 g (73%) of 2,3,4,6-tetrakis(3,4,5-tris(benzyloxy)benzoyl)-D-glucopyranose as a white solid froth (mixture of α,β anomers). A portion of this product (30 mg) was further purified by preparative TLC using 10% EtOAc in benzene. IR ($CH_2Cl_2$) 3483, 1725 $cm^{-1}$; $^1H$ NMR ($CDCl_3$, 300 MHz) δ 7.42-6.64 (m, 68H), 6.23, (t, J=9.9 Hz, 1H), 5.79 (d, J=3.7 Hz, 1H), 5.70 (t, J=9.9 Hz, 1H), 5.75-4.65 (m, 27H), 4.29 (dd, J=4.3 Hz, 12.1 Hz, 1H), 3.40 (bs, 1H); $^{13}C$ NMR ($CDCl_3$, 90 MHz) δ 166.7, 165.7, 165.4, 165.1, 152.54, 152.50, 152.4, 143.1, 142.9, 142.8, 142.7, 142.6, 137.4, 137.35, 137.3, 136.6, 136.45, 136.4, 136.33, 136.3, 128.5, 128.4, 128.33, 128.2, 128.1, 128.07, 128.05, 128.0, 127.94, 127.9, 127.86, 127.8, 127.78, 127.56, 127.51, 127.4, 127.3, 124.6, 124.1, 123.9, 109.4, 109.3, 109.1, 90.4, 75.1, 75.0, 72.8, 71.2, 71.1, 70.9, 70.0, 67.6, 63.1; MS (+FAB) 1869 ($MH^+$, 0.5). Anal. Calcd for $C_{118}H_{100}O_{22}$ C, 75.80; H, 5.35; Found: C, 76.13: H, 5.45.

Methyl 3-Benzyloxy-1,2-dioxocyclohexa-3,5-diene-5-benzoate. To a solution of orthochloranii (1.97 g, 8.02 mmol) in 5 mL of $Et_2O$ cooled to −30° C. was added dropwise via an addition funnel over 6 h a solution of methyl 3-benzyloxy-4,5-dihydroxybenzoate (2.0 g, 7.3 mmol) in 115 mL of $Et_2O$. The reaction was stirred for a further 0.5 h at −30° C. and then stored at −20° C. for 20 h. The precipitated red solid was collected by filtration, washed with cold $Et_2O$ and dried on a vacuum pump to afford 1.11 g (55%) of the orthoquinone. IR ($CDCl_3$) 1727, 1671 $cm^{-1}$; $^1H$ NMR ($CDCl_3$, 300 MHz) δ 7.41-7.26 (m, 5H), 6.74 (s. 1H), 6.73 (s, $1H_1$, 6.56 (s. 2H), 3.92 (s, 3H); $^{13}C$ NMR ($CDCl_3$, 75 MHz) δ 179.9, 174.2, 164.7, 152.1, 141.3, 134.3, 128.8, 128.7, 127.7, 124.4, 107.7, 71.1, 53.4; MS (−FAB) 272 (M−, 12). Anal. Calc for $C_{15}H_{12}O_5$; C. 66.18; H. 4.41; Found: C, 65.75; H. 4.45.

Diaryl Ether. The orthoquinone (200 mg, 0.72 mmol) was dissolved in 5 mL of $CDCl_3$, $B(OAc)_3$ (136 mg. 0.72 mmol) was added and the heterogeneous mixture was heated at −2-65° C. (oil bath temperature) for 15 h at which time $^1H$ NMR analysis indicated the absence of the orthoquinone. The reaction mixture was cooled and filtered. The $B(OAc)_3$ pellet washed with cold $CH_2Cl_2$ and the filtrate and washings were evaporated to give a brown oil which was immediately stirred with NaOAc (60 mg, 0.76 mmol) in 5 mL of HOAc for 2 h. This reaction mixture was partitioned between EtOAc and water and the organic layer washed with brine and dried ($Na_2SO_4$). Concentration of the organic layer in vacuo furnished a yellow oil which was purified by flash column chromatography (−78° C., under argon) to yield 150 mg of a regioisomeric mixture of dehydrodigalloyl quinones as a yellow solid. The mixture of quinones was immediately stirred with $Na_2S_2O_4$ (180 mg, 1.08 mmol) in 8 mL of THF/2 mL of water at 0° C. for 10 min. The dark yellow reaction mixture decolorized to a pale yellow solution over this time. The reaction mixture was partitioned between EtOAc and water and the organic layer washed with brine and dried ($Na_2SO_4$). The solvent was removed in vacuo to furnish 150 mg of a white solid (regioisomeric mixture of dehydrodigalloyl ethers). The crude white solid (150 mg, 0.27 mmol) was benzylated with BnCl (126 μL, 1.10 mmol), $K_2CO_3$ (190 mg, 1.37 mmol) and KI (27 mg, 0.16 mmol) in 30 mL of refluxing acetone for 24 h. The reaction mixture was cooled, filtered through Celite and the filtrate was concentrated in vacuo to an oil which was purified by flash column chromatography using 1:1 $Et_2O$:hexanes. IR ($CH_2Cl_2$) 1718 $cm^{-1}$; $^1H$ NMR ($CDCl_3$, 300 MHz) δ 7.45-7.13 (m, 27H), 6.90 (d, J=1.8 Hz, 1H), 5.14 (s, 4H), 5.12 (s, 4H), 4.97 (s, 2H), 3.79 (s, 3H), 3.71 (s, 3H); $^{13}C$ NMR ($CDCl_3$, 90 MHz) δ 166.4, 165.2, 152.6, 149.9, 146.8, 146.5, 142.5, 141.7, 137.9, 136.8, 136.7, 136.6, 136.3, 128.61, 128.6, 128.5, 128.34, 128.3, 129.2, 128.1, 127.96, 127.9, 127.7, 127.5, 125.0, 119.8, 110.8, 109.14, 109.12, 75.6, 75.3, 75.1, 71.4, 71.2, 52.3, 52.1; MS (−FAB) 816.5 (M⁺, 100), HRFABMS. Calcd for $C_{51}H_{44}O_{10}$: 816.2934; Found: 816.2933.

3,4,5,3',4'-Pentabenzyloxydehydrodigallic Acid. A diaryl ether (0.30 g. 0.37 mmol) and lithium hydroxide hydrate (0.15 g, 3.7 mmol) in 16 mL of a 3:1 MeOH: water mixture were brought to reflux and held there with TLC monitoring for 3.5 h. The reaction mixture was cooled and the solvents removed in vacuo. Flash column chromatography on the residue using 50% EtOAc in hexanes and then 1% HOAc in EtOAc as eluents furnished 0.18 g (62%) of the diacid as a white solid. IR (KBr pellet) 2629, 1688 cm⁻¹; ¹H NMR (acetone-d₆, 300 MHz) δ 7.57-7.17 (m, 27H), 6.96 (d, J=1.7 Hz, 1H), 5.26 (s, 2H), 5.22 (s, 2H), 5.20 (s, 2H), 5.15 (s, 2H), 5.01 (s, 2H); ¹³C NMR (acetone-d₆, 50 MHz) δ 167.2, 165.9, 153.8, 150.9, 150.5, 149.0, 147.5, 147.2, 143.1, 142.5, 139.1, 138.0, 137.9, 137.7, 137.6, 129.4, 129.3, 129.2, 129.1, 128.97, 128.92, 128.9, 128.8, 128.7, 128.5, 128.3, 128.2, 126.3, 121.3, 111.7, 109.8, 76.1, 75.9, 75.6, 71.9, 71.7, 52.2, 52.0; MS (+FAB) 788.5 (M⁺, 100). HRFABMS. Calcd for $C_{49}H_{40}O_{10}$: 788.2621; Found: 788.2614.

1-O-2,3,4,6-Tetrakis(3,4,5-tris(benzyloxy)benzoyl)-α-D-glucopyranosyl Trichloroacetimidate. A solution of 2,3,4,6-tetrakis(3,4,5-tris(benzyloxy)benzoyl)-D-glucopyranose (1.0 g, 0.54 mmol) in 10 mL of dry benzene was added to degreased sodium hydride (0.014 g, 0.58 mmol), followed by addition of trichloroacetonitrile (536 µL, 5.20 mmol) and the resultant solution was stirred at rt for 18 h. The reaction was diluted with water and the product was extracted into 25 mL of EtOAc. The organic layer was separated and washed with brine and dried (Na₂SO₄). The solution was concentrated in vacuo and purified by flash column chromatography using 10%, and then 20%, EtOAc in hexanes as eluent to afford 0.90 g (84%) of 1-O-2,3,4,6-tetrakis(3,4,5-tris (benzyloxy)benzoyl)-α-D-glucopyranosyl trichloroacetimidate as a white solid. IR ((CH₂Cl₂) 3342, 1728, 1678 cm⁻¹; ¹H NMR (CDCl₃, 300 MHz) δ 8.65 (S, 1H), 7.41-7.15 (m. 68H), 6.88 (d, J=3.6 Hz, 1H), 6.21 (t. J=10.1 Hz, 1H), 5.73 (t, J=10.1 Hz. 1H), 5.54 (dd. J=3.7 Hz, 10.2 Hz, 1H), 5.13-4.88 (m, 24H), 4.82-4.65 (m. 2H), 4.32 (dd. J=5.0 Hz, 12.2 Hz, 1H); ¹³C NMR (CDCl₃, 90 MHz) δ 165.54, 165.50, 165.1, 165.0, 160.5, 152.60, 152.57, 152.51, 152.50, 143.3, 143.1, 142.8, 137.4, 137.3, 136.6, 136.5, 136.4, 136.3, 128.52, 128.50, 128.43, 128.40, 128.34, 128.30, 128.24, 128.20, 128.13, 128.11, 128.10, 128.0, 127.96, 127.9, 127.82, 127.8, 127.6, 127.52, 127.50, 124.6, 123.9, 123.5, 109.6, 109.4, 109.2, 109.1, 93.2, 90.8, 75.1, 71.3, 71.21, 71.20, 71.11, 71.1, 70.8, 69.2, 62.8; MS (+FAB) 2012 (MH⁺, 78). Anal. Calcd for $C_{120}H_{100}Cl_3NO_{22}$; C. 71.61; H. 4.97; Cl, 5.22; N, 0.70; Found: C, 71.61; H, 5.07; Cl, 5.42; N, 0.72.

1-O-3,4,5-Triacetoxybenzoyl-2,3,4,6-tetrakis(3,4,5-tris (benzyloxy)benzoyl)-β-D-glucopyranoside. A solution of 1-O-2,3,4,6-tetrakis(3,4,5-tris(benzyloxy)benzoyl)-α-D-glucopyranosyl trichloroacetimidate (170 mg, 0.08 mmol) and 3,4,5-triacetoxybenzoic acid (25 mg, 0.08 mmol) in 0.8 mL of dry toluene was brought to reflux and held there for 18 h. The reaction was cooled, the solvent was removed in vacuo, and the residue was purified by silica gel flash column chromatography using 20%, 40% and then 60%, EtOAc in hexanes as eluent to yield 60 mg (33%) of 1-O-3,4,5-triacetoxybenzoyl-2,3,4,6-tetrakis(3,4,5-tris(benzyloxy)benzoyl)-β-D-glucopyranoside as a white solid. IR (CH₂Cl₂) 1738, 1731 cm⁻¹; ¹H NMR (CDCl₃, 300 MHz) δ 7.81 (s, 1H), 7.46-7.16 (m, 69H), 6.27 (d, J=8.2 Hz, 1H), 6.05 (t, J=9.7 Hz, 1H), 5.81 (t, J=9.1 Hz, 1H), 5.69 (t, J=9.6 Hz. 1H), 5.15-4.88 (m, 24H), 4.75 (d, J=10.1 Hz, 1H), 4.42-4.32 (m, 2H), 2.27 (s, 3H), 2.25 (s, 6H); ¹³C NMR (CDCl₃, 90 MHz) δ 167.6, 166.4, 165.8, 165.2, 165.1, 162.9, 152.8, 152.73, 152.7, 143.8, 143.3, 142.7, 139.7, 137.7, 137.6, 137.5, 136.9, 136.7, 136.6, 136.5, 128.7, 128.6, 128.53, 128.50, 128.4, 128.3, 128.21, 128.20, 128.1, 128.0, 127.8, 127.79, 127.75, 126.8, 124.7, 123.8, 123.7, 123.1, 109.6, 109.5, 109.3, 109.2, 93.3, 75.33, 75.3, 73.53, 73.5, 71.4, 71.3, 71.2, 69.9, 63.4, 20.8, 20.3; MS (+FAB) 2147 (MH⁺, 25), Anal. Calcd for $C_{131}H_{110}O_{29}$: C, 73.25; H, 5.13; Found: C, 72.84; H, 5.34.

3,4-Di-tert-butyldimethylsiloxy-5-benzyloxybenzoic Acid. A solution of 3-benzyloxy-4,5-dihydroxybenzoic acid (3.00 g, 11.5 mmol) and tert-butyldimethylsilylchloride (4.34 g, 28.8 mmol) in 13 mL of DMF (minimum volume required to dissolve the reactants) was treated with N,N'-diisopropylethylamine (6.0 mL, 35 mmol). The turbid brown solution was stirred at rt for 18 h at which time TLC indicated complete absence of starting material and the presence of 3,4-di-t-butyldimethylsiloxy-5-benzyloxybenzoic acid along with 3,4-di-tert-butyldimethylsilyl(3,4-di-tert-butyldimethylsiloxy-5-benzyloxy)benzoate. The reaction mixture was treated with 20 mL of 1 M H₃PO₄ and extracted with 200 mL of Et₂O. The organic layer was separated and washed with water (10×50 mL) and then brine, dried (Na₂SO₄) and concentrated in vacuo. The residue was purified by flash column chromatography eluting with 10%, and then 25%, EtOAc in hexanes, to yield 1.53 g of the title compound as a white solid along with 3.61 g of 3,4-di-tert-butyldimethylsilyl(3,4-di-tert-butyldimethylsiloxy-5-benzyloxy)benzoate as a yellow oil. The silyl ester product was stirred in 60 mL of a 1:6:2 solution of HOAc: THF: water at rt for 2.5 h at which time TLC showed the presence of only the title compound. The reaction solution was treated with a saturated aqueous solution of sodium bicarbonate and extracted into EtOAc. The organic layer was separated and washed with water and then brine and dried (Na₂SO₄). Removal of the solvent in vacuo, followed by trituration of the residue with hexanes afforded a further 2.52 g of 3,4-di-tert-butyldimethylsiloxy-5-benzyloxybenzoic acid (4.05 g over two steps, 71%). IR (CH₂Cl₂) 3504, 1684 cm⁻¹; ¹H NMR (CDCl₃, 300 MHz) δ 7.42-7.33 (m, 7H), 5.05 (s, 2H), 0.99 (s, 9H), 0.90 (s, 9H), 0.24 (s, 6H), 0.07 (s, 6H); ¹³C NMR (CDCl₃, 75 MHz) δ 171.9, 151.2, 147.7, 136.2, 128.6, 128.4, 128.2, 116.3, 107.8, 70.9, 26.1, 25.8, 19.0, 18.6, −3.8, −4.1; MS (+FAB) 488 (MH⁺, 52). Anal. Calcd for $C_{26}H_{40}O_5Si_2$: C. 63.93; H, 8.19; Found: C, 64.17, H, 8.00.

3,4-Di-tert-butyldimethylsiloxy-5-benzyloxybenzoyl Chloride. A solution of 3,4-di-tert-butyldimethylsiloxy-5 benzyloxybenzoic acid (1.50 g, 3.07 mmol) in 30 mL of CH₂Cl₂ was treated with oxalyl chloride (295 µL, 3.38 mmol) and then a catalytic amount of DMF. The reaction was stirred at rt with monitoring by TLC. After 2h. consumption of starting material was indicated, and removal of solvents in vacuo and drying under high vacuum provided 1.55 g (100%) of product. IR (CH₂Cl₂) 1742 cm⁻¹; ¹H NMR (CDCl₃, 300 MHz) δ 7.44-7.34 (m, 7H), 5.05 (s, 2H), 0.99 (s, 9H), 0.90 (s, 9H), 0.26 (s, 6H), 0.07 (s, 6H); ¹³C NMR (CDCl₃, 75 MHz) δ 167.3, 151.3, 147.9, 143.9, 135.7, 128.8, 128.5, 128.4, 124.6, 118.2, 108.9, 71.2, 26.0, 25.7, 18.7, 18.6, −4.0, −4.1; MS (+FAB) (MH+24). HRFABMS Calcd for $C_{26}H_{39}O_4Si_2Cl$: 507.2154; Found 507.2126.

1-O-(3,4-Di-tert-butyldimethylsiloxy-5-benzyloxybenzoyl)-2,3,4,6-tetrakis(3,4,5-tris(benzyloxy)benzoyl)-β-D-glucopyranoside. Triethylamine (116 µL, 1.62 mmol) was added to a solution of 2,3,4,6-tetrakis(3,4,5-tris(benzyloxy) benzoyl)-D-glucopyranose (1.00 g, 0.54 mmol) and 3,4-ditert-butyldimethylsiloxy-5-benzyloxybenzoyl chloride (0.33 g, 0.65 mmol) in 12 mL of dry $CH_2Cl_2$ (0.05 M in alcohol) and the solution was stirred at rt for 18 h. The reaction was treated with 10 mL of 1 M HCl and extracted with 25 mL of EtOAc. The organic layer was separated and washed with water and then brine, dried ($Na_2SO_4$) and concentrated in vacuo. Flash column chromatography of the crude mixture using 10% and then 25%, EtOAc in hexanes as eluents afforded 0.96 g (76%) of 1-O-(3,4-tert-butyldimethylsiloxy-5-benzyloxybenzoyl)-2,3,4,6-tetrakis(3,4,5-tris(benzyloxy) benzoyl)-β-D-glucopyranoside as a white solid froth. IR ($CH_2Cl_2$) 1732 $cm^{-1}$; $^1H$ NMR ($CDCl_3$, 300 MHz) δ 7.48-7.13 (m, 75H), 6.28 (d, J=8.2 Hz, 1H), 6.08 (t, J=9.7 Hz, 1H), 5.88 (dd, J=9.9 Hz, 8.3 Hz, 1H), 5.78 (t, J=9.6 Hz, 1H), 5.17-4.79 (m, 27H), 4.43-4.38 (m, 2H), 0.98 (s, 9H), 0.87 (s, 9H), 0.25 (s, 3H), 0.20 (s, 3H), 0.03 (s, 3H), 0.02 (s, 3H); $^{13}C$ NMR ($CDCl_3$, 75 MHz) δ 165.6, 165.5, 164.9, 164.7, 164.4, 152.5, 152.4, 152.3, 151.1, 147.7, 143.1, 143.0, 142.9, 142.5, 142.2, 137.4, 137.3, 137.2, 136.7, 136.3, 135.9, 128.7, 128.5, 128.4, 128.35, 128.32, 128.24, 128.21, 128.1, 128.06, 128.03, 127.96, 127.90, 127.81, 127.7, 127.5, 127.4, 124.5, 123.8, 123.7, 123.66, 123.6, 120.0, 116.1, 109.3, 109.1, 107.8, 92.7, 75.1, 75.0, 73.5, 73.1, 71.1, 71.0, 70.9, 70.8, 69.8, 63.2, 26.0, 25.7, 18.5, 18.4, −3.4, −3.5; Anal. Calcd for $C_{144}H_{138}O_{26}Si$: C, 73.90: H, 5.90: Found: C, 73.91; H, 5.94.

1-O-(2-Benzyloxy-4,5-dihydroxybenzoyl)-2,3,4,6-tetrakis(3,4,5-tris(benzyloxy)benzoyl)-β-D-glucopyranoside. By use of general procedure C, 1-O-(3,4-di-tert-butyldimethylsiloxy-5-benzyloxybenzoyl)2,3,4,6-tetrakis(3,4,5-tris (benzyloxy)benzoyl)-β-D-glucopyranoside (1.10 g, 0.47 mmol) (0.02 M solution in THF) was desilylated in 45 min to provide 0.80 g (80%) of 1-O-(3-benzyloxy-4,5-dihydroxybenzoyl)-2,3,4,6-tetrakis(3,4,5-tris(benzyloxy)benzoyl)-β-D-glucopyranoside after flash column chromatography using 10%, 25% and then 50%, EtOAc in hexanes as eluents. IR ($CDCl_3$) 3534, 1732 $cm^{-1}$; $^1H$ NMR ($CDCl_3$, 300 MHz) δ 7.45-7.16 (M, 75H), 6.24 (d, J=8.1 Hz, 1H), 6.04 (t, J=9.6 Hz, 1H), 5.96 (bs, 1H), 5.83 (dd, J=9.7, 8.1 Hz, 1H), 5.73 (t, J=6 Hz, 1H), 5.50 (bs, 1H), 5.14-4.76 (m, 27H), 4.43-4.34 (m, 2H); $^{13}C$ NMR ($CDCl_3$, 75 MHz) δ 165.6, 165.5, 165.0, 164.9, 164.3, 152.59, 152.57, 152.47, 145.7, 143.7, 143.3, 143.2, 143.1, 142.6, 138.1, 137.5, 137.3, 136.4, 136.3, 135.6, 128.7, 128.6, 128.5, 128.45, 128.40, 128.3, 128.2, 128.1, 128.09, 128.06, 127.9, 127.8, 127.5, 124.6, 123.8, 123.7, 123.6, 119.9, 111.9, 109.4, 109.3, 109.2, 106.7, 92.9, 75.1, 75.08, 73.4, 73.37, 73.3, 71.4, 71.34, 71.3, 71.22, 71.2, 71.1, 69.9, 63.2. Anal. Calcd for $C_{132}H_{110}O_{26}$: C, 75.07; H, 5.21; Found: C, 74.88: H. 5.22.

1-O-(3-Benzyloxy-1,2-dioxocyclohexa-3,5-diene-5-benzoyl)-2,3,4,6-tetrakis(3,4,5-tris(benzyloxy)benzoyl)-β-D-glucopyranoside. To a solution of orthochloranii (100 mg, 0.38 mmol) in 4 mL of dry $Et_2O$ (0.1 M in orthochloranil), cooled to −30° C. was added dropwise via an addition funnel over 1.5 to a solution of 1-O-(2-benzyloxy-4,5-dihydroxybenzoyl)-2,3,4,6-tetrakis(3,4,5-tris(benzyloxy)benzoyl)-β-D-glucopyranoside (0.80 g. 0.38 mmol) in 12 mL of dry $Et_2O$ (0.03 M in diphenol). After the addition was completed, the resulting deep red solution was stirred at −30° C. for a further 3 h and then it was stored in a freezer at −20° C. for 18 h. The precipitated red solid was collected by filtration, washed with cold $Et_2O$ and dried on a vacuum pump to afford 0.53 g (66%) of product as a red amorphous powder. IR ($CDCl_3$) 1730, 1672 $cm^{-1}$; $^1H$ NMR ($CDCl_3$, 300 MHz) δ 7.45-7.17 (m, 73H), 6.79 (d, J=1.4 Hz, 1H), 6.47 (s, 1H), 6.13 (d, J=7.9 Hz, 1H), 6.03 (t. J=9.6 Hz, 1H), 5.74 (t. J=9.2 Hz, 2H), 5.15-4.85 (m, 26H), 4.79 (d, J=9.5 Hz. 1H), 4.41-4.32 (m, 2H); $^{13}C$ NMR ($CDCl_3$, 90 MHz) δ 179.6, 173.8, 165.6, 165.5, 164.9, 164.8, 162.8, 152.6, 152.5, 152.4, 143.3, 143.2, 140.1, 137.4, 137.3, 136.6, 136.3, 136.2, 134.2, 128.8, 128.6, 128.5, 128.49, 128.42, 128.3, 128.2, 128.14, 128.10, 127.99, 127.92, 127.88, 127.85, 127.83, 127.76, 127.5, 125.6, 124.4, 123.4, 123.3, 109.4, 109.3, 109.2, 106.8, 93.8, 75.1, 73.5, 72.9, 71.2, 71.18, 71.12, 71.0, 69.3, 62.8; MS (+FAB) 2109 ($MH^+$, 21). Anal. Calcd for $C_{132}H_{108}O_{26}$: C. 75.14; H, 5.12; Found: C, 74.75; H, 5.29.

Benzylated Dimer 12. The orthoquinone (100 mg, 0.047 mmol) was dissolved in 1.5 mL of ($CDCl_3$) $B(OAc)_3$ (10 mg, 0.052 mmol) was added and the heterogeneous mixture was heated at 62-65° C. (oil bath temperature) for 24 h at which time $^1H$ NMR analysis indicated absence of the orthoquinone. The reaction mixture was cooled and filtered. The residue washed with $CH_2Cl_2$ and the filtrate and washings were evaporated to give a reddish brown solid which was immediately treated with NaOAc (4 mg, 0.052 mmol) in HOAc (2 mL): THF (0.5 mL) for 2 h. This reaction mixture was partitioned between EtOAc and water. The EtOAc layer washed with brine, dried ($Na_2SO_4$) and concentrated in vacuo to yield a yellow residue. Flash column chromatography at −78° C. using 10% and then 50%, EtOAc in hexanes as eluents provided 78 mg of a yellow solid which was immediately treated with $Na_2S_2O_4$ (2 mg, 0.071 mmol) in 10 mL of 8:2 THF: water for 10 min at 0° C. The dark yellow reaction mixture decolorized to a pale yellow solution over this time. The reaction mixture was partitioned between EtOAc and water and the organic phase washed with brine, dried ($Na_2SO_4$) and concentrated in vacuo to a white solid which was dried under high vacuum. The crude white solid (78 mg, 0.018 mmol) was benzylated with benzyl chloride (9 μl. 0.07 mmol). $K_2CO_3$ (13 mg. 0.09 mmol) and KI (92 mg. 0.01 mmol) in 5 mL of refluxing acetone for 24 h. The reaction mixture was cooled, filtered through Celite and the filtrate was concentrated in vacuo to an oil which was purified by flash column chromatography using 10% and then 20%, EtOAc in hexanes as eluents to furnish 46 mg (44%, over four steps) of the perbenzylated dimeric gallotannin. IR ($CH_2Cl_2$) 1731 $cm^{-1}$; $^1H$ NMR ($CDCl_3$, 300 MHz) δ 7.64-7.05 (m, 163H), 7.04 (s, 1H), 6.23 (d, J=8.1 Hz. 1H), 6.08 (m, 2H), 5.94 (t, J=9.8 Hz. 1H), 5.84 (t, J=9.0 Hz. 1H), 5.74 (t, J=9.7 Hz. 1H), 5.70-5.62 (m. 2H), 5.15-4.70 (m. 59H), 4.58-4.31 (m, 5H); $^{13}C$ NMR ($CDCl_3$, 90 MHz) δ 169.0, 165.62, 165.6, 165.0, 164.9, 164.7, 164.2, 152.6, 152.54, 152.5, 143.3, 143.21, 143.2, 143.1, 142.7, 137.5, 137.4, 136.7, 136.5, 136.4, 136.3, 128.51, 128.5, 128.42, 128.4, 128.3, 128.2, 128.1, 128.0, 127.9, 127.8, 127.61, 127.6, 127.5, 124.6, 123.7, 123.6, 123.3, 19.5, 109.41, 109.4, 109.2, 93.0, 92.2, 75.1, 73.5, 73.3, 73.2, 71.4, 71.3, 71.2, 71.1, 71.0, 69.8, 69.7, 63.1; MS (+FAB) 4493 ($MH^+$, 35). Anal. Calcd for $C_{285}H_{236}O_{52}$: C, 76.20; H, 5.26; Found: C, 76.07; H. 5.52.

Phenolic Dimer. A solution of the dimer (32 mg, 0.007 mmol) and 10% Pd on C (6 mg, 20% by weight) in 2.5 mL of dry THF was stirred at rt under a balloon of $H_2$ at 1 atm for 20 h, purged several times with argon. Filtered twice through Celite and concentrated under reduced pressure. The resultant brown gray residue was triturated with $Et_2O$, hexanes and then benzene to yield 6 mg (50%) of the debenzylated dimeric gallotannin as a pale gray solid. $^1H$ NMR (acetone-$d_6$, 300 MHz) δ 7.42-6.93 (m, 18H), 6.78 (s, 1H), 6.32 (d, J=8.3 Hz, 1H), 6.18 (d, J=8.3 Hz, 1H), 6.09-5.87 (m, 2H), 5.69-5.39 (m, 4H), 4.56-4.25 (m, 6H); $^{13}C$ NMR (acetone-$d_6$, 90 MHz) δ 169.4, 166.4, 165.9, 165.8, 165.6, 165.5, 164.9, 146.0, 145.8, 139.3, 139.1, 129.3, 129.2, 128.5, 121.5, 120.7, 120.6, 120.0, 110.4, 110.3, 110.1, 93.4, 92.9, 74.0, 73.3, 71.8, 69.3, 69.2, 66.9, 62.8; MS (+FAB) 1879 (MH+, 22), 1901 (M+Na+, 36). HRFABMS Calcd for $C_{82}H_{62}O_{52}$: 1878.2207; Found: 1878.2190: Calcd for $C_{82}H_{62}O_{52}Na$: 1901.2105; Found: 1901.2085.

2-Nitrobenzyl 4.6-O-Benzylidene-2,3-bis(3,4,5-tris(benzyloxy)benzoyl)-β-D-glucopyranoside. By use of general procedure A, 2-nitrobenzyl 4.6-O-benzylidene-β-D-glucopyranoside (5.20 g, 12.9 mmol), and 3,4,5-tribenzyloxybenzoic acid (11.4 g, 25.8 mmol) were coupled to afford 12.6 g (78%) of 2-nitrobenzyl 4.6-O-benzylidene-2,3-bis(3,4,5-tris(benzyloxy)benzoyl)-β-D-glucopyranoside as a white solid foam following flash column chromatography using 10% and then 20%. EtOAc in hexanes as eluent. IR (CDCl₃) 1728 cm⁻¹; ¹H NMR (CDCl₃, 300 MHz) δ 8.06-8.03 (m, 1H), 7.67-7.64 (m, 1H), 7.44-7.17 (m, 41H), 5.78 (t, J=9.5 Hz. 1H), 5.60-5.55 (m, 2H), 5.33 (d, J=15.4 Hz. 1H), 5.12-4.99 (m, 13H), 4.94 (d, J=7.8 Hz, 1H), 4.49 (dd, J=10.3 Hz, 4.6 Hz, 1H), 3.99-3.87 (m, 2H), 3.77 (dd, J=9.4 Hz, 4.7 Hz, 2H); ¹³C NMR (CDCl₃, 75 MHz) δ 165.2, 164.9, 152.5, 152.4, 146.6, 142.8, 142.7, 137.3, 136.6, 136.5, 136.4, 133.8, 133.7, 129.1, 128.4, 128.3, 128.2, 128.1, 128.06, 128.0, 127.9, 127.8, 127.5, 127.4, 126.1, 124.3, 124.0, 109.3, 109.2, 101.1, 101.3, 78.7, 75.1, 72.1, 72.2, 71.2, 68.5, 68.1, 66.8; MS (+FAB) 1248 (MH+, 22), Anal. Calcd for $C_{76}H_{65}NO_{16}$: C, 73.13; H, 5.21; N, 1.12; Found: C, 73.11; H, 5.17; N, 0.92.

2-Nitrobenzyl 2,3-Bis(3,4,5-tris(benzyloxy)benzoyl)-β-D-glucopyranoside. A solution of 2-nitrobenzyl 4.6-O-benzylidene-2,3-bis(3,4,5-tris(benzyloxy)benzoyl)-β-D-glucopyranoside (1.4 g, 1.1 mmol) and iodine (0.28 g, 1.1 mmol) in 17 mL of dry $CH_3OH$ and 17 mL of dry $CH_2Cl_2$ was heated at reflux under Ar for 48 h. The solution was cooled to rt. Treated with a saturated aqueous solution of $Na_2S_2O_3$ and extracted with EtOAc. The organic layer was separated, washed with water and then brine, dried ($Na_2SO_4$) and concentrated in vacuo. Flash column chromatography using 30% and then 50%, EtOAc in benzene provided 1.10 g (84%) of 2-nitrobenzyl 2,3-bis(3,4,5-tris(benzyloxy)benzoyl)-β-D-glucopyranoside as a white solid froth. IR ($CH_2Cl_2$) 1726 cm⁻¹; ¹H NMR (CDCl₃, 300 MHz) δ 8.04-8.01 (m, 1H), 7.64-7.60 (m, 1H), 7.43-7.17 (m, 36H), 5.53 (dd, J=9.7 Hz. 8.0 Hz. 1H), 5.33-5.27 (m, 2H), 5.13-4.83 (m, 13H), 4.96 (d, J=8.0 Hz. 1H), 4.91-4.84 (m, 1H), 4.04-3.93 (m, 3H), 3.64-3.60 (m, 1H), 3.56 (bs. 1H); ¹³C NMR (CDCl₃, 75 MHz) δ 167.5, 165.1, 152.6, 146.8, 137.3, 136.4, 133.8, 133.7, 128.52, 128.5, 128.44, 128.4, 128.14, 128.1, 127.99, 127.91, 127.6, 127.53, 127.5, 124.7, 124.0, 123.5, 109.3, 109.2, 100.7, 78.1, 75.1, 71.6, 71.2, 71.1, 71.0, 69.9, 68.1, 62.1; MS (+FAB) 1159 (M+, 18). Anal. Calcd for $C_{69}H_{61}NO_{16}$; C, 71.44; H. 5.26; N. 1.21; Found: C. 71.30; H. 5.45; N, 1.18.

2-Nitrobenzyl 4,6-Bis(3-tert-butyldimethylsiloxy-4,5-diphenylmethyl-enedioxybenzoyl)-2,3-bis(3,4,5-tris(benzyloxy)benzoyl)-β-D-glucopyranoside. By use of general procedure B, 2-nitrobenzyl 2,3-bis(3,4,5-tris(benzyloxy)benzoyl)-β-D-glucopyranoside (2.10 g, 1.81 mmol) was coupled with 3-tert-butyldimethylsiloxy-4,5-diphenylmethylenedioxybenzoic acid (1.62 g, 3.62 mmol) to afford 2.99 g (80%) of 2-nitrobenzyl 4,6-bis(3-tert-butyldimethylsiloxy-4,5-diphenylmethylenedioxybenzoyl)-2,3-bis(3,4,5-tris(benzyloxy)benzoyl)-β-D-glucopyranoside as a white solid foam following flash column chromatography using 10%, and then 20%. EtOAc in hexanes as eluent. IR ($CH_2Cl_2$) 1729 cm⁻¹; ¹H NMR (CDCl₃, 75 MHz) δ 8.05 (d, J=1.3 Hz, 1H), 7.98 (d, J=4 Hz, 1H), 7.70-7.15 (m, 60H), 5.84 (t, J=9.7 Hz, 1H), 5.67-5.56 (m, 2H), 5.31 (d, J=15.2 Hz, 2H), 5.13-4.89 (m, 14H), 4.64, (d, J=10.6 Hz, 1H), 4.38-4.32 (m, 1H), 4.15-4.12 (m, 1H), 0.99 (s, 9H), 0.96 (s, 9H) 0.19 (s, 6H), 0.18 (s, 6H); ¹³C NMR (CDCl₃, 75 MHz) δ 165.6, 165.3, 164.9, 164.4, 152.5, 148.6, 146.8, 142.8, 142.0, 141.7, 139.9, 139.6, 138.6, 137.4, 136.5, 133.7, 129.2, 128.9, 128.4, 128.3, 128.1, 128.0, 127.6, 127.5, 126.2, 124.6, 124.2, 124.0, 123.5, 122.5, 119.1, 118.8, 118.2, 109.3, 109.1, 104.1, 100.1, 75.1, 75.0, 73.3, 72.8, 72.3, 71.2, 71.1, 68.9, 68.3, 62.5, 26.05, 26.04, 18.3, 18.2, −4.0; MS (+FAB) 2020 (MH+, 23). Anal. Calcd for $Cl_{21}H_{113}NO_{24}Si_2$: C, 71.92; H. 5.59; N, 0.69; Found: C, 72.16; H, 5.80: N, 0.58.

2-Nitrobenzyl 4,6-Bis(3,4-diphenylmethylenedioxy-5-hydroxybenzoyl)-2,3-bis(3,4,5-tris(benzyloxy)benzoyl)-β-D-glucopyranoside. By use of general procedure C, 2-nitrobenzyl 4,6-bis(3-tert-butyldimethylsiloxy-4,5-diphenylmethylenedioxy-benzoyl)2,3-bis(3,4,5-tris(benzyloxy)benzoyl)-β-D-glucopyranoside (2.64 g, 1.31 mmol) (0.05 M solution in THF) was desilylated in 35 min to afford 1.80 g (77%) of 2-nitrobenzyl 4,6-bis(3,4-diphenylmethylenedioxy-5-hydroxybenzoyl)-2,3-bis(3,4,5-tris(benzyloxy)benzoyl)-β-D-glucopyranoside following flash column chromatography using 10%, and then 40%, EtOAc in hexanes as eluent. IR ($CH_2Cl_2$) 3554, 1729 cm⁻¹; ¹H NMR (CDCl₃, 300 MHz) δ 8.05-8.02 (m, 1H), 7.68 (d, J=7.8 Hz, 1H), 7.68-7.08 (m, 60H), 6.26 (bs, 1H), 5.83 (t, J=9.6 Hz, 1H), 5.63-5.52 (m, 2H), 5.42 (d, J=15.8 Hz, 1H), 5.14-4.87 (m, 14H), 4.62 (d, J=12.1 Hz, 4H), 4.31-4.25 (m, 1H), 4.11-4.06 (m, 1H); ¹³C NMR (CDCl₃, 75 MHz) δ 165.6, 165.4, 164.9, 164.5, 152.5, 148.5, 148.3, 146.3, 142.8, 139.6, 139.2, 138, 138.7, 138.6, 137.4, 137.3, 135.5, 134.4, 134.2, 129.4, 129.3, 128.5, 128.4, 128.35, 128.31, 128.3, 128.2, 128.1, 127.99, 127.90, 127.8, 127.6, 127.5, 126.3, 126.2, 124.8, 124.1, 123.7, 123.6, 122.7, 118.9, 118.7, 114.4, 113.6, 109.3, 109.2, 103.6, 100.7, 75.1, 73.2, 72.7, 72.3, 71.2, 71.1, 69.5, 67.7, 63.2; MS (+FAB) 1792 (MH+, 40). Anal. Calcd for $C_{109}H_{85}NO_{24}$: C, 73.03; H, 4.75; N, 0,78: Found: C, 73.23; H, 4.88; N, 0.55.

Regioisomeric Mixture of 2-Nitrobenzyl 4,6-(3,4-Diphenylmethylenedioxy-5-hydroxy-3',4'-diphenylmethylenedioxy-5'hydroxy)diphenoyl-2,3-bis(3,4,5-tris(benzyloxy)benzoyl)-β-D-glucopyranoside. A solution of $Pb(OAc)_4$ (0.49 g, 1.10 mmol) in 5 mL of dry $CH_2Cl_2$ was added dropwise to a cooled (−30° C.) deoxygenated solution of 2-nitrobenzyl 4,6-bis(3,4-diphenylmethylenedioxy-5-hydroxybenzoyl)-2,3-bis(3,4,5-tris(benzyloxy)benzoyl)-β-D-glucopyranoside (1.80 g, 1.0 mmol) and pyridine (326 μL, 4.0 mmol) in 180 mL of dry $CH_2Cl_2$ (0.005 M in bis phenol) over 30 min. The deep orange solution was stirred at −30° C. for a further 1 h, treated with 100 mL of a saturated aqueous solution of $NaHCO_3$ and extracted with 250 mL of EtOAc. The organic layer washed with 75 mL of 1 M $H_3PO_4$ and then brine, and dried ($Na_2SO_4$). Concentration in vacuo, followed by purification of the resultant yellow residue by silica gel chromatography using 10%, 20% and then 35%. EtOAc in hexanes furnished 1.21 g (67%) of a mixture of three regioisomers as a yellow solid. IR ($CH_2Cl_2$) 1747.1731 cm⁻¹; ¹H NMR (CDCl₃, 300 MHz) δ 8.05-8.02 (m, 1H), 7.98-7.00 (m, 57H), 6.79-6.71 (M, 2H), 5.66-5.56 (m, 2H), 5.48-5.29 (m, 2H), 5.18-4.79 (m, 15H), 4.14-3.90 (m, 2H); MS (+FAB) 1790 (MH+, 80). Anal. Calcd for $C_{109}H_{83}NO_{24}$; C, 73.11; H, 4.64; N, 0.78; Found: C, 72.89; H, 4.88; N, 0.67.

2-Nitrobenzyl 4,6-(3,4,5,3',4',5'-Hexabenzyloxy)diphenoyl-2,3-bis(3,4,5-tris(benzyloxy)benzoyl)-β-D-glucopyranoside. 2-Nitrobenzyl 4,6-(3,4-diphenylmethylenedioxy-5-hydroxy-3',4'-diphenylmethylenedioxy-5'-hydroxy)

diphenoyl-2,3-bis(3,4,5-tris(benzyloxy)benzoyl)-β-D-glucopyranoside (1.30 g, 0.73 mmol) was brought to reflux in 75 mL of 80% HOAc and held there for 16 h. The solvent was removed to yield an oil which was triturated with hexanes to afford 1.10 g of crude 2-nitrobenzyl 4,6-(3,4,5,3',4',5'-hexahydroxy)diphenoyl-2,3-bis(3,4,5-tris(benzyloxy)benzoyl)-β-D-glucopyranoside as a yellow solid. The crude hexahydroxy compound (1.10 g, 0.75 mmol) and sodium hydride (0.22 g, 9.03 mmol) (60% suspension in oil) were stirred in 10 mL of dry THF at 0° C. for 10 min. After addition of benzyl bromide (0.81 mL. 6.8 mmol) and then tetra-n-butylammonium iodide (TBAI) (0.25 g, 0.68 mmol), the resulting turbid brown suspension was allowed to warm to rt over 30 min and stirred for a further 18 h at rt. The reaction was diluted with water and extracted with $Et_2O$. The organic layer was separated, washed with water and then brine, dried ($Na_2SO_4$), and concentrated to a yellow oil. Purification of this residue by flash column chromatography using 10%, 20% and then 30%, EtOAc in hexanes as eluents yielded 0.75 g (50%) of 2-nitrobenzyl 4,6-(3,4,5,3',4',5'-hexabenzyloxy)diphenoyl-2,3-bis(3,4,5-tris(benzyloxy)benzoyl)-β-D glucopyranoside as a white solid froth. IR ($CH_2Cl_2$) 1728 $cm^{-1}$; $^1H$ NMR ($CDCl_3$, 300 MHz) δ 8.08-8.05 (m, 1H), 7.70-7.67, (m, 1H), 7.49-6.85 (m, 68H), 5.73-5.61 (m, 2H), 5.47-5.34 (m, 2H), 5.23-4.73 (m, 27H), 4.22-4.17 (m, 1H), 4.11 (d, J=13.2 Hz. 1H); $^{13}C$ NMR ($CDCl_3$, 90 MHz) δ 167.4, 166.7, 165.9, 164.9, 152.7, 152.6, 152.5, 152.3, 152.2, 146.8, 144.7, 144.5, 143.1, 137.7, 137.6, 137.5, 137.4, 16.5, 136.4, 133.9, 133.7, 128.7, 128, 128.5, 128.46, 128.39, 128.36, 128.33, 128.26, 128.22, 128.1, 128.02, 128.01, 127.9, 127.87, 127.84, 127.7, 127.6, 127.56, 127.50, 127.4, 127.3, 127.2, 126.7, 124.6, 124.1, 123.9, 123.6, 123.4, 109.5, 108.0, 107.9, 101.3, 75.4, 75.1, 75.0, 74.9, 73.4, 72.4, 71.9, 71.3, 71.2, 71.1, 70.3, 68.1, 67.9, 63.1; MS (+FAB) 2002 ($MH^+$, 56); Anal. Calcd for $C_{125}H_{103}NO_{24}$; C, 74.96; H, 5.15; N, 0.69; Found: C, 74.73; H, 5.17; N, 0.64.

4,6-(3,4,5,3',4',5'-Hexabenzyloxy)diphenoyl-2,3-bis(3,4,5-tris(benzyl-oxy)benzoyl)-α-D-glucopyranose. 2-Nitrobenzyl 4,6-(3,4,5,3',4',5'-hexabenzyloxy)diphenoyl-2,3-bis(3,4,5-tris(benzyloxy)benzoyl)-β-D-glucopyranoside (100 mg, 0.05 mmol) was dissolved in a mixture of 6 mL of THF, 6 mL of EtOH, and 1 mL of distilled water and irradiated in a Pyrex tube suspended in a Rayonet photochemical apparatus at 350 nm for 7.5 h. Removal of solvents in vacuo yielded an oil which upon flash column chromatography using 10%, and then 20%, EtOAc in hexanes as eluents provided 62 mg (66%) of 4,6-(3,4,5,3',4',5'-hexabenzyloxy)diphenoyl-2,3-bis(3,4,5-tris(benzyloxy)benzoyl)-D-glucopyranose as a white solid (mixture of α,β anomers). A sample (25 mg) of this product was further purified by preparative thin layer chromatography using 5% EtOAc in benzene as eluent to provide 15 mg of product. IR ($CH_2Cl_2$) 3512, 1725 $cm^{-1}$; $^1H$ NMR ($CDCl_3$, 300 MHz) δ 7.47-6.83 (m, 66H), 6.05 (t, J=10.1 Hz, 1H), 5.72 (d, J=3.7 Hz, 1H), 5.40-4.69 (m, 28H), 3.94 (d, J=12.9 Hz. 1H), 3.37 (bs, 1H); $^{13}C$ NMR ($CDCl_3$, 90 MHz) δ 167.7, 167.0, 165.9, 165.3, 152.64, 152.6, 152.54, 152.52, 152.3, 152.2, 144.7, 144.3, 142.9, 142.8, 137.7, 137.6, 137.5, 137.4, 137.3, 136.5, 136.42, 136.4, 136.31, 136.3, 128.8, 128.5, 128.4, 128.4, 128.32, 128.3, 128.2, 128.1, 128.0, 127.97, 127.91, 127.88, 127.83, 127.7, 127.6, 127.56, 127.53, 127.3, 127.6, 127.56, 127.53, 127.3, 124.1, 123.9, 123.7, 123.4, 109.3, 108.0, 107.8, 90.7, 75.5, 75.4, 75.1, 75.0, 74.8, 73.1, 71.2, 71.1, 71.0, 70.9, 70.4, 67.0, 63.5; MS (+FAB) 1867 ($MH^+$, 16); HRMS Calcd for $C_{118}H_{98}O_{22}$ 1866.6549; Found 1866.6528.

4,6-(3,4,5,3',4',5'-Hexabenzyloxy)diphenoyl-1,2,3-tris(3,4,5-tris(benzyloxy)benzoyl)-β-D-glucopyranoside. A solution of 4,6-(3,4,5,3',4',5'-hexabenzyloxy)diphenoyl-2,3-bis(3,4,5-tribenzyloxybenzoyl)-D-glucopyranose (100 mg, 0.05 mmol) in 5 mL of benzene was added to a flask containing a solution of the 3,4,5-tribenzyloxybenzoyl chloride (30 mg, 0.06 mmol) and triethylamine (22 μL. 0.15 mmol) in 2 mL of benzene. The reaction mixture was stirred at rt for 18 h. The solution was then treated with 5 mL of ice cold 1M HCl and extracted with 15 mL of EtOAc. The organic layer was washed with water and then brine and dried ($Na_2SO_4$). Removal of solvents in vacuo furnished a white solid which was purified by flash column chromatography using 10% EtOAc in hexanes, and then 25% EtOAc in hexanes, as eluents to provide 50 mg (41%) of 4,6-(3,4,5,3',4',5'-hexabenzyloxy)diphenoyl-1,2,3-tris(3,4,5-tribenzyloxy)benzoyl-β-D-glucopyranoside as a white solid. IR ($CDCl_3$) 1735 $cm^{-1}$; $^1H$ NMR ($CDCl_3$, 300 MHz) β 7.50-6.84 (m, 83H), 6.10 (d, J=7.6 Hz, 1H), 5.82 (m, 2H), 5.51 (t, J=9.7 Hz, 1H), 5.42 (dd, J=6.4, 13.3 Hz.), 5.21-4.72 (m, 30H), 4.38 (dd, J=6.0, 9.9 Hz, 1H), 4.10 (d, J=12.9 Hz, 1H); $^{13}C$ NMR ($CDCl_3$, 90 MHz) δ 167.4, 166.8, 165.7, 164.8, 164.2, 152.7, 152.61, 152.6, 152.5, 152.3, 152.2, 144.8, 144.4, 143.3, 143.2, 143.1, 137.64, 137.6, 137.5, 137.34, 137.31, 137.3, 136.44, 136.4, 136.3, 128.6, 128.42, 128.4, 128.38, 128.3, 128.22, 128.2, 128.03, 128.0, 127.97, 127.91, 127.9, 127.7, 127.6, 127.5, 127.3, 123.8, 123.6, 123.4, 123.2, 109.5, 109.4, 109.3, 107.91, 107.9, 93.1, 75.5, 75.4, 75.1, 75.0, 74.8, 73.1, 72.7, 71.6, 71.2, 70.1, 63.0; MS (+FAB) 2288 ($M^+$, 20), Anal. Calcd for $C_{146}H_{120}O_{26}$; C. 76.57; H, 5.24; Found: C, 76.38, H, 5.40.

Tellimagrandin II. A solution of 4,6-(3,4,5,3',4',5'-hexabenzyloxy)diphenoyl-1,2,3-tris(3,4,5-tris(benzyloxy)benzoyl)-β-D-glucopyranoside (26 mg, 0.01 mmol) and 10% Pd/C (5 mg, 20% by weight of starting material) in 1.5 mL of THF was purged with hydrogen six times and stirred at rt under a balloon of hydrogen for 18 h. The reaction mixture was then purged with argon twice and filtered twice through Celite. The filtrate was concentrated to a dark brown solid which was triturated several times with hexanes and diethyl ether and dried to furnish 3 mg (30%) of tellimagrandin II as a gray solid. $^1H$ NMR (acetone-$d_6$, 200 MHz) δ 7.11 (s, 2H), 6.99 (s, 2H), 6.96 (s, 2H), 6.65 (s, 1H), 6.45 (s, 1H), 6.20 (d, J=8.3 Hz. 1H), 5.84 (t, J=9.7 Hz. 1H), 5.59 (t, J=8.9 Hz. 1H), 5.37 (dd, J=6.4, 13.4 Hz, 1H), 5.21 (t, J=10 Hz. 1H), 4.54 (dd, J=5.9, 9.9 Hz, 1H), 3.88 (d, J=14 Hz, 1H); $^{13}C$ NMR (acetone-$d_6$, 90 MHz) δ 168.0, 167.6, 166.2, 165.4, 165.0, 146.1, 145.9, 145.8, 145.3, 144.5, 139.8, 139.3, 139.1, 136.6, 126.6, 126.0, 120.6, 120.5, 119.9, 115.5, 110.4, 110.2, 110.1, 108.3, 107.9, 93.7, 73.2, 73.1, 71.7, 70.7, 63.1; MS (+FAB) 938 ($M^+$, 56), 937 (M−1, 95); CD(MeOH) 235 nm. +31.7, 261 nm, −7.5, 281.5 nm, +7.7; HRMS Calcd. for $C_{41}H_{29}O_{26}$: 937.0947; Found: 937.0943.

EXAMPLE 2

Production of TNF-α and IL-1β from hPBMC's Following Exposure to Dimeric Gallotannins and Ellagitannins Authentic samples of agrimoniin and coriariin A were supplied by Professor Yoshida (Okayama University, Japan). Dimeric gallotannin (analog of coriariin A) and β-D-PGG were synthesized as described. LPS (*E. coli* 055:B5 phenol extract, MW range 50-100 KD). Ficoll-Histopaque (ρ=1.077 g/mL), Fetal Bovine Serum, sterile, hybridoma tested (FCS), gentamicin 10 mg/mL. L-glutamine, 200 mM. Dextran B-512 *Leuconostoc* Av M.W. 580000, and Trypan Blue stain were purchased from Sigma. Hanks Buffer Saline Solution 1×, with phenol red, mediatech (HBSS) and RPMI 1640 1×, mediatech were purchased from Fisher Scientific, Human IL-1β and TNF-α Enzyme Linked ImmunoSorbent Assay (ELISA) kits were purchased from R and D Systems, Minneapolis, Minn. Fresh heparinized blood was obtained from health human subjects (ages 20-34).

Dose-Response Data: General Procedure. H-PBMC's were isolated by reported procedures (10. 18). The cells counted and the viability was determined by Trypan Blue exclusion (typically, viability exceeded 95%). The concentration of the cells in the 0.5 mL wells was adjusted to $1\times10^6$ cells/well by diluting with the required amount of RPMI.

The appropriate amount of a tannin (or LPS) stock solution in HBSS was added to each well to furnish the concentration values reported in the Figures. Each concentration value was run in triplicate, and blank runs ensured that (bacterial) contamination did not complicate the experiments. The culture plates were incubated in a 5% $CO_2$, 37° C. humidified incubator for the indicated time. At the end of the time interval, 450 μL of the culture supernatant from each well was harvested, after centrifugation at 400 g, 25° C., 10 min. with brake, and stored at −78° C. pending ELISA analysis for the cytokine(s). The ELISA assays were conducted per the manufacturer's instructions using standard calibration curves to calculate cytokine concentration from observed absorbance readings. The cytokine values reported are averages of three runs±SE.

Results

The dimeric antitumor ellagitannins coriariin A and agrimoniin, the monomeric gallotannin β-D-pentagalloylglucose (β-D-PGG) and the dimeric gallotannin of this invention were all examined in this study. The dimeric gallotannin is an analog of coriariin A and is identical to the parent ellagitannin except that the galloyl rings at O(4) and O(6) are not joined in a hexahydroxydiphenoyl (HHDP) linkage. h-PBMC's were incubated with the compound under investigation for the indicated length of time and the amounts of both IL-1β and, independently, TNF-α, present in the culture supernatants was determined using commercially available ELISA kits. In each case, LPS was used as a positive control while untreated cells were reserved as negative controls.

Initial trials with the natural products were pursued under conditions described by Miyamoto, After a 4 h treatment with 28 μM agrimoniin, h-PBMC's secreted ca. 1 ng/mL of IL-1β above blank (FIG. 1), a comparable result to that reported earlier (ca. 1.2 ng/mL at 20 μM agrimoniin). Using these same experimental conditions to facilitate comparison with the prior studies from Hokuriku University, coriariin A also demonstrated significant IL-1β inducing ability, perhaps twice that of agrimoniin on a molar basis (FIG. 1). Additional scouting experiments using a qualitative L929 murine fibroblast lysis assay (19,20) with both coriariin A and agrimoniin revealed that these dimeric ellagitannins also promoted release of TNF-α in substantial amounts. This indirect measure of TNF-α levels in the h-PBMC supernatant provided the first evidence which implicated this cytokine in tannin-mediated antitumor activity and encouraged a more quantitative assessment of the TNF-α liberating capacity of agrimoniin and the related species as described below.

Figure 2:
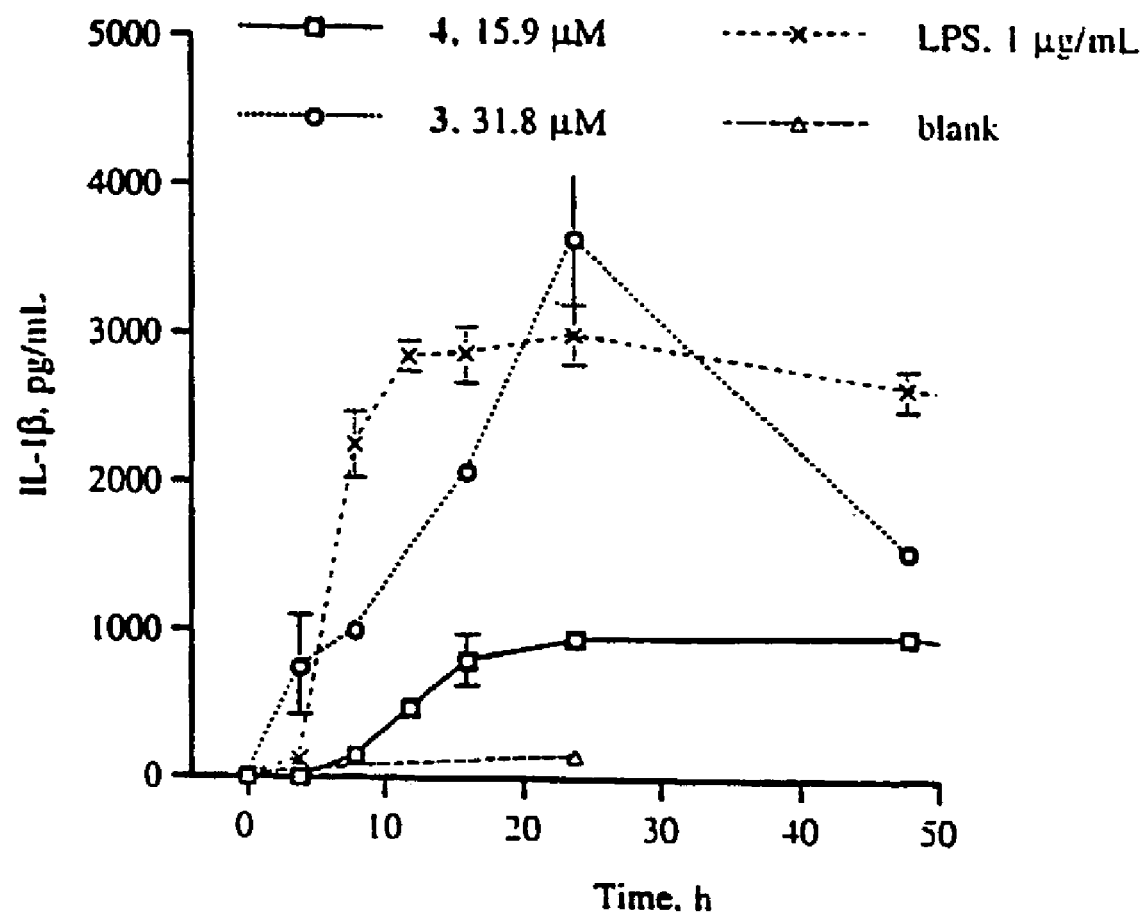
FIG. 2 shows the time course of IL-1β release from h-PBMC's stimulated by fixed concentrations of β-D-PGG, the dimeric gallotannin, and LPS.
Figure 3:
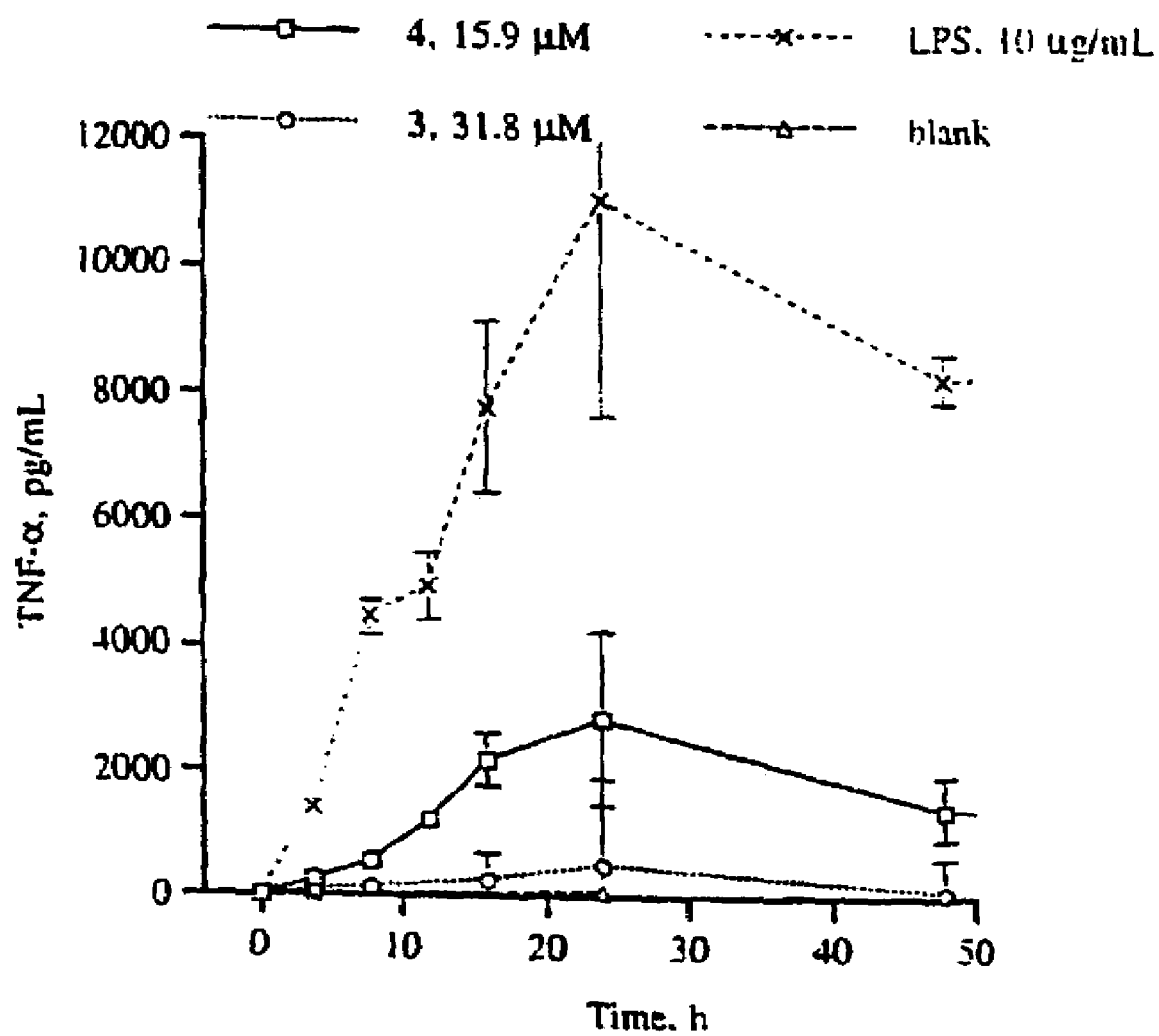
FIG. 3 shows the time course of TNF-α release from h-PBMC's stimulated by fixed concentrations of β-D-PGG, the dimeric gallotannin, and LPS.
Figure 4:
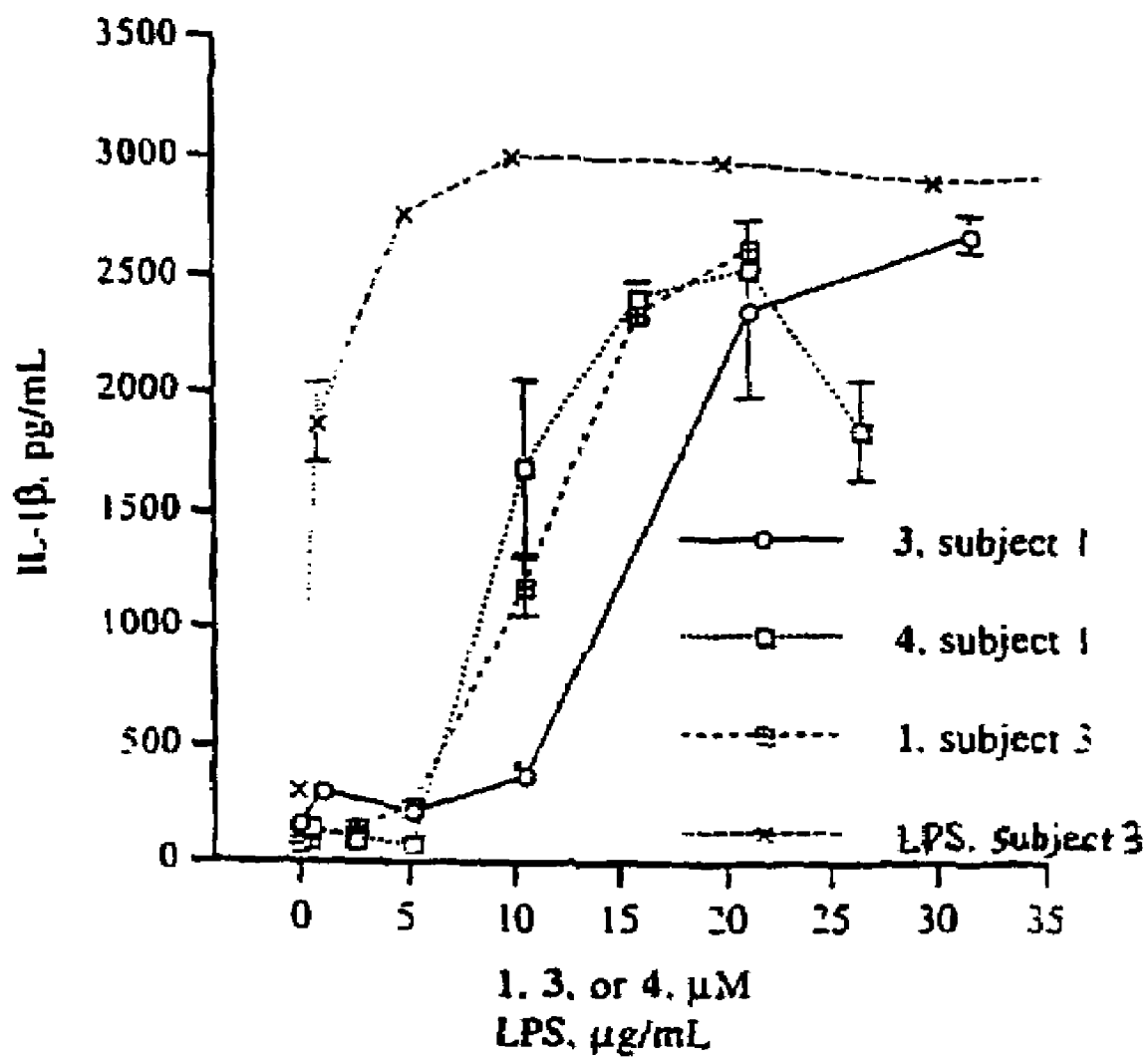
FIG. 4 shows IL-1β release from subject 1's h-PBMC's upon exposure to varying concentrations of β-D-PGG (24 h), the dimeric gallotannin (24 h), coriariin A (4 h), and LPS (4 h).
Figure 5:
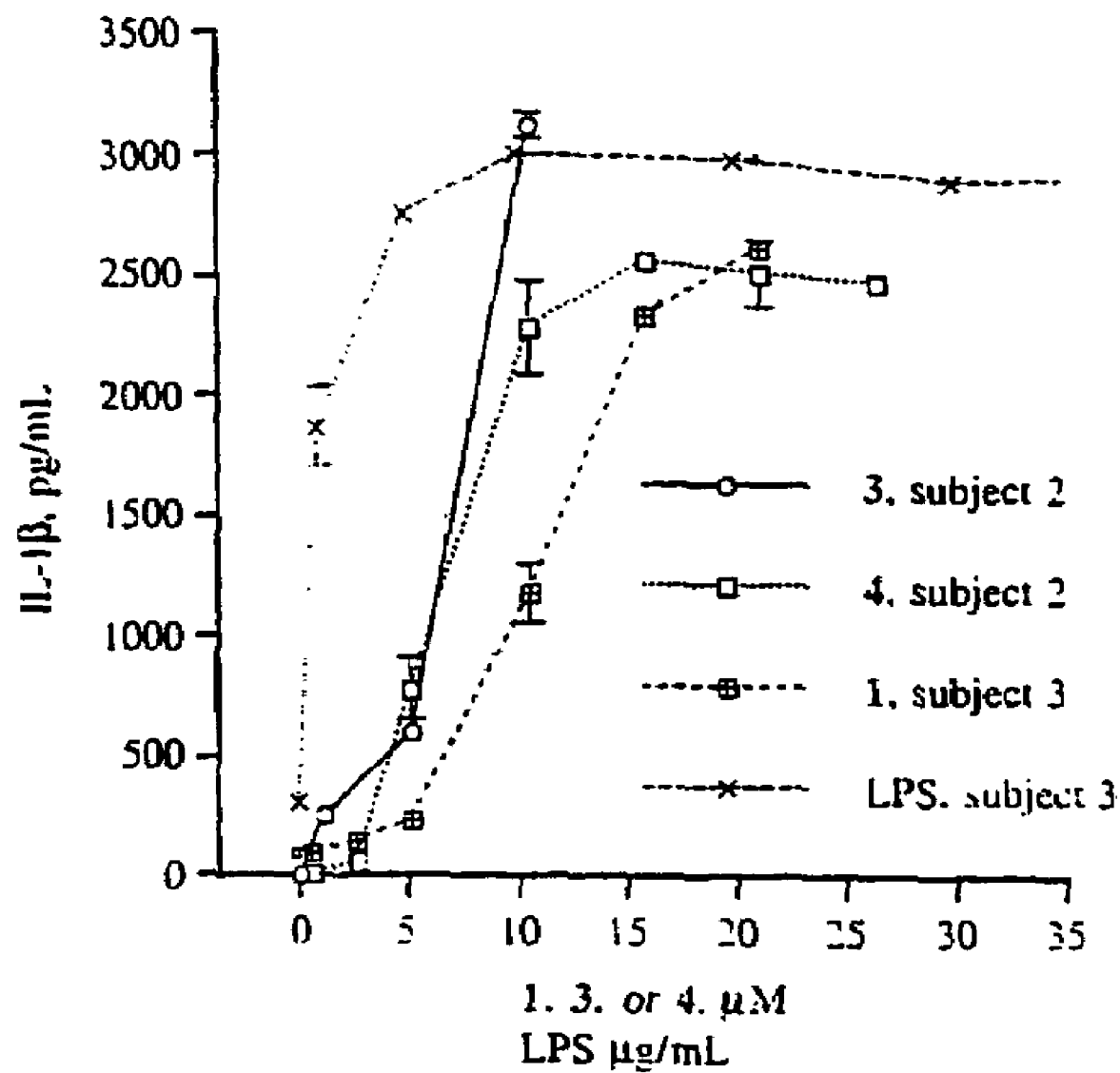
FIG. 5 shows IL-1β release from subject 2's h-PBMC's upon exposure to varying concentrations of β-D-PGG (24 h), the dimeric gallotannin (24 h), coriariin A (4 h), and LPS (4 h).
Figure 6:
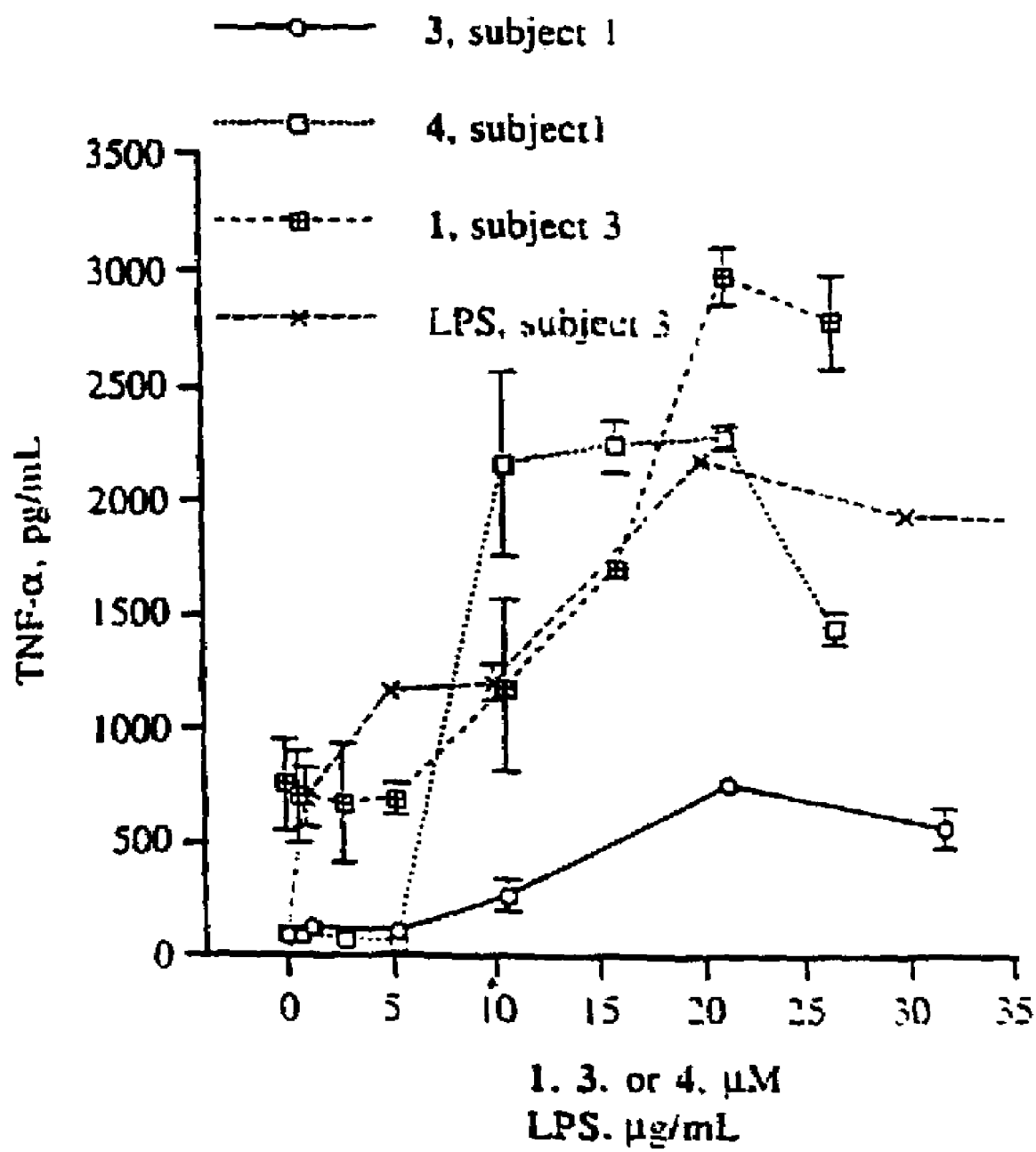
FIG. 6 shows TNF-α release from subject 1's h-PBMC's upon exposure to varying concentrations of β-D-PGG (24 h), the dimeric gallotannin (24 h), coriariin A (4 h), and LPS (4 h).
Figure 7:
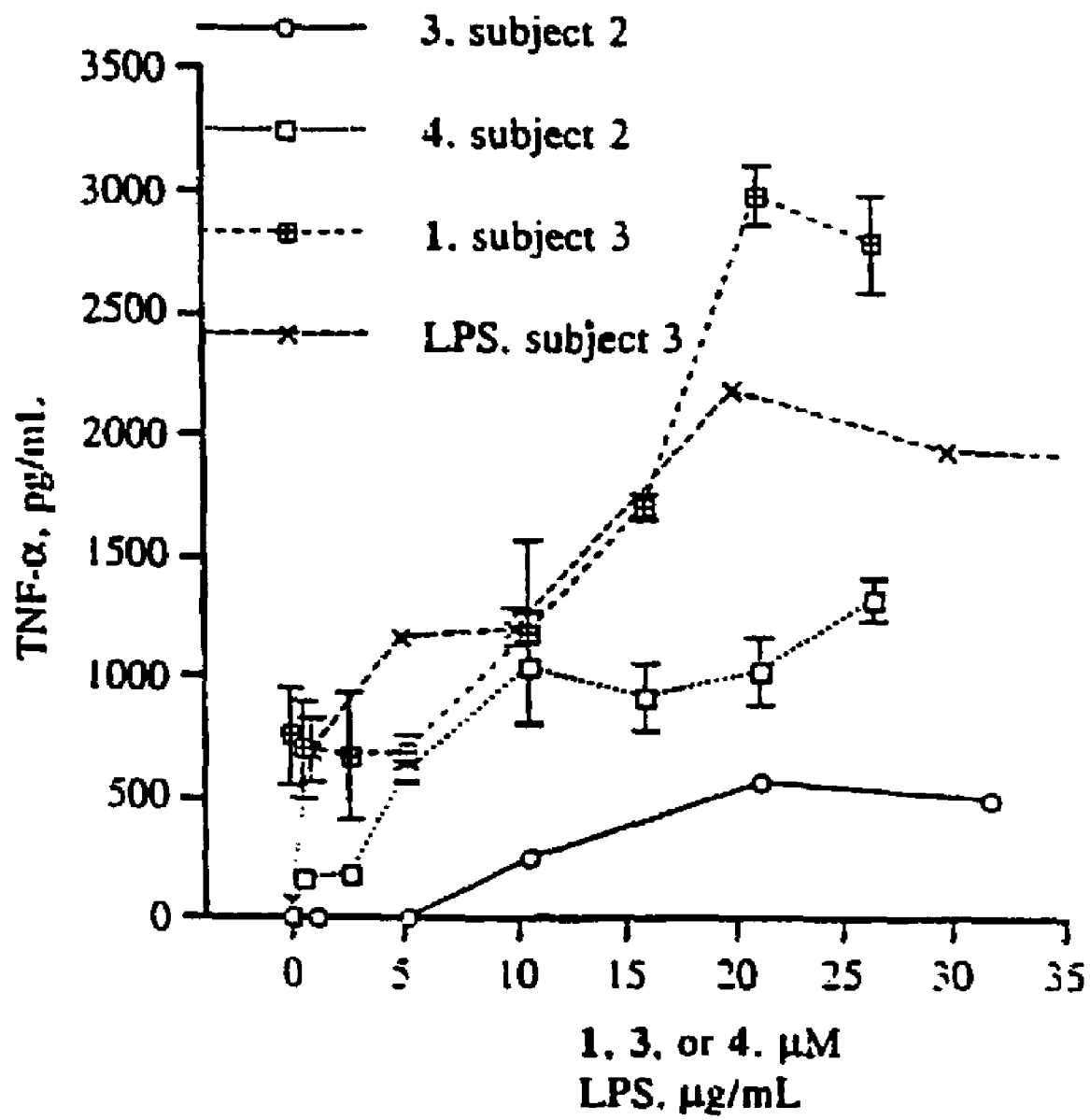
FIG. 7 shows TNF-α release from subject 2's h-PBMC's upon exposure to varying concentrations of β-D-PGG (24 h), the dimeric gallotannin (24 h), coriariin A (4 h), and LPS (4 h).

The time course for agrimoniin-mediated IL-1β secretion from h-PBMC's was delineated by Miyamoto. Significant release of this cytokine was evident after a 4 h treatment, with maximal secretion at ca. 24 h. In contrast, the kinetics of both IL-1β and TNF-α release from the h-PBMC's used in this study upon treatment with β-D-PGG or the dimeric gallotannin followed measurably different profiles (FIGS. 2 and 3). In all cases, a maximum value of cytokine discharge was observed at ca. 24 h (similar to Miyamoto's system), but only trace amounts of either cytokine were detected at the earlier 4 h reading. However, these data clearly demonstrate that both the dimeric gallotannin and to a larger extent β-D-PGG are effective at stimulating the production of IL-1β from h-PBMC's. In comparison, the dimeric structure appears to be much more proficient than the lower homolog at eliciting TNF-α release at these particular concentration values. These encouraging observations prompted a more detailed exploration of the dose-response profile for the polyphenolic constructs. Unfortunately, a limited supply of the nature product agrimoniin precluded examination of its TNF-α response.

h-PBMC's from two different subjects were utilized in independent experiments to obtain both IL-1β and TNF-α dose-response curves for the monomeric species and its dimeric counterpart at 24 h exposure. FIGS. 4-7. The coriariin A and LPS data are included in these graphs for comparison purposes. FIGS. 4 and 5 illustrate that β-D-pentagalloylglucose is similar to coriariin A in its ability to induce IL-1β secretion in either subject. In addition, these graphs reveal that similar properties also attend the O-1-galloyl coupled dimer of β-D-PGG, gallotannin-ellagitannin hybrid. Taken together, these results provide no support for the proposition that these polyphenolics must meet stringent molecular recognition criteria to initiate IL-1β release. Since Miyamoto's mouse studies did in fact discern well-defined structural requirements for anti-tumor activity among tannins (i.e., life span increase: coriariin A (238%), β-D-PGG (82%): regressors; coriariin A (3/6), β-D-PGG (0/6)), the role of IL-1β in the whole animal antitumor response is called into question.

The TNF-α release data (FIGS. 6 and 7), however, tell a different story. β-D-PGG promotes much less TNF-α discharge at comparable concentrations in either subject than does the dimer or coriariin A. In addition, the analog's dose-response profile is similar to that of coriariin A. at least in the lower concentration range. These data suggest that there is a structure-based discrimination between the monomeric and dimeric tan in species by some recognition element in the TNF-α induction pathway within h-PBMC's. This difference in TNF-α eliciting ability parallels the overall trend in antitumor properties for the mouse/sarcoma-180 system. Moreover, the similarity in IL-1β secretion profiles among the dissimilar species plausibly may just be an artifact of the first-formed TNF-α's ability to upregulate IL-1β production.

In conclusion, the ability of the dimeric tannin coriariin A and the coriariin A analog to induce higher levels of TNF-α from h-PBMC's compared to the monomeric compound β-PGG has been demonstrated. This observation is in accord with earlier in vivo studies wherein the dimeric tannins demonstrated better antitumor activity when compared to the monomeric tannins. These experimental results suggest that the extent of TNF-α production from h-PBMC's incubated with tannins may correlate with the antitumor potency of tannins. The activity of the dimeric gallotannin was indistinguishable from the activity of the related ellagitannin coriariin A, raising the possibility of using this structurally simpler, synthetically accessible species as a lead in the development of tannin-based chemotherapeutic agents.

EXAMPLE 3

Biological Pathway by which Tannins Operate

Experiments to probe if tannins modulate immune function through the LPS receptor system were undertaken. Specifically, do tannins interact with LBP/CD14 and Tlr4 to induce cytokine secretion? To test this question, the mouse strain C3H/HeJ, which is unresponsive to LPS at levels below 100 ng/mL, was used. These mice have a proline-to-histidine point mutation in the coding region of their Tlr4 protein which is believed to inhibit signal transduction.

Figure 8:
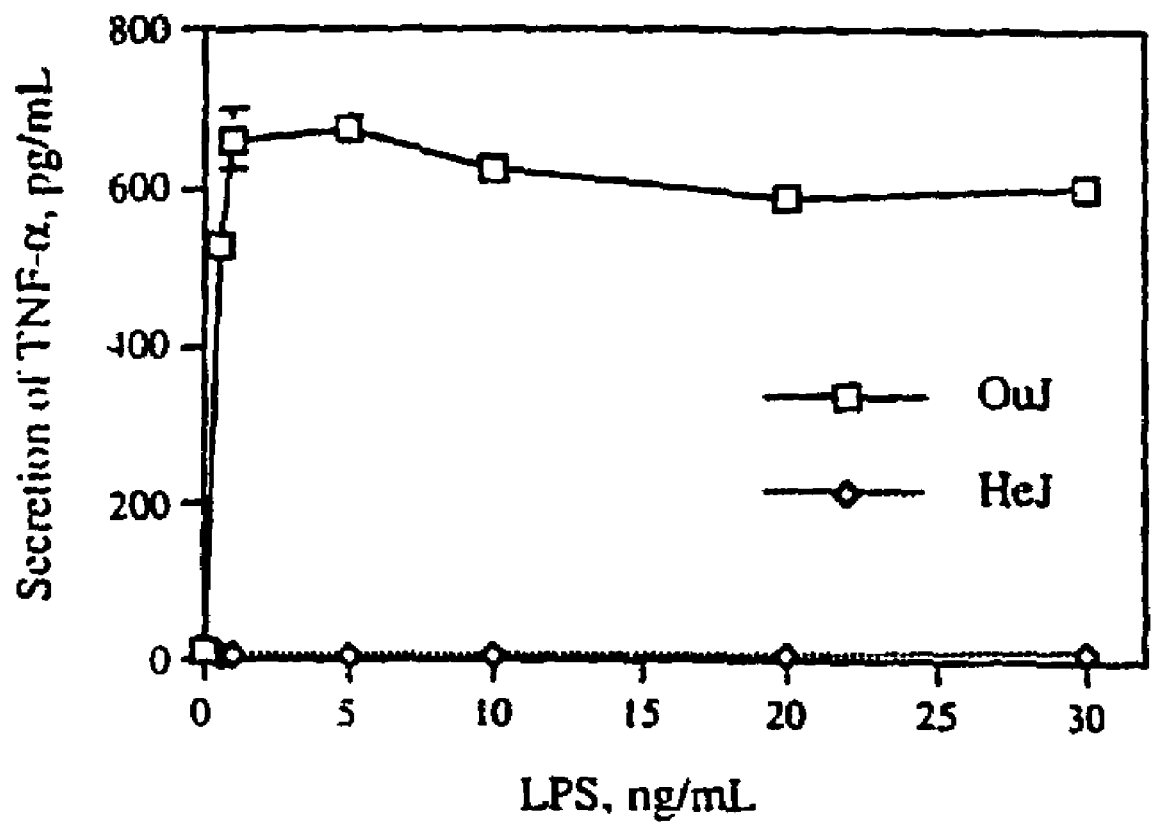
FIG. 8 shows the secretion of TNF-α from mouse PEC's stimulated with LPS (24 h incubation).
Figure 9:
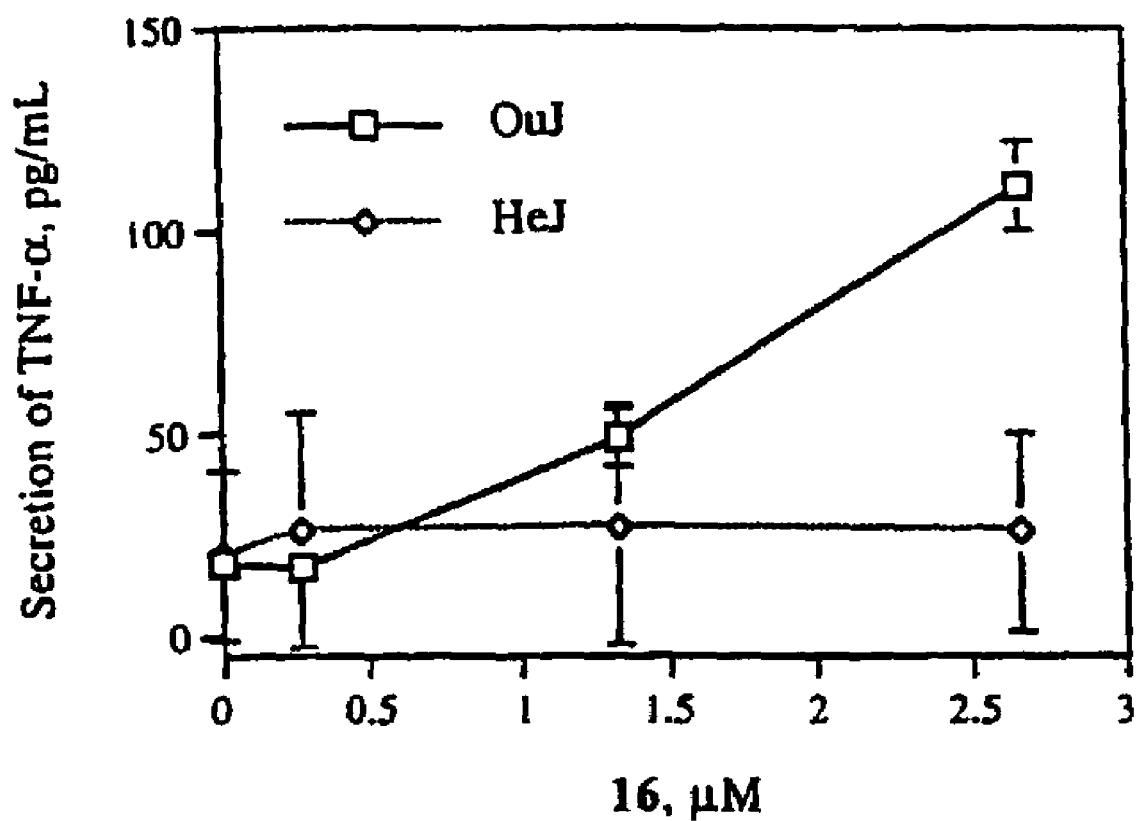
FIG. 9 shows the secretion of TNF-α from mouse PEC's stimulated with coriariin A analog (24 h incubation).

To verify that the C3H/HeJ mice were unresponsive to LPS, peritoneal exudate cells (PEC's) from both C3H/HeJ mice and a control group of mice which are LPS responsive (C3H/HeOuJ), were treated with low doses of LPS and TNF-α secretion was assayed by standard ELISA. These results illustrate that the HeJ mice were in fact LPS unresponsive (no TNF-α secretion observed), while the OuJ mice showed a typical LPS dose response curve (FIG. 8). Coriariin A analog was tested next. This compound has been shown to induce TNF-α secretion from h-PBMC's with dose response curves similar to LPS. It was found that the HeJ mice were also unresponsive to the coriariin A analog, whereas the OuJ mice showed a small response (FIG. 9) relative to their LPS response. These preliminary results suggest that tannins operate through the same Tlr4-mediated pathway that LPS utilizes.

EXAMPLE 4

In Vivo Studies with β-PGG

Figure 10:
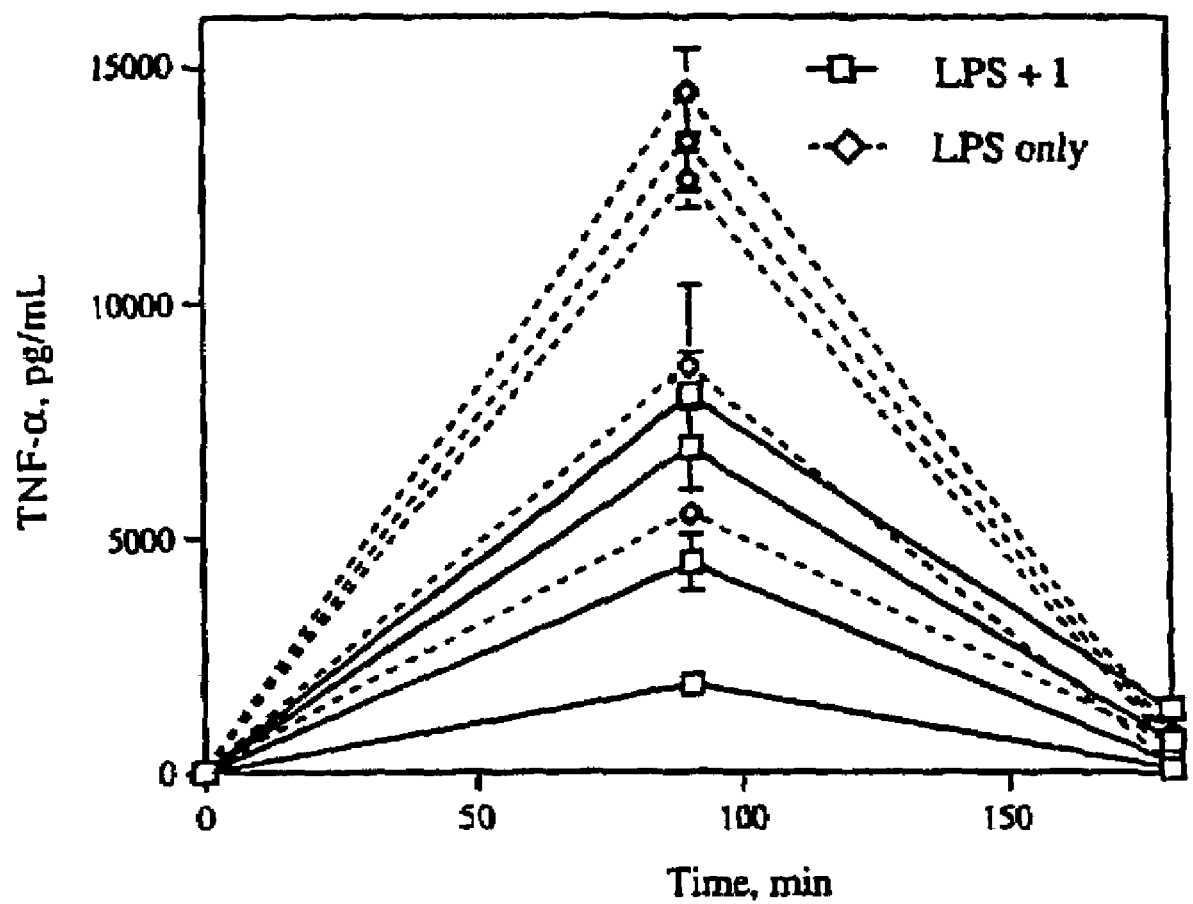
FIG. 10 shows the secretion of TNF-α from treatment of rats with LPS+β-PGG of LPS only.

The inventors have found that the gallotannin β-PGG can inhibit LPS induced secretion of TNF-α from h-PBMC's. The ability of β-PGG to function in vivo was investigated in collaboration with Dr. Charles Lang of the Hershey Medical School. In this experiment, two groups of rats were used. One group was intravenously administered 1 mg/kg of LPS as well as 25 mg of β-PGG. The second group was given only 1 mg/kg of LPS. Most of the rats administered β-PGG displayed suppressed levels of TNF-α secretion as compared to the LPS-only rats (FIG. 10). These preliminary in vivo results were encouraging, however several problems with the use of β-PGG as an inhibitor are evident. A large amount of β-PGG was required to elicit inhibition because β-PGG is a small monomeric gallotannin that is able to interact with other blood proteins such as rat serum albumin. In addition, even though the rats treated with β-PGG showed lower levels of TNF-α secretion, a septic shock response in the form of low blood pressure was still observed. This physiological effect may be due to secretion of the cytokine IL-1β which also has been shown to mediate septic shock. β-PGG causes secretion of high levels of IL-1β from h-PBMC's.

EXAMPLE 5

Synthesis of Dimeric Gallotannin Analogs

The next goal was to synthesize larger tannins which would be more selective in their biological interactions than the monomeric gallotannin β-PGG. Thus, a series of dimeric gallotannin analogs were prepared to determine the effect of changes in the linker unit joining the two carbohydrate cores on the biological activity. The linkers were chosen for various reasons (i.e. more rigidity), but all would change the distance between the carbohydrate cores compared to the active coriariin A analog. Analogs with linkers 17, 18, and 19 (as described supra) are more rigid linkers than the diaryl ether linkage present in the coriariin A analog. The analog allows for more flexibility and 21 probes the necessity for phenoxylation about the aryl rings.

The synthesis of these compounds involved the straightforward coupling of the appropriate bisacid chloride with alcohol, followed by benzyl ether hydrogenation to afford the final products 17c-21c. The couplings that furnished 17b, 18b, and 21b proceeded with high diastereoselectivity for the β,β' anomer. The synthesis of 19b required higher temperatures than the other analogs. This analog was obtained in a 4:1 ratio of β,β' to α,α' anomeric stereochemistry as determined by $^1$H NMR. The H(1) proton for the α,α'anomer appeared farther downfield (6.88 ppm) and had a smaller coupling constant (J=3.2 Hz) than the H(1) proton for the β,β' anomer (6.02 ppm, J=9.8 Hz). The synthesis of 20b always resulted in a mixture of β,β', α,α' and α,β' anomers. However, slow addition of 20a to the alcohol 22 gave predominantly the β,β' isomer. The H(1) proton for the α anomers appeared at 6.69 ppm with a coupling constant of 4.15 Hz.

Acid chlorides 19a and 20a are not commercially available, but were readily prepared. For example, 19a was prepared by conversion of the bisacid 23 to the acid chloride using oxalyl chloride and catalytic DMF (Scheme 8). Compound 21a was prepared in three steps. The diaryl ether ester was prepared by an Ullmann coupling. Hydrolysis resulted in the bisacid which was converted to the acid chloride by oxalyl chloride and catalytic DMF.

EXAMPLE 6

Biological Activity of Dimeric Gallotannin Analogs

Four studies examined the effect that analogs 17c-21c have on cytokine release from h-PBMC's. All assays were accompanied by appropriate controls: blank (negative) and LPS (positive).

Figure 11:
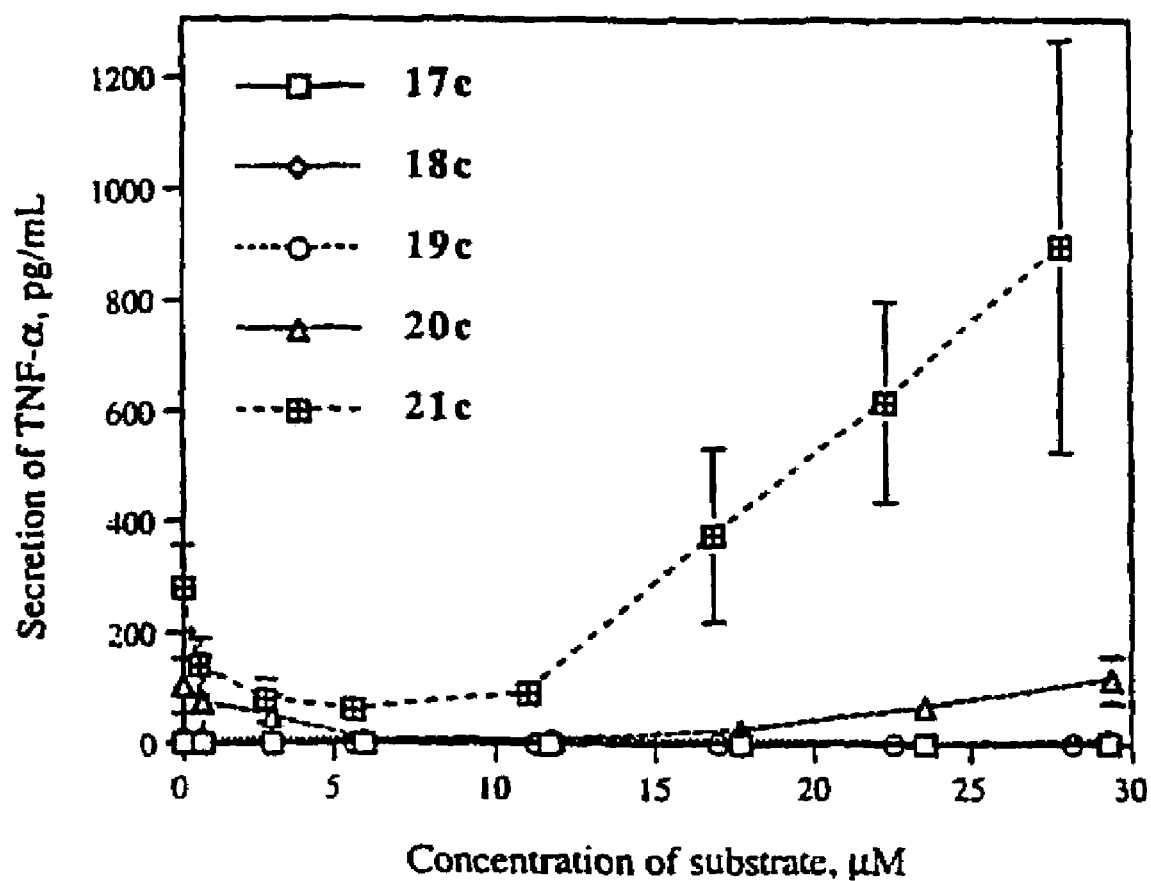
FIG. 11 shows the secretion of TNF-α from h-PBMC's stimulated with 17c-21c, 18c and 21c 1st subject; 17c, 19c, and 20c 2nd subject.

In the first study, the induction of TNF-α secretion from h-PBMC's in the presence of each compound 17c-21c was measured. The h-PBMC's were incubated with each compound for 24 hours. The TNF-α levels in the cell culture supernatant were assayed by Enzyme Linked ImmunoSorbant Assay (ELISA). The data point for each assay represent the mean of triplicate measurements. Only the diaryl ether containing species 21c induced any significant amount of TNF-α secretion from the h-PBMC's, an undesirable characteristic for a potential LPS antagonist. (See FIG. 11).

Figure 12:
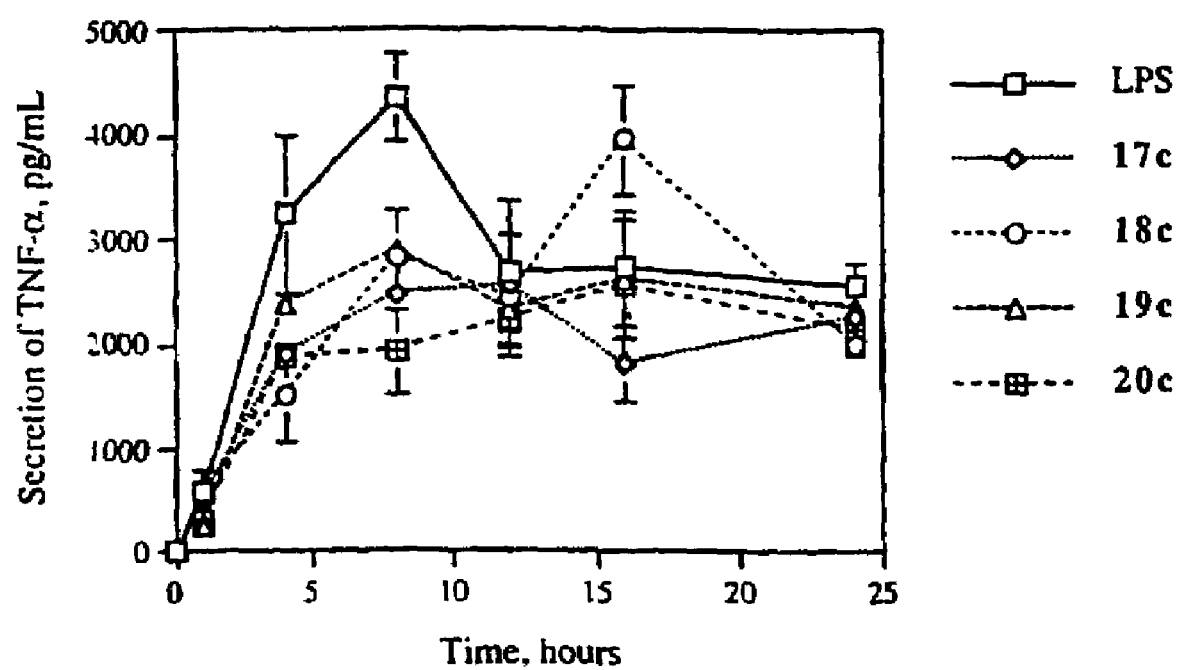
FIG. 12 shows the secretion of TNF-α over time from h-PBMC's (3rd subject stimulated with LPS (5 μg/mL) and 17c-20c (10 μg/mL).

In the second study, the ability of compounds 17c-20c to inhibit LPS induced TNF-α production in h-PBMC's was investigated using four assays. The first experiment was a kinetics run in which the h-PBMC's were initially incubated with a fixed concentration of LPS (5 μg/mL) for 45 minutes. This incubation period was followed by addition of a fixed concentration (10 μg/mL) of compounds 17c-20c. The cells were harvested at varying intervals of time. This kinetics assay showed that these compounds were able to inhibit LPS induced TNF-α secretion. The optimal time was determined by comparing the amount of TNF-α secreted by LPS alone to the amount of TNF-α secreted by LPS and substrate at each time point. Overall inhibition was found to be greatest at 8-hours (FIG. 12).

Figure 13:
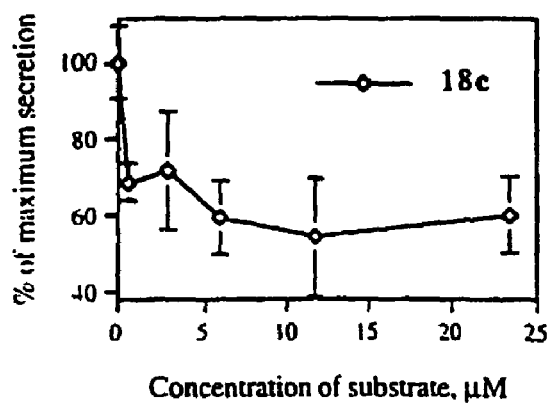
FIG. 13 shows inhibition of LPS (10 μg/mL) induced TNF-α secretion from h-PBMC's by 18c-20c (4th subject) expressed as percent of maximum response. Substrates added 45 minutes after addition of LPS to h-PBMC's.
Figure 13:
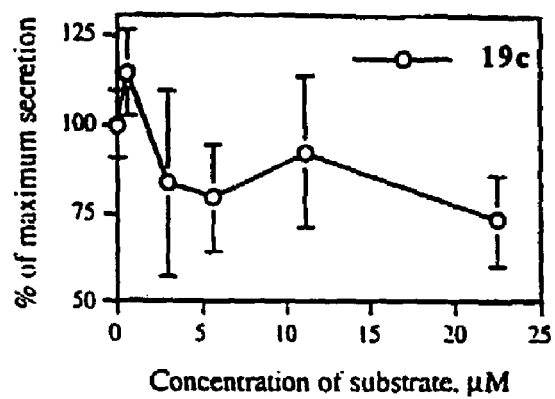
Figure 13:
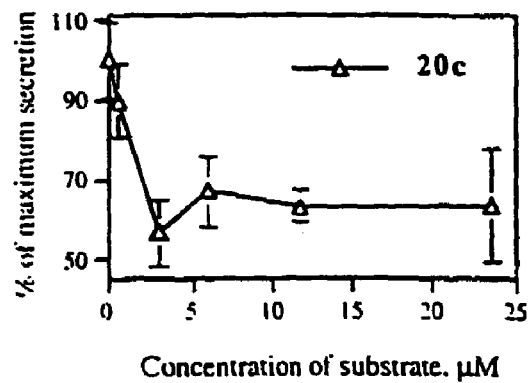

The second assay determined the minimum amount of substrate required for inhibition. LPS (10 μg/mL) was incubated with h-PBMC's for 45 minutes followed by addition of 17c-20c at varying concentrations. The cell culture supernatant was harvested after 8 hours. The inherent variability in using cells from different subjects, or in the day of assay, made it difficult to compare overall effectiveness of inhibitors. Therefore, to more easily identify the concentration at which maximum inhibition occurs for a given compound, the TNF-α secretion was normalized by calculating a percent of maximum secretion value (based on LPS alone) (FIG. 13). It was found that the inhibition is dose dependent. The optimal concentration for inhibition varied between substrates, but the general dose response trend was the same. Overall, the maximum inhibition was 45% for 18c and 20c, and 25% for 19c.

Figure 14:
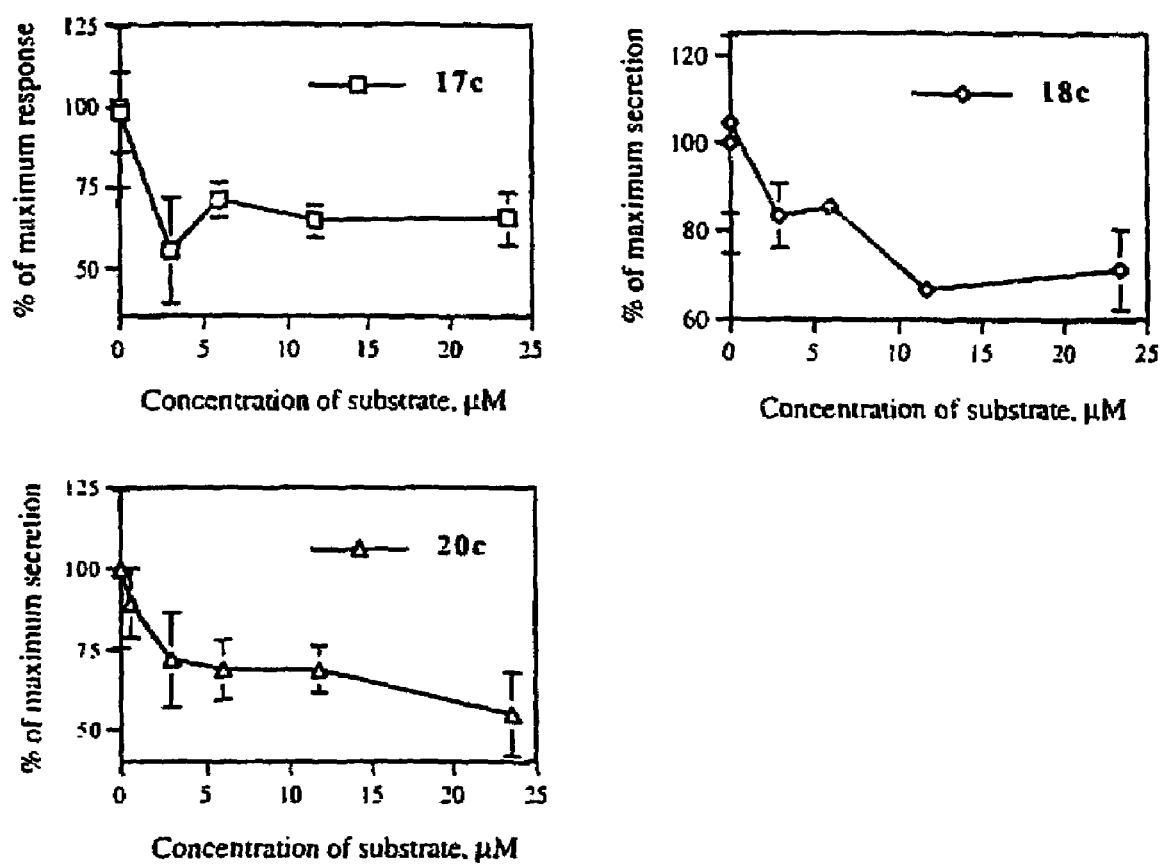
FIG. 14 shows inhibition of LPS (5 μg/mL) induced TNF-α secretion from h-PBMC's by 17c, 18c and 20c (3rd subject) expressed as percent of maximum response. Substrates added 45 minutes after addition of LPS to h-PBMC's.

The third assay investigated the ability of 17c, 18c, and 20c to inhibit LPS induced TNF-α secretion using a smaller dosage of LPS (5 μg/mL) (FIG. 14). Again, the response was dose dependent. The maximum inhibition was 45% for 17c and 20c, and 35% for 18c. These results are similar to those seen in FIG. 13, suggesting that either LPS dosage probably has already saturated the receptors.

Figure 15:
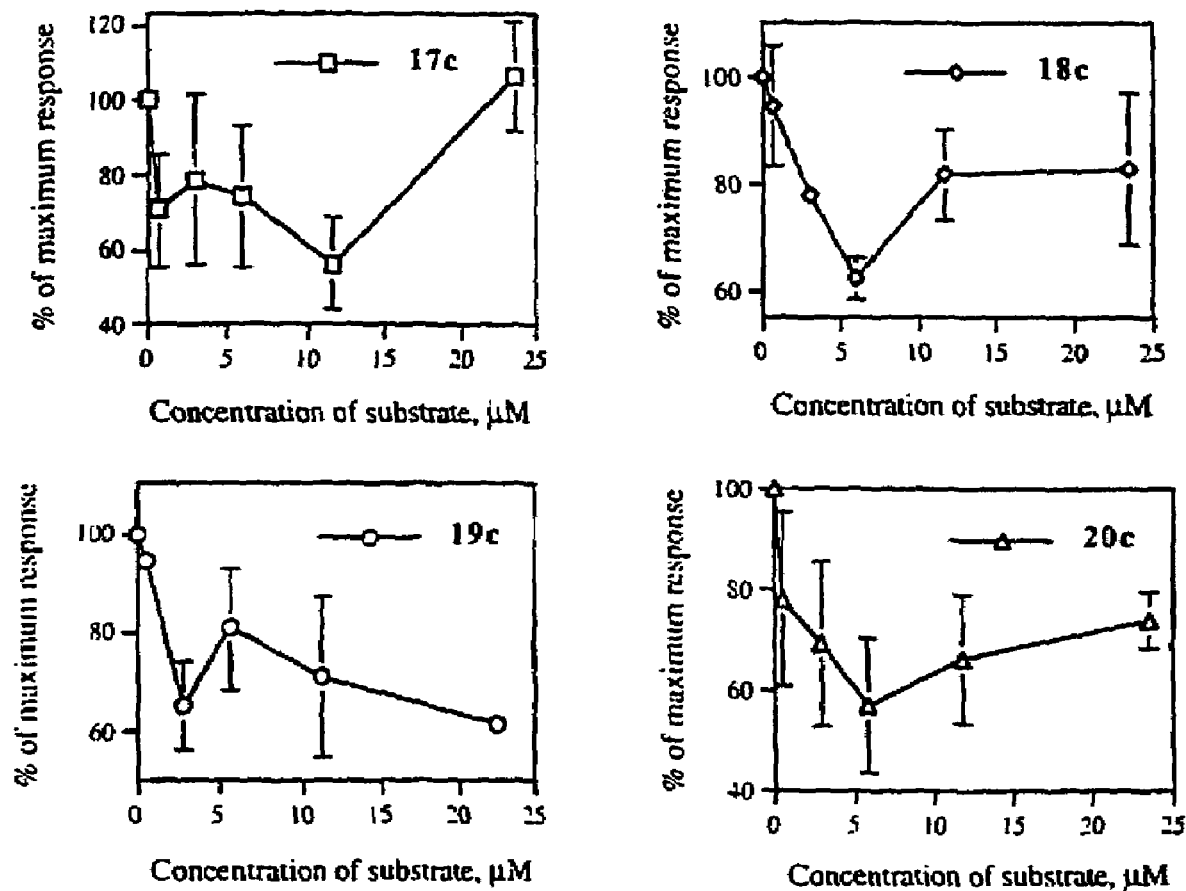
FIG. 15 shows inhibition of LPS (5 μg/mL) induced TNF-α secretion from h-PBMC's by 17c-20c (5th subject) expressed as percent of maximum response. Substrates added 45 minutes after addition of LPS to h-PBMC's.

In the fourth assay the varying concentrations of substrates 17c-20c and LPS were added at the same time to determine the effect of addition sequence on the inhibition of TNF-α secretion (FIG. 15). The addition time seemed to make a difference in the overall dose response trend. However, maximum inhibition was the same as when the compounds were added 45 minutes after LPS addition (about 40% for each compound).

Figure 16:
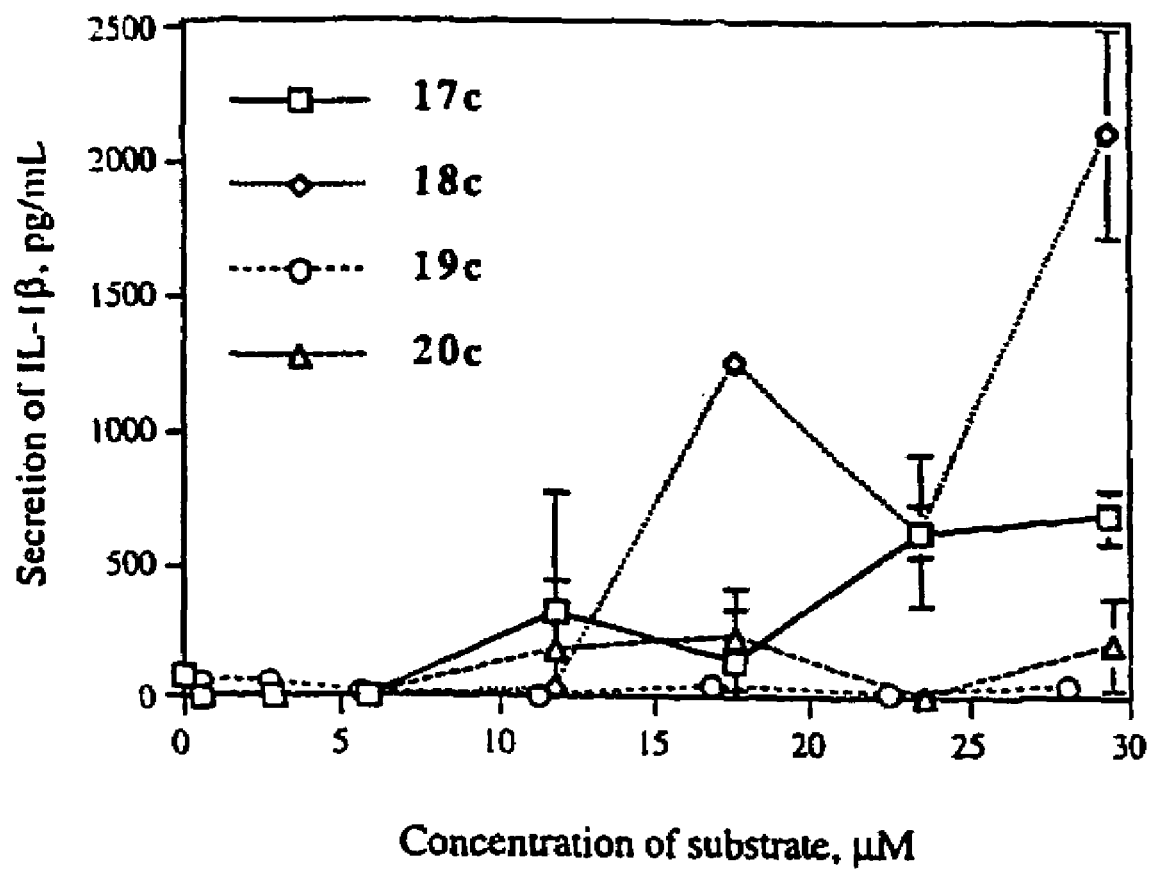
FIG. 16 shows secretion of IL-1β from h-PBMC's stimulated with 17c-20c (2nd subject).

In the third study, compounds 17c-20c were examined for their ability to induce secretion of IL-1β from h-PBMC's (FIG. 16). Recall from the introduction that the cytokine IL-1β is also released in an LPS-stimulated septic shock response. The compounds that cause very little secretion of IL-1β or none at all will be the optimal compounds for potential septic shock therapeutics because they will be less likely themselves to induce a septic shock response. The compounds chosen for further study were 19c and 20c because they induced the lowest amounts of IL-1β production.

Figure 17:
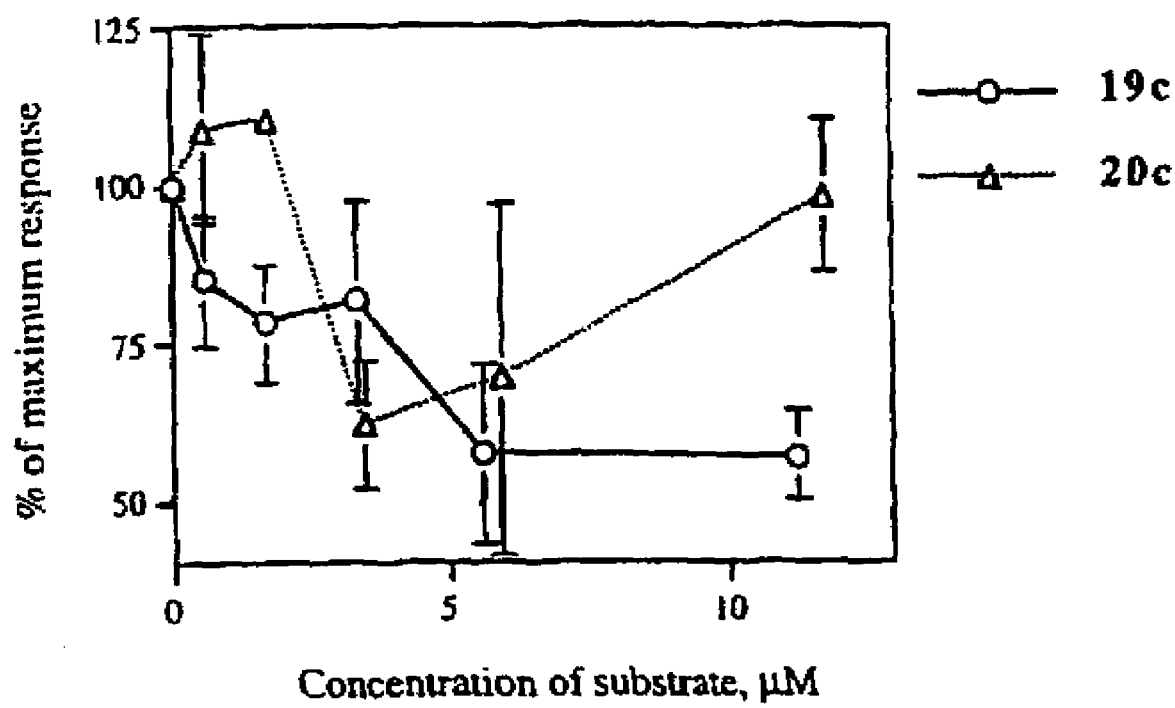
FIG. 17 shows inhibition of LPS (1 μg/mL) induced TNF-α secretion from h-PBMC's by 19c and 20c (4th subject) expressed as percent of maximum response. Substrates added 45 minutes after addition of LPS to h-PBMC's (8 h incubation).

Finally, in the last study, analogs 19c and 20c were again tested for inhibition LPS induced TNF-α secretion (FIG. 17). In this assay a smaller dose of LPS was used to determine if inhibition was greater when much lower doses of LPS were present. The substrates were added 45 minutes after LPS addition and the cells were harvested after 8 hours. It doesn't appear as though the substrates are better inhibitors when smaller amounts of LPS are used, again perhaps reflecting receptor saturation with LPS at this dosage.

CONCLUSIONS

Preliminary experiments suggest that ellagitannins may operate through the same biological pathway as LPS, at least as far as utilizing the Tlr4 receptor, but further investigation is warranted. The gallotannin β-PGG has been shown to inhibit LPS induced TNF-α secretion in rats. However, a large amount of this compound was necessary to see any inhibition, and a septic shock response was observed in all cases. High levels of induced IL-1β may be responsible for this observation. Dimeric tannin analogs 17c-21c were synthesized as potential LPS antagonists. Compounds 17c-20c caused little or no TNF-α secretion in h-PBMC's and were able to inhibit LPS induced levels of TNF-α in h-PBMC's. Compounds 19c-20c were the most promising antagonists in that they elicited very little secretion of the cytokine IL-1β. These will require further in vivo investigation to determine if they are candidates for sepsis/septic shock therapeutic development.

SYNTHETIC CHEMISTRY

Nuclear magnetic resonance spectra ($^1$H NMR, $^{13}$C NMR) were recorded on either 300 or 360 MHz ($^1$H) spectrometers. Low resolution fast atom bombardment mass spectra (FABMS) were obtained in a nitrobenzyl alcohol (NBA) matrix. High resolution fast atom bombardment mass spectra were run at the University of Texas, Austin. Elemental analysis was performed by Midwest Microlab, Indianapolis, Ind. Flash column chromatography was carried out using 32-63 μm silica gel and the indicated solvent. Ether and tetrahydrofuran were purified by distillation from sodium/benzophenone under argon. Benzene, methylene chloride and methanol were distilled from $CaH_2$ under argon. Triethylamine was distilled from $CaH_2$ and stored over 4 Å molecular sieves. Moisture sensitive reactions were carried out in pre-dried glassware under an argon atmosphere.

Methyl 3-Benzyloxy-4,5-dihydroxybenzoate. To a solution of methyl-3,4,5-trihydroxybenzoate (10.0 g, 54.3 mmol) and amberlyst (0.2 g) in 40 mL of benzene was added triethylorthoformate (32 mL, 270 mmol). The reaction mixture heated to reflux under Ar for 18 h. The reaction mixture was then filtered while hot and the filtrate was concentrated in vacuo. To the resulting oil was added 20 mL of acetone, benzyl bromide (38.7 mL, 326 mmol), and potassium carbonate (oven dried, 22.4 g, 163 mmol). The reaction mixture was heated to reflux under Ar for 20 h. This mixture was cooled, treated with triethylamine (37.3 mL, 272 mmol) and extracted with EtOAc. The organic layer washed sequentially with 10% $H_2SO_4$, $H_2O$, and brine, and dried over $Na_2SO_4$. The solvents were removed in vacuo. To the remaining oil was added 20 mL of MeOH and $TsOHH_2O$ (100 mg, 0.5 mmol). This solution was stirred at rt under Ar for 20 h. The reaction mixture was cooled, concentrated in vacuo and extracted with EtOAc. The organic layer washed sequentially with $NaHCO_3$, $H_2O$, and brine and dried over $Na_2SO_4$. After filtration and concentration, the product was purified by flash chromatography using hexane followed by 25% EtOAc in hexane as eluent to yield 10 g (71%) of methyl 3-benzyloxy-4,5-dihydroxybenzoate.

Methyl 3,4,5-Tribenzyloxybenzoate. Benzyl bromide (10.6 mL, 89.7 mmol) was added to a solution of methyl 3,4,5-trihydroxybenzoate (5.0 g, 27 mmol) and potassium carbonate (oven dried, 12.4 g, 89.7 mmol) in 250 mL of acetone. This solution was heated to reflux under Ar for 24 h. The reaction mixture was cooled, treated with triethylamine (7.6 mL, 54 mmol), and extracted with EtOAc. The organic layer washed sequentially with 10% $H_2SO_4$, $H_2O$, and brine, and dried over $Na_2SO_4$. After filtration and concentration, 11.8 g (96%) of methyl 3,4,5-tribenzyloxybenzoate was collected as an off white solid.

5-Benzyloxy-3,4-di-t-butyldimethylsiloxybenzoyl Chloride. A solution of 5-benzyloxy-3,4-di-t-butyldimethylsiloxybenzoic acid (1 g, 2 mmol) in 46 mL of benzene was added to a solution of NaH (80 mg, 2 mmol) in 2 mL of benzene. The resulting solution was stirred with oxalyl chloride (0.9 mL, 10 mmol) under Ar for 20 h. Removal of solvent afforded 0.93 g (91%) of 5-benzyloxy-3,4-di-t-butyldimethylsiloxybenzoyl chloride as a yellow solid.

1-O-(3-Benzyloxy-1,2-dioxocyclohexa-3,5-diene-5-benzoyl)-2,3,4,6-tetrakis(3,4,5-tribenzyloxybenzoyl)-β-D-glucopyranoside. A solution of ortho-chloranil (47 mg, 0.17 mmol) in 1 mL of dry ether (0.17 M in ortho-chloranil) was cooled to −40° C. To this solution was added dropwise a solution of 1-O-(2-benzyloxy-4,5-dihyroxybenzoyl)2,3,4,6-tetrakis(3,4,5-tribenzyloxybenzoyl)-β-D-glucopyranoside (330 mg, 0.16 mmol) in 24 mL of dry ether (0.007 M in diphenol) over a period of 15 min. The resulting red solution was stirred at −40° C. for 2 h under Ar, and then transferred to a −20° C. freezer and left for 20 h. The red precipitate was filtered, rinsed with cold ether and dried in vacuo to afford 260 mg (79%) of 1-O-(3-benzyloxy-1,2-dioxocyclohexa-3,5-diene-5-benzoyl)-2,3,4,6-tetrakis(3,4,5-tribenzyloxybenzoyl)-β-D-glucopyranoside.

General Procedure A: Bisacylation of 2,3,4,6-Tetrakis(3,4,5-tribenzyloxybenzoyl)-D-glucose. (mixture of α,β anomers): To a solution of 2,3,4,6-tetrakis(3,4,5-tribenzyloxybenzoyl)-D-glucose (300 mg, 0.2 mmol) in 1.5 mL of dry $CH_2Cl_2$ was added triethylamine (67 μL, 0.43 mmol) followed by the appropriate bisacid chloride (0.1 mmol). This solution was stirred under an Ar for 18 h. The reaction mixture was treated with 1N HCl and extracted with EtOAc. The organic layer washed sequentially with $H_2O$ and brine, and then dried over $Na_2SO_4$. After filtration and removal of the solvents in vacuo, the product was purified by flash chromatography using 3:5:12 EtOAc:benzene:hexane.

General Procedure B: Hydrogenation. To a 0.008 M solution of the appropriate benzylated dimer in THF was added 10% Pd/C (0.6 eq). The reaction mixture was purged 4× with $H_2$ and stirred at rt under a $H_2$ atmosphere for 18 h. The reaction mixture was filtered through Celite which was rinsed with acetone. After concentration, the resulting gray solid was tritutated with hexane and ether and dried under vacuum at 35° C.

1,1'-O-2,2',3,3',4,4',6,6'-Tetrakis(3,4,5-tribenzyloxybenzoyl)-β,β'-D,D'-glucopyranosylterephthalate. By use of general procedure A, terephthaloyl chloride was coupled to 2,3,4,6-tetrakis(3,4,5-tribenzyloxybenzoyl)-D-glucose and purified by flash chromatography to afford 61% of 1,1'-O-2,2',3,3',4,4',6,6'-tetrakis(3,4,5-tribenzyloxybenzoyl)-β,β'-D,D'-glucopyranosylterephthalate. IR (CDCl$_3$) 1734 (C═O) cm$^{-1}$; $^1$H NMR (CDCl$_3$, 300 MHz) δ 8.02 (s, 4H, (C═O)ArH), δ 7.43-7.15 (m, 136H, ArH), δ 6.25 (d, J=8.3 Hz, 2H, H(1), H(1)'), δ 6.05 (app. t,J=9.8 Hz, 2H, H(3), H(3)'), δ 5.82 (dd, J=10.2, 8.3 Hz, 2H, H(2), H(2)'), δ 5.7 (app. t, J=9.8 Hz, 2H, H(4), H(4)'), δ 5.11-4.91 (m, 48H, ArOCH$_2$), δ 4.77 (d, J=9.4 Hz, 2H, H$_a$(6), H$_a$(6)'), δ 4.47-4.42 (m, 2H, H(5), H(5)'), δ 4.35-4.29 (m, 2H, H$_b$(6), H$_b$(6)'); $^{13}$C NMR (CDCl$_3$, 75 MHz) δ 165.64, 165.51, 164.99, 164.82, 163.67, 152.57, 152.52, 152.43, 143.17, 143.10, 142.56, 137.43, 137.31, 137.23, 136.59, 136.33, 136.24, 132.92, 130.28, 128.51, 128.46, 128.41, 128.24, 128.19, 128.10, 128.01, 127.82, 127.52, 124.40, 123.56, 123.47, 109.28, 109.09, 109.03, 93.17, 75.06, 73.37, 73.25, 71.14, 71.11, 70.98, 69.75, 63.19; MS (+FAB) 3867 (MH$^+$ 16); Anal. Calcd. for C$_{244}$H$_{202}$O$_{46}$: C, 75.74, H, 5.23, Found: C, 75.59, H, 5.29.

1,1'-O-2,2',3,3',4,4',6,6'-Tetrakis(3,4,5-trihydroxybenzoyl)-β,β'-D,D'-glucopyranosylterephthalate. By use of general procedure B, 1,1'-O-2,2',3,3',4,4',6,6'-tetrakis(3,4,5-tribenzyloxybenzoyl)-β,β'-D,D'-glucopyranosylterephthalate was hydrogenated to afforded a quantitative yield of 1,1'-O-2,2',3,3',4,4',6,6'-tetrakis(3,4,5-trihyroxybenzoyl)-β,β'-D,D'-glucopyranosylterephthalate. IR (KBr) 3422 (OH) 1702 (C═O) cm$^{-1}$; $^1$H NMR ((CD$_3$)$_2$CO, 300 MHz) δ 8.5-7.4 (m, 24H, OH), δ 8.05 (s, 4H, (C═O)ArH), δ 7.13-6.94 (m, 16H ArH), δ 6.37 (d, J=8.3 Hz, 2H, H(1), H(1)'), δ 6.02 (app. t, J=9.5 Hz, 2H H(3), H(3)'), δ 5.68-5.58 (m, 4H, H(2), H(2)', 1H(4), H(4)'), δ 4.61-4.54 (m, 4H, H(5), H(5)', H$_a$(6), H$_a$(6)'), δ 4.41-4.35 (dd, J=12.5, 4.5 Hz, 2H, H$_b$(6), H$_b$(6)'); $^{13}$C NMR ((CD$_3$)$_2$CO, 75 MHz) δ 165.45, 164.94, 164.88, 164.66, 163.30, 145.13, 145.06, 144.99, 138.54, 138.31, 138.15, 135.93, 133.25, 130.01, 128.36, 120.48, 119.69, 119.61, 119.43, 109.39, 109.23, 93.18, 73.19, 72.07, 70.92, 68.28, 61.82; MS (+FAB) 1706 (M+6)(MH$^+$ 7); HRFABMS Cald for C$_{76}$H$_{58}$O$_{46}$: 1706.219926, Found: 1706.223226.

1,1'-O-2,2',3,3',4,4',6,6'-Tetrakis(3,4,5-tribenzyloxybenzoyl)-β,β'-D-glucopyranosylisophthalate. By use of general procedure A, isophthaloyl chloride was coupled to 2,3,4,6-tetrakis(3,4,5-tribenzyloxybenzoyl)-D-glucose and purified by flash chromatography to afford 48% of 1,1'-O-2,2',3,3',4,4',6,6'-tetrakis(3,4,5-tribenzyloxybenzoyl)-β,β'-D,D'-glucopyranosylisophthalate. IR (CDCl$_3$) 1730 (C═O) cm$^{-1}$; $^1$H NMR (CDCl$_3$, 300 MHz) δ 8.76 (s, 1H, (C═O)ArH (C═O)), δ 8.19 (dd, J=7.9, 1.5 Hz, 2H, (C═O)ArH) δ 7.42-7.15 (m, 137H, ArH), δ 6.26 (d, J=8.2 Hz, 2H, H(1), H(1)'), δ 6.01 (app. t. J=9.4 Hz, 2H, H(3), H(3)'), δ 5.79 (dd, J=9.8, 8.3 Hz, 2H, H(2), H(2)'), δ 5.74 (app. t, J=9.4 Hz, 2H, H(4), H(4)'), δ 5.09-4.90 (m, 48H, ArOCH$_2$), δ 4.76 (d, J=9.0 Hz, 2H, H$_a$(6), H$_a$(6)'), δ 4.41-4.30 (m, 4H, H(5), H(5)', H$_b$(6), H$_b$(6)'); $^{13}$C NMR (CDCl$_3$, 75 MHz) δ 165.66, 165.53, 164.95, 164.86, 163.60, 152.58, 152.55, 152.43, 143.18, 143.06, 142.57, 137.48, 137.34, 137.29, 136.64, 136.40, 136.36, 136.29, 129.34, 128.93, 128.85, 128.74, 128.51, 128.43, 128.28, 128.13, 128.04, 127.82, 127.72, 127.55, 124.44, 123.66, 123.60, 109.30, 109.08, 93.12, 75.16, 75.09, 73.33, 73.19, 71.22, 71.15, 70.99, 69.70, 63.13; MS (+FAB) 3867 (MH$^+$ 7); Anal. Calcd. for C$_{244}$H$_{202}$O$_{46}$: C, 75.74, H, 5.23, Found: C, 75.61, H, 5.23.

1,1'-O-2,2',3,3',4,4',6,6'-Tetrakis(3,4,5-trihydroxybenzoyl)-β,β'-D-glucopyranosylisophthalate. By use of general procedure B, 1,1'-O-2.2',3,3',4,4',6,6'-tetrakis(3,4,5-tribenzyloxybenzoyl)-β,β'-D,D'-glucopyranosylisophthalate was hydrogenated to afford a quantitative yield of 1,1'-O-2.2',3,3',4,4',6,6'-tetrakis(3,4,5-trihyroxybenzoyl)-β,β'-D,D'-glucopyranosylisophthalate. IR (KBr) 3405 (OH) 1702 (C═O) cm$^{-1}$; $^1$H NMR ((CH$_3$)$_2$CO), 300 MHz) δ 8.58 (s. 1H, (C═O)ArH(C═O)), δ 8.45-7.85 (m, 24H, OH), δ 8.17 (dd. J=7.5, 1.5 Hz, 2H, (C═O)ArH), δ 7.61 (t, J=7.9 Hz, 1H, ArH) δ 7.12-6.94 (m. 16H. ArH), δ 6.40 (d, J=7.9 Hz, 2H, H(1), H(1)'), δ 6.00 (app. t. J=9.4 Hz, 2H, H(3), H(3)'), δ 5.68-5.59 (m, 4H, H(2), H(2)', H(4), H(4)'), δ 4.61-4.49 (m, 4H, H(5), H(5)', H$_a$(6), H$_a$(6)'), δ 4.42-4.36 (dd, J=12.8, 4.5 Hz, 2H, H$_b$(6), H$_b$(6)'); $^{13}$C NMR (CDCl$_3$, 75 MHz) δ 166.04, 165.51, 165.38, 165.23, 163.81, 145.66, 145.60, 144.53, 139.05, 138.85, 138.71, 136.87, 135.31, 135.19, 130.33, 130.13, 121.05, 120.28, 120.86, 120.28, 120.21, 120.06, 109.96, 109.89, 109.79, 93.68, 73.79, 72.80, 71.50, 69.80, 62.42; MS (+FAB) 1706 (M$^+$ 14); HRFABMS Cald for C$_{36}$H$_{58}$O$_{46}$; 1706.219926, Found: 1706.222124.

Biphenyl-4.4'-dicarbonyl Dichloride. A solution of biphenyl-4,4'-dicarboxylic acid (200 mg. 0.8 mmol) in 15 mL of CH$_2$Cl$_2$ was stirred with oxalyl chloride 0.8 mL. 9 mmol) and 1 drop DMF under Ar for 18 h. Removal of solvents in vacuo afforded 211 mg (93%) of biphenyl-4,4'-dicarbonyl dichloride as a yellow solid. Spectral data matches the referenced spectral data. IR (CH$_2$Cl$_2$) 1781 (C═O) cm; H NMR (CDCl₃), 360 MHz) δ 8.2 (d, J=8.2 Hz, 4H(C=O) ArH), δ 7.7 (d. J=8.7 Hz, 4H, ArH); ³C NMR (CDCl₃, 90 MHz) δ 167.9, 145.8, 133.2, 132.1, 127.9.

1,1'-O-2,2',3,3',4,4',6,6'-Tetrakis(3,4,5-tribenzyloxybenzoyl)-β,β'-D,D'-glucopyranosylbiphenyl-4,4'-diester. To a solution of 2,3,4,6-tetrakis(3,4,5-tribenzyloxybenzoyl)-D-glucose (440 mg, 0.24 mmol) in 3 mL of dry THF was added triethylamine (67 μL, 0.48 mmol) followed by biphenyl-4,4'-dicarbonyl dichloride (33 mg, 0.12 mmol). The resulting mixture was heated to 50° C. and stirred under Ar for 40 h (Note: If the mixture was heated to reflux (65° C.), a mixture of 4:1 β,β':α,α' isomers was obtained). The reaction mixture was treated with 1N HCl and extracted with EtOAc. The organic layer washed sequentially with H₂O and brine, and then dried over Na₂SO₄. After removal of the solvents in vacuo, the product was purified by flash chromatography using 3:5:12 EtOAc:benzene:hexane to afford 1,1'-O-2,2',3,3',4,4',6,6'-tetrakis(3,4,5-tribenzyloxybenzoyl)-β,β'-D,D'-glucopyranosylbiphenyl-4,4'-diester (17%). IR (CDCl₃) 1732 (C=O) cm⁻¹; ¹H NMR (CDCl₃, 300 MHz) δ 8.08 (d, J=8.3 Hz, 4H, (C=O)ArH), δ 7.57 (d, J=8.6 Hz, 4H, ArH), δ 7.47-7.18 (m, 136H, ArH), δ 6.35 (d, 2H, J=8.3 Hz, H(1), H(1)'), δ 6.07 (app. t. 2H, J=9.4 Hz, H(3), H(3)'), δ 5.87 (dd, J=9.5, 8.3 Hz, 2H, H(2), H(2)'), δ 5.76 (app. t. J=9.7 Hz, H(4), H(4)'), δ 5.15-4.80 (m. 50H. ArCH₂O, H_b(6), H_b(6)'), δ 4.49-4.33 (m, 4H, H(5), H(5)', H_a(6), H_a(6)'); ¹³C NMR (CDCl, 75 MHz) δ 168.59, 165.60, 165.54, 165.03, 164.24, 152.56, 152.50, 152.42, 144.55, 143.00, 142.49, 137.42, 137.30, 137.24, 136.63, 136.31, 136.24, 133.42, 132.57, 128.79, 128.71, 128.66, 128.59, 128.46, 128.39, 128.26, 128.19, 128.10, 127.99, 127.82, 127.58, 127.51, 123.61, 123.52, 109.28, 109.09, 109.00, 75.11, 75.06, 71.18, 71.08, 70.98, 69.27, 63.12; Anal. Calcd. for C₂₅₀H₂₀₆O₄₆; C, 76.10, H, 5.23, Found: C, 75.85, H, 5.31.

1,1'-O-2.2',3,3',4,4',6,6'-Tetrakis(3,4,5-trihyroxybenzoyl)-β,β'-D,D'-glucopyranosylbiphenyl-4.4'-diester. By use of general procedure B, 1,1'-O-2,2',3,3',4,4',6,6'-tetrakis(3,4,5-tribenzyloxybenzoyl)-β,β'-D,D'-glucopyranosylbiphenyl-4,4'-diester was hydrogenated to afford 1,1'-O-2,2',3,3',4,4',6,6'-tetrakis(3,4,5-trihyroxybenzoyl)-β,β'-D,D'-glucopyranosylbiphenyl-4,4'-diester (86%). IR (KBr) 3448 (OH) 1702 (C=O) cm⁻¹; ¹H NMR ((CD₃)₂CO, 300 MHz) δ 8.28-8.08 (m, 24H, OH), δ 8.05 (d, J=8.7 Hz, 4H, (C=O)ArH), δ 7.79 (d, J=8.3 Hz, 4H, ArH) δ 7.14-6.95 (m, 16H, ArH), δ 6.40 (d, J=8.3 Hz, 2H, H(1), H(1)'), δ 6.02 (app. t, J=9.8 Hz, 2H, H(3), H(3)'), δ 5.71-5.61 (m, 4H, H(2), H(2)', H(4), H(4)'), δ 4.61-4.52 (m, 4H H(5), H(5)', H_a(6), H_a(6)'), δ 4.41-4.39 (dd, J=12.4, 4.9 Hz, 2H, H_b(6), H_b(6)'); ¹³C NMR ((CD₃)₂CO, 90 MHz) δ 167.28, 166.77, 166.66, 166.50, 165.68, 146.92, 146.81, 146.54, 140.29, 140.10, 139.93, 138.88, 132.31, 132.25, 130.20, 129.42, 122.37, 121.56, 121.49, 121.38, 111.22, 111.11, 111.05, 94.69, 74.96, 74.03, 72.78, 71.18, 63.66; MS (+FAB) 1782 (M⁺); HRFABMS Calcd for C₈₂H₆₂O₄₆: 1782.251226, Found: 1782.250700.

1,1'-O-2,2',3,3',4,4',6,6'-Tetrakis(3,4,5-tribenzyloxybenzoyl)-β,β'-D,D'-glucopyranosylpimelate. By use of general procedure A, pimeloyl chloride was coupled to 2,3,4,6-tetrakis(3,4,5-tribenzyloxybenzoyl)-D-glucose and purified by flash chromatography to afford 45% of 1,1'-O-2,2',3,3',4,4',6,6'-tetrakist(3,4,5-tribenzyloxybenzoyl)-β,β'-D,D'-glu-copyranosylpimelate (mixture of α,α, β,β, and α,β anomers). IR (CDCl₃) 1730 (C=O) cm⁻¹; ¹H NMR (CDCl₃, 300 MHz) δ 7.43-7.18 (m, 136H, ArH), δ 6.09 (d, J=7.9 Hz, 2H, H(1), H(1)'), δ 5.98 (app. t, J=9.4 Hz, 2H, H(3), H(3)'), δ 5.81-5.6 (m, 2H, H(2), H(2)'), δ 5.41-5.36 (m, 2H, H(4), H(4)'), δ 5.13-4.72 (m, 50H, ArOCH₂, H_a(6), H_a(6)') δ 4.54-4.27 (m, 4H, H(5), H(5)', H_b(6), H_b(6)'); ¹³C NMR (CDCl₃, 90 MHz) δ 171.53, 165.82, 165.63, 164.69, 152.68, 152.57, 152.52, 152.44, 143.25, 143.12, 143.08, 142.99, 142.66, 142.57, 137.48, 137.34, 136.65, 136.48, 136.41, 136.36, 136.21, 128.52, 125.46, 128.39, 128.31, 128.26, 128.21, 128.13, 128.11, 128.02, 127.83, 127.56, 124.48, 123.81, 123.68, 123.64, 123.57, 109.40, 109.23, 109.09, 92.05, 75.12, 75.08, 73.54, 72.98, 71.28, 71.16, 71.09, 70.99, 69.90, 63.05, 33.66, 28.12, 23.93; MS (+FAB) 3861 (MH⁺ 50).

1,1'-O-2,2',3,3',4,4',6,6'-Tetrakis(3,4,5-trihyroxybenzoyl)-β,β'-D,D'-glucopyranosylpimelate. By use of general procedure B, 1,1'-O-2,2',3,3',4,4',6,6'-tetrakis(3,4,5-tribenzyloxybenzoyl)-β,β'-D,D'-glucopyranosylpimelate was hydrogenated to afford quantitative yields of 1,1'-O-2,2',3,3',4,4',6,6'-tetrakis(3,4,5-trihyroxybenzoyl)-β,β'-D,D'-glucopyranosylpimelate. IR (KBr) 3422 (OH) 1718 (C=O) cm; ¹H NMR ((CD₃)₂CO, 300 MHz) δ 8.17-7.45 (m, 24H, OH), δ 7.21-6.82 (m, 16H, ArH), δ 6.05 (d, J=8.3 Hz. 2H. H(1), H(1)'), δ 5.79 (app. t, J=9.4 Hz. 2H. H(3), H(3)'), δ 5.48 (app. t, J=9.8 Hz. 2H, H(2), H(2)'), δ 5.96 (dd. J=9.8, 1.5 Hz, 2H, H(4), H(4)'), δ 4.40-4.34 (m, 4H, H(5), H(5)', H_a(6), H_a(6)'), δ 4.25 (dd. J=12.5, 4.5 Hz, 2H, H_b(6), H_b(6)'): ¹³C NMR (CD₃)₂CO, 75 MHz) δ 171.33, 165.83, 165.23, 164.97, 145.47, 145.43, 145.39, 145.26, 138.86, 138.80, 138.58, 138.49, 128.54, 120.79, 119.98, 119.89, 119.80, 109.67, 109.63, 109.54, 109.49, 92.16, 73.30, 72.62, 71.15, 68.57, 62.15, 33.61, 28.15, 24.38; MS (+FAB) 1701 (MH⁺); HRFABMS Cald for C₃₅H₆₄O₄₆; 1700.226876, Found: 1700.257740.

2.3'-Oxy-di-benzoic Acid. 24 (0.12 g, 0.41 mmol) was combined with LiOH.H₂O (0.11 g, 2.5 mmol) in 3 mL of MeOH and 1 mL of H₂O. The reaction mixture was heated to reflux under Ar for 5 h. The solution was cooled to rt. acidified with 1N HCl, and extracted with EtOAc. The organic layer was washed with brine and dried over MgSO₄. After filtration and removal of solvents in vacuo 0.1 g (93%) of white powder was collected. ¹H NMR ((CD₃)₂CO, 300 MHz) δ 9.5 (br s, 2H, CO₂H), δ 8.00 (dd. J=7.9 Hz, 1.9 Hz. 1H. H(3)), δ 7.75 (app. t of d, J=7.8, 1.2, 1H, H(4)'), δ 7.64 (ddd, J=8.2, 7.5, 1.8 Hz. 1H. H(5)), δ 7.53-7.46 (m, 2H, H(2)', H(5)'), δ 7.35 (app. d of t, J=7.6, 1.1 Hz, 1H, H(4)), δ 7.21 (ddd, J=8.2, 2.6, 1.0 Hz, 1HH(6)'), δ 7.14 (dd. J=8.2, 1.0 Hz, 1H, H(6)); ¹³C NMR ((CD₃)₂CO, 75 MHz) δ 166.6, 166.0, 158.8, 155.6, 134.4, 132.6, 132.5, 130.3, 125.0, 124.7, 124.2, 122.5, 122.3, 118.4.

2.3'-Oxy-di-benzoyl Chloride. Oxalyl chloride (0.058 μL, 0.66 mmol) was added slowly dropwise to a suspension of 25 (0.057 g, 0.22 mmol) in 2 mL dry CH₂Cl₂ and 1 drop DMF. The suspension gradually turned to a clear yellow solution. The reaction mixture stirred under Ar for 3 h. The solvent was removed in vacuo to yield 0.063 g (97%) of product as a yellow oil. IR (CDCl₃) 1758 (C=O) cm⁴: ¹H NMR (CDCl₃, 300 MHz) δ 8.19 (dd. J=8.3, 1.7 Hz, 1H, H(3)), δ 7.93-7.90 (m, 1H, H(4)'), δ 7.68 (app. t. J=2.1 Hz, 1H, H(2)'), δ 7.66-7.60 (m, 1H, H(4)), δ 7.52 (app. t. J=8.1 Hz. 1H, H(5)'), δ 7.36-7.31 (m, 2H. H(5), H(6)'), δ 7.00 (dd. J=8.3, 0.7 Hz, 1H, H(6)); $^{13}$C NMR (CDCl$_3$ 75 MHz) δ 167.6, 163.9, 156.9, 155.4, 136.1, 135.0, 134.3, 130.5, 126.8, 125.8, 125.4, 124.5, 120.5, 120.4.

1.1'-O-2,2',3,3',4,4',6,6'-Tetrakis(3,4,5-tribenzyloxybenzoyl)-β,β'-D,D'-glucopyranosyl-(2.3''-oxy-di-benzoate). By use of general procedure A. 21a was coupled to 2,3,4,6-tetrakis(3,4,5-tribenzyloxybenzoyl)-D-glucose and purified by flash chromatography to afford 35% of 1,1'-O-2,2',3,3',4,4',6,6'-tetrakis(3,4,5-tribenzyloxybenzoyl)-β,β'-D,D'-glucopyranosyl-(2.3'-oxy-di-benzoate). IR (CDCl$_3$) 1731 (C=O) cm$^{-1}$; $^{1}$H NMR (CDCl$_3$, 300 MHz) δ 7.97 (dd, J=7.9, 1.5 Hz, 1H, ArH(3)) δ 7.76-7.73 (m, 1H, ArH(4)'), δ 7.66-7.65 (m, 1H, Ar(H2)) δ 7.41-7.15 (m, 138H, ArH, ArH(4), ArH(5)'), 87.13-7.00 (m, 2H, ArH(5), ArH(6)') δ 6.72 (d, J=7.9 Hz, 1H, H(1)) δ 6.26 (d, J=7.9 Hz, 1H, H(1)'), δ 6.04 (app. t, J=9.8 Hz, 1H, H(3)) δ 5.97 (app. t, J=9.8 Hz, 1H, H(3)'), δ 5.82-5.68 (m, 4H, H(2), H(2)', 1H(4), H(4)'), δ 5.10-4.9 (m, 48H, ArOCH$_2$) δ 4.93-4.72 (m, 2H, H(5), H(5)'), δ 4.37-4.27 (m, 4H H$_a$(6), H$_a$(6)', H$_b$(6), H$_b$(6)'). $^{13}$C NMR (CDCl$_3$, 90 MHz) δ 165.5, 165.4, 165.0, 164.9, 164.8, 164.8, 164.0, 162.8, 162.8, 162.4, 157.3, 156.7, 152.5, 152.5, 152.4, 152.4, 143.1, 143.1, 143.0, 143.0, 143.0, 142.5, 142.5, 137.5, 137.5, 137.4, 137.3, 137.3, 136.7, 136.6, 136.4, 136.4, 136.3, 136.3, 134.9, 132.6, 130.2, 130.2, 128.5, 128.4, 128.3, 128.3, 128.2, 128.1, 128.0, 127.9, 127.8, 127.5, 124.8, 124.5, 124.5, 123.7, 123.7, 123.6, 120.6, 120.3, 119.5, 109.3, 109.1, 109.1, 92.9, 92.5, 75.1, 75.1, 73.6, 73.4, 73.1, 71.2, 71.1, 71.1, 71.0, 69.8, 69.7, 67.5, 63.2, 62.9.

1,1'-2,2',3,3',4,4',6,6'-Tetrakis(3,4,5-trihyroxybenzoyl)-β,β'-D,D'-glucopyranosyl-(2,3'-oxy-di-benzoate). By use of general procedure B, 1,1'-O-2,2',3,3',4,4',6,6'-tetrakis(3,4,5-tribenzyloxybenzoyl)-β,β'-D,D'-glucopyranosyl-(2,3'-oxy-di-benzoate) was hydrogenated to afford quantitative yields of 1,1'-O-2,2',3,3',4,4',6,6'-tetrakis(3,4,5-trihyroxybenzoyl)-β,β'-D,D'-glucopyranosyl-(2,3'-oxy-di-benzoate). $^{1}$H NMR (CDCl$_3$, 360 MHz) δ 8.18 (m, 24H, ArOH), δ 7.91 (m, 1H, ArH(3)), δ 7.71 (d, J=7.8 Hz, 1H, ArH(4)'), δ 7.60-7.53 (m, 2H), δ 7.4-6.94 (m, 20H, ArH), δ 6.39 (d, J=8.2 Hz, 1H, H(1)), δ 6.35 (d. J=8.2 Hz, 1H, H(1)'), δ 6.04 (app. t. J=9.8 Hz, 1H, H(3)), δ 5.97 (app. t. J=9.6 Hz, 1H, H(3)'), δ 5.71-5.56 (m, 4H, H(2), H(2)', H(4), H(4)'), δ 4.61-4.40 (m, 6H, H(5), H(5)', H$_a$(6), H$_a$(6)', H$_b$(6), H$_b$(6)'); $^{13}$C NMR ((CD$_3$)$_2$CO, 90 MHz) δ 166.0, 165.4, 165.2, 165.1, 165.1, 164.1, 164.1, 162.6, 157.9, 156.6, 145.6, 145.5, 145.4, 138.9, 138.7, 138.6, 135.5, 132.3, 130.8, 130.7, 124.9, 124.6, 124.2, 121.8, 121.3, 121.3, 120.9, 119.6, 109.8, 109.8, 109.7, 93.4, 93.0, 73.6, 73.5, 72.8, 72.6, 71.3, 71.2, 68.8, 68.7, 62.3, 62.2, 62.2; MS (+MALDI) 1822 (MNa$^+$).

MATERIALS

Compounds were synthesized in the laboratory. LPS (*E. coli* 055:B5 phenol extract). Ficoll-Histopaque (p=1.077 g/mL), Fetal Bovine Serum, Sterile, hybridoma tested (FCS), gentamicin 10 mg/mL. L-glutamine, Dextran B-512 *Leuconostoc* Av M.W. 580000 and Trypan Blue stain (0.4%) were purchased from Sigma. Hanks Buffer Saline Solution 1×, with phenol red, mediatech (HBSS) and RPMI 1640 1×, mediatech were purchased from Fisher Scientific. Human, rat and mouse IL-1β and TNF-α ELISA kits were purchased from R and D Systems, Minneapolis, Minn. Fresh heparinized human blood was obtained from healthy human subjects. C3H/HeJ and C3H/HeOuJ mice were obtained from Jackson Labs, Bay City, Me.

TABLE 1

Secretion of TNF-α from mouse PEC's stimulated with LPS
(SD = Standard Deviation for all of the tables)

| conc. LPS ng/mL | TNF-α secreted from C3H/HeOuJ pg/mL ± SD | TNF-α secreted from C3H/HeJ pg/mL ± SD |
|---|---|---|
| 0 | 10.3 ± 1.9 | 10.3 ± 2.8 |
| 0.5 | 529.8 ± 4.8 | 7.6 ± 2.1 |
| 1 | 662.2 ± 36.7 | 7.9 ± 1.6 |
| 5 | 675.2 ± 0 | 9.7 ± 2.4 |
| 10 | 626.1 ± 16.1 | 6.7 ± 2.1 |
| 20 | 590.3 ± 27.0 | 9.4 ± 1.9 |
| 30 | 602.9 ± 25.1 | 10.9 ± 1.4 |

TABLE 2

Secretion of TNF-α from mouse PEC's stimulated with 16.

| conc. 16 μM | TNF-α secreted from C3H/HeOuJ pg/mL ± SD | TNF-α secreted from C3H/HeJ pg/mL ± SD |
|---|---|---|
| 0 | 18.9 ± 2.3 | 20.2 ± 21.1 |
| 0.3 | 17.5 ± 5.1 | 26.4 ± 29.0 |
| 1.3 | 49.8 ± 7.5 | 27.0 ± 29.0 |
| 2.7 | 111.2 ± 10.9 | 26.4 ± 24.6 |
| 5.3 | 30.5 ± 15.6 | 32.9 ± 32.9 |
| 8.0 | 25.4 ± 5.0 | 38.7 ± 40.6 |
| 10.6 | 38.0 ± 8.1 | 37.7 ± 39.7 |

TABLE 3

Secretion of TNF-α from treatment of rats with LPS + 1 and, independently, with LPS only.

| Rat | TNF-α secreted from 90 min pg/mL ± SD | TNF-α secreted after 180 min pg/mL ± SD |
|---|---|---|
| 1 (LPS + 1) | 8060.7 ± 918.2 | 1347.5 ± 150.4 |
| 2 (LPS + 1) | 1928.4 ± 331.5 | 129.9 ± 105.5 |
| 3 (LPS + 1) | 6919.4 ± 823.2 | 733.9 ± 28.3 |
| 4 (LPS + 1) | 4509.4 ± 583.3 | 291.7 ± 68.0 |
| 5 (LPS only) | 12582.0 ± 597.7 | 533.8 ± 116.8 |
| 6 (LPS only) | 14451.9 ± 910.3 | 863.8 ± 393.9 |
| 7 (LPS only) | 5536.4 ± 1635.3 | 593.7 ± 193.3 |
| 8 (LPS only) | 13397.3 ± 1014.2 | 694.8 ± 28.2 |
| 9 (LPS only) | 8636.1 ± 1723.3 | 202.8 ± 74.7 |

TABLE 4

Secretion of TNF-α from h-PBMC's stimulated with 17c-21c.

| conc. 17c-21c μM | TNF-α secreted in the presence of 17c pg/mL ± SD | TNF-α secreted in the presence of 18c pg/mL ± SD | TNF-α secreted in the presence of 19c pg/mL ± SD | TNF-α secreted in the presence of 20c pg/mL ± SD | TNF-α secreted in the presence of 21c pg/mL ± SD |
|---|---|---|---|---|---|
| 0 | 0 | 17.8 ± 8.8 | 105.2 ± 49.3 | 0 | 279.6 ± 80.0 |
| 0.6 | 0 | 8.9 ± 5.6 | 73.4 ± 58.3 | 0 | 140.7 ± 50.1 |
| 2.8 | | | | 0 | 80.3 ± 38.1 |
| 2.9 | 0 | 11.9 ± 5.2 | 50.9 ± 28.0 | | |
| 5.6 | | | | 0 | 61.9 ± 11.7 |
| 5.9 | 0 | 6.7 ± 2.9 | 8.0 ± 8.0 | | |
| 11.2 | | | | 0 | 96.2 ± 8.9 |
| 11.8 | 0.26 ± 0.37 | 9.5 ± 7.2 | 9.5 ± 6.5 | | |
| 16.8 | | | | 0 | 379.3 ± 156.6 |
| 17.6 | 0 | 11.4 ± 9.2 | 24.5 ± 10.7 | | |
| 22.3 | | | | 0 | 618.0 ± 182.0 |
| 23.5 | 0.26 ± 0.37 | 3.3 ± 2.6 | 67.6 ± 21.0 | | |
| 27.9 | | | | 0 | 899.0 ± 368.4 |
| 29.4 | 2.5 ± 3.5 | 8.5 ± 3.5 | 117.8 ± 44.0 | | |

TABLE 5

Secretion of TNF-α over time from h-PBMC's stimulated with LPS and 17c-20c.

| Time h | TNF-α secreted in the presence of LPS pg/mL ± SD | TNF-α secreted in the presence of LPS and 17c pg/mL ± SD | TNF-α secreted in the presence of LPS and 18c pg/mL ± SD | TNF-α secreted in the presence of LPS and 19c pg/mL ± SD | TNF-α secreted in the presence of LPS and 20c pg/mL ± SD |
|---|---|---|---|---|---|
| 1 | 582.9 ± 49.2 | 511.2 ± 288.3 | 594.6 ± 93.2 | 328.2 ± 61.5 | 243.6 ± 52.8 |
| 4 | 3237.4 ± 758.1 | 1896.3 ± 140.9 | 1523.3 ± 472.8 | 1880.0 ± 20.1 | 2370.1 ± 95.7 |
| 8 | 4352.9 ± 422.5 | 2477.0 ± 148.2 | 2829.3 ± 52.6 | 1921.5 ± 399.8 | 2889.8 ± 383.2 |
| 12 | 2684.6 ± 696.9 | 2574.4 ± 459.9 | 2448.1 ± 43.6 | 2229.4 ± 353.1 | 2313.2 ± 339.1 |
| 16 | 2751.0 ± 175.2 | 1811.6 ± 352.9 | 3956.3 ± 524.5 | 2561.2 ± 718.8 | 2628.4 ± 571.0 |
| 24 | 2559.1 ± 8.7 | 2266.1 ± 353.3 | 2002.1 ± 95.1 | 2146.9 ± 69.3 | 2356.4 ± 400.3 |

TABLE 6

Inhibition of LPS induced TNF-α secretion from h-PBMC's by 18c-20c. Addition of substrate 45 minutes after LPS.

| conc. 18c-20c μM | TNF-α secreted in the presence of LPS and 18c % max. response ± SD | TNF-α secreted in the presence of LPS and 19c % max. response ± SD | TNF-α secreted in the presence of LPS and 20c % max. response ± SD |
|---|---|---|---|
| 0.6 | 69.0 ± 4.9 | 114.3 ± 11.9 | 89.8 ± 9.2 |
| 2.8 | | 83.5 ± 26.1 | |
| 2.9 | 71.9 ± 15.2 | | 65.6 ± 8.3 |
| 5.6 | | 79.4 ± 15.1 | |
| 5.9 | 59.5 ± 9.5 | | 67.1 ± 8.9 |
| 11.2 | | 92.4 ± 21.4 | |
| 11.7 | 54.4 ± 15.4 | | |
| 11.8 | | | 63.3 ± 4.7 |
| 22.4 | | 73.0 ± 12.6 | |
| 23.5 | 60.6 ± 9.9 | | 63.9 ± 13.9 |

TABLE 7

Secretion of IL-1β from h-PBMC's stimulated with 17c-20c.

| conc. 17c-20c μM | IL-1β secreted in the presence of 17c pg/mL ± SD | IL-1β secreted in the presence of 18c pg/mL ± SD | IL-1β secreted in the presence of 19c pg/mL ± SD | IL-1β secreted in the presence of 20c pg/mL ± SD |
|---|---|---|---|---|
| 0 | 83.5 ± 51.8 | 83.5 ± 51.8 | 83.5 ± 51.8 | 83.5 ± 51.8 |
| 0.6 | 0 | 0 | 54.2 ± 57.5 | 0 |
| 2.8 | | | 60.9 ± 58.6 | |
| 2.9 | 0 | 4.7 ± 8.1 | | 0 |
| 5.6 | | | 14.5 ± 25.2 | |
| 5.9 | 3.2 ± 3.6 | 3.2 ± 5.5 | | 0 |
| 11.2 | | | 9.4 ± 7.0 | |
| 11.8 | 329.7 ± 443.0 | 34.1 ± 48.2 | | 184.1 ± 260.3 |
| 16.8 | | | 41.3 ± 14.8 | |
| 17.6 | 140.5 ± 195.6 | 1266.0 ± 78.3 | | 230.0 ± 191.0 |

TABLE 7-continued

Secretion of IL = 1β from h-PBMC's stimulated with 17c-20c.

| conc. 17c-20c µM | IL-1β secreted in the presence of 17c pg/mL ± SD | IL-1β secreted in the presence of 18c pg/mL ± SD | IL-1β secreted in the presence of 19c pg/mL ± SD | IL-1β secreted in the presence of 20c pg/mL ± SD |
|---|---|---|---|---|
| 22.5 | | | 23.2 ± 18.0 | |
| 23.5 | 630.6 ± 283.1 | 631.2 ± 94.4 | | 0 |
| 28.1 | | | 41.3 ± 6.0 | |
| 29.4 | 690.1 ± 101.0 | 2113.4 ± 393.0 | | 204.2 ± 165.4 |

TABLE 8

Inhibition of LPS induced TNF-α secretion from h-PBMC's by 19c and 20c. Addition of substrate 45 minutes after LPS.

| Conc. of 19c and 20c µM | TNF-α secreted in the presence of LPS and 19c % max. response ± SD | TNF-α secreted in the presence of LPS and 20c % max. response ± SD |
|---|---|---|
| 0 | 100 ± 3.5 | 100 ± 3.5 |
| 0.6 | 85.1 ± 10.3 | 109.1 ± 14.9 |
| 1.7 | 78.3 ± 9.1 | |
| 1.8 | | 110.6 ± 1.3 |
| 3.4 | 81.8 ± 15.9 | |
| 3.5 | | 62.4 ± 10.2 |
| 5.6 | 57.5 ± 14.1 | |
| 5.9 | | 69.5 ± 27.9 |
| 11.2 | 57.4 ± 7.3 | |
| 11.8 | | 98.4 ± 12.1 |

It should be appreciated that the gallotannin and ellagitannin compositions of this invention may contain gallotannins and ellagitannins within the scope of the formulas described above, optical isomers, or prodrugs or analogues of these compounds or a racemic mixture of either the D or the L form. Also, minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

All articles cited herein and in the following list are hereby expressly incorporated in their entirety by reference.

CITATIONS

Barbara, J. A. J.; Van Ostade, X.; Lopez, A. F. Tumor Necrosis Factor-Alpha (TNF-α): The Good, the Bad and Potentially Very Effective. *Immunol. Cell. Biol.* 1996, 74, 434-443.

Berlinck. R. G. S.; Hatano, T.; Okuda, T.; Yoshida, T. In *Progress in the Chemistry of Organic Natural Products*; Herz, W., Kirby, G. W., Moore, R. E., Steglich, W., Tamm, Ch., Eds: Springer-Verlag: New York, 1995, p. 1.

Miyamoto, K.-I.; Kishi, N.; Koshiura, R.; Yoshida, T.; Hatano, T.; Okuda, T. *Chem. Pharm. Bull.* 1987, 35, 814.

Miyamoto, K.-I.; Murayama T.; Nomura, M.; Hatano T.; Yoshida T.; Furukawa T.; Koshiura R.; Okuda T. Antitumor activity and interleukin-1 induction by tannins. *Anticancer Res.* 1993; 13: 37-42.

Miyamoto, K.-I.; Murayama, T.; Nomura, M.; Hatano, T.; Yoshida, T.; Furukawa, T.; Koshiura, R.; Lkuda, T. *Anticancer Res.* 1993, 13, 37.

Sanches-Cantu, L., Rode, H. N.; Yun, T. J.; Christou, N. V. Tumor Necrosis Factor Alone Does Not Explain the Lethal Effect of Lipopolysaccharide. *Arch. Sure.* 1991. 126, 231-235.

Van Ostade, X.; Lopez, A. F. Tumor Necrosis Factor-Alpha (TNF-α): The Good, the Bad and Potentially Very Effective. *Immunol. Cell. Biol.* 1996, 74, 434-443.

What is claimed is:

1. A method of inhibiting the release of cytokines comprising: administering to a subject in need thereof a cytokine release inhibiting-effective amount of a gallotannin compound comprising a linker unit selected from the group consisting of:

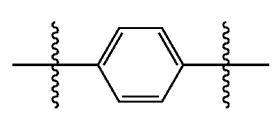

17

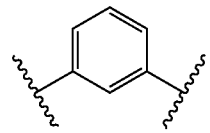

18

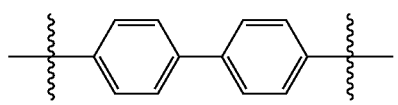

19

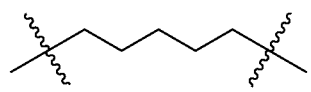

20

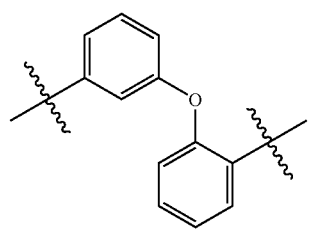

21 wherein the gallotannin compound is a dimeric gallotannin disposed in a pharmaceutically acceptable carrier, and wherein the linker unit joins carbohydrate cores of the dimeric gallotannin in a linkage that misaligns the carbohydrate cores.

2. A method of inhibiting the release of cytokines comprising administering to a subject in need thereof a cytokine release inhibiting effective amount of a gallotannin compound, wherein the compound is a dimeric gallotannin having the following structure:

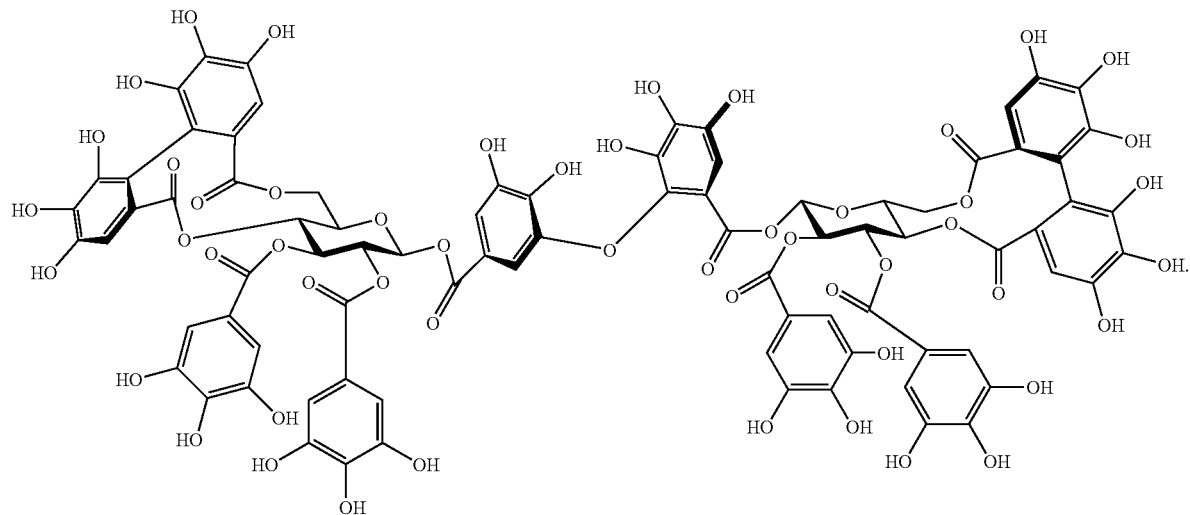
3. A dimeric gallotannin compound having the following structure:
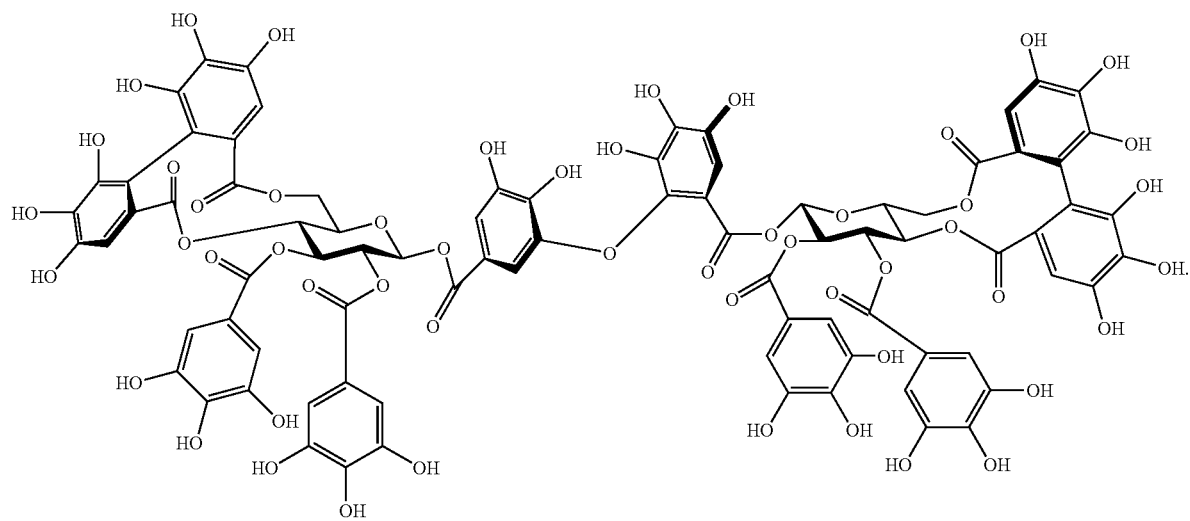
* * * * *

UNITED STATES PATENT AND TRADEMARK OFFICE
CERTIFICATE OF CORRECTION

PATENT NO.         : 7,288,273 B1                                     Page 1 of 1
APPLICATION NO. : 10/130632
DATED              : October 30, 2007
INVENTOR(S)        : Feldman It is certified that error appears in the above-identified patent and that said Letters Patent is hereby corrected as shown below:

<u>Col. 1, line 8:</u>

DELETE after government "may have"
ADD after government --has--

Signed and Sealed this

First Day of April, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,288,273 B1 | Page 1 of 1 |
| APPLICATION NO. | : 10/130632 | |
| DATED | : October 30, 2007 | |
| INVENTOR(S) | : Kenneth S. Feldman | |

It is certified that error appears in the above-identified patent and that said Letters Patent is hereby corrected as shown below:

In the Specification

Col. 1, Lines 4-9:
After GRANT REFERENCE, DELETE: "This invention was funded in part by a grant from the National Institutes of Health (NIH), grant number GM 35727. The Government may have certain rights in this invention."

After GRANT REFERENCE, ADD: --This invention was made with government support under Grant No. GM035727, awarded by the National Institutes of Health. The Government has certain rights in the invention.--

Signed and Sealed this
Eleventh Day of August, 2015

Michelle K. Lee
*Director of the United States Patent and Trademark Office*